(12) United States Patent
Franch et al.

(10) Patent No.: US 7,915,201 B2
(45) Date of Patent: Mar. 29, 2011

(54) LIGATIONAL ENCODING OF SMALL MOLECULES

(75) Inventors: Thomas Franch, Snekkersten (DK); Soeren Nyboe Jacobsen, Frederiksberg (DK); Torben Ravn Rasmussen, Ballerup (DK); Soeren Neve, Lyngby (DK); Henrik Pedersen, Bagsvaerd (DK); Alex Haahr Gouliaev, Veksoe Sjaelland (DK)

(73) Assignee: Nuevolution A/S, Copenhagen OE (DK)

( * ) Notice: Subject to any disclaimer, the term of this patent is extended or adjusted under 35 U.S.C. 154(b) by 884 days.

(21) Appl. No.: 10/549,619

(22) PCT Filed: Mar. 22, 2004

(86) PCT No.: PCT/DK2004/000195
§ 371 (c)(1),
(2), (4) Date: Feb. 28, 2006

(87) PCT Pub. No.: WO2004/083427
PCT Pub. Date: Sep. 30, 2004

(65) Prior Publication Data
US 2006/0246450 A1 Nov. 2, 2006

Related U.S. Application Data

(60) Provisional application No. 60/455,858, filed on Mar. 20, 2003.

(30) Foreign Application Priority Data

Mar. 20, 2003 (DK) .................................. 2003 00430

(51) Int. Cl.
*C40B 50/00* (2006.01)
*C40B 30/00* (2006.01)
(52) U.S. Cl. ..................... 506/23; 506/4; 506/7; 506/13; 506/28; 435/6; 435/91.2; 536/23.1
(58) Field of Classification Search ........................ None
See application file for complete search history.

(56) References Cited

U.S. PATENT DOCUMENTS

| | | | |
|---|---|---|---|
| 4,822,731 A | 4/1989 | Watson et al. |
| 5,476,930 A | 12/1995 | Letsinger et al. |
| 5,503,805 A | 4/1996 | Sugarman et al. |
| 5,571,903 A | 11/1996 | Gryaznov |
| 5,573,905 A | 11/1996 | Lerner et al. |
| 5,639,603 A | 6/1997 | Dower et al. |
| 5,665,975 A | 9/1997 | Kedar |
| 5,681,943 A | 10/1997 | Letsinger et al. |
| 5,708,153 A | 1/1998 | Dower et al. |
| 5,723,598 A | 3/1998 | Lerner et al. |
| 5,741,643 A | 4/1998 | Gryaznov et al. |
| 5,770,358 A | 6/1998 | Dower et al. |
| 5,780,613 A | 7/1998 | Letsinger et al. |
| 5,789,162 A | 8/1998 | Dower et al. |
| 5,830,658 A | 11/1998 | Gryaznov et al. |
| 5,840,485 A | 11/1998 | Lebl et al. |
| 5,843,650 A | 12/1998 | Segev |
| 6,056,926 A | 5/2000 | Sugarman et al. |
| 6,060,596 A | 5/2000 | Lerner et al. |
| 6,140,493 A | 10/2000 | Dower et al. |
| 6,143,497 A | 11/2000 | Dower et al. |
| 6,143,503 A | 11/2000 | Baskerville et al. |
| 6,165,717 A | 12/2000 | Dower et al. |
| 6,165,778 A | 12/2000 | Kedar |
| 6,207,446 B1 | 3/2001 | Szostak et al. |
| 6,297,053 B1 | 10/2001 | Stemmer |
| 6,416,949 B1 | 7/2002 | Dower et al. |

(Continued)

FOREIGN PATENT DOCUMENTS

DE 19646372 6/1997

(Continued)

OTHER PUBLICATIONS

Nemoto, N et al. "In vitro virus: bonding of mRNA bearing puromycin at the 3'-terminal end to the C-terminal end of its encoded protein on the ribosome in vitro". FEBS Lett. Sep. 8, 1997;414(2):405-8.
Roberts, RW et al. "RNA-peptide fusions for the in vitro selection of peptides and proteins". Proc Natl Acad Sci U S A. Nov. 11, 1997;94(23):12297-302.
Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.

(Continued)

*Primary Examiner* — Heather Calamita
(74) *Attorney, Agent, or Firm* — Iver P. Cooper

(57) ABSTRACT

The invention relates to a method for synthesising a bifunctional complex comprising an encoded molecule and an identifier polynucleotide identifying the chemical entities having participated in the synthesis of the encoded molecule, said method comprising the steps of i) providing a) at least one template comprising one or more codons capable of hybridising to an anti-codon, wherein said template is optionally associated with one or more chemical entities, and b) a plurality of building blocks each comprising an anti-codon associated with one or more chemical entities, and ii) hybridising the anti-codon of one or more of the provided building blocks to the template, iii) covalently linking said anti-codons and/or linking the at least one template with the anti-codon of at least one building block, thereby generating an identifier polynucleotide capable of identifying chemical entities having participated in the synthesis of the encoded molecule, iv) separating the template from one or more of the anti-codons hybridised thereto, thereby generating an at least partly single stranded identifier polynucleotide associated with a plurality of chemical entities, v) generating a bifunctional complex comprising an encoded molecule and an identifier polynucleotide identifying the chemical entities having participated in the synthesis of the encoded molecule, wherein said encoded molecule is generated by reacting at least two of said plurality of chemical entities associated with the identifier polynucleotide, and wherein said at least two chemical entities are provided by separate building blocks.

31 Claims, 19 Drawing Sheets

U.S. PATENT DOCUMENTS

| | | |
|---|---|---|
| 6,429,300 B1 | 8/2002 | Kurz et al. |
| 6,593,088 B1 | 7/2003 | Saito et al. |
| 6,620,587 B1 | 9/2003 | Taussig et al. |
| 2003/0004122 A1 | 1/2003 | Beigelman et al. |
| 2003/0113738 A1* | 6/2003 | Liu et al. ............... 435/6 |
| 2005/0025766 A1 | 2/2005 | Liu et al. |
| 2005/0042669 A1 | 2/2005 | Liu et al. |
| 2005/0142583 A1 | 6/2005 | Liu |
| 2005/0170376 A1 | 8/2005 | Liu |

FOREIGN PATENT DOCUMENTS

| | | |
|---|---|---|
| EP | 0324616 | 7/1989 |
| EP | 0604552 | 4/1993 |
| EP | 0643778 | 10/1993 |
| EP | 0695305 | 10/1994 |
| EP | 0776330 | 10/1996 |
| EP | 0773227 | 5/1997 |
| EP | 1533385 | 5/2005 |
| WO | 9005785 | 5/1990 |
| WO | 9105058 | 4/1991 |
| WO | 9303172 | 2/1993 |
| WO | 9504160 | 2/1995 |
| WO | 9512608 | 5/1995 |
| WO | 9609316 | 3/1996 |
| WO | 9612014 | 4/1996 |
| WO | 9635699 | 11/1996 |
| WO | 9831700 | 7/1998 |
| WO | 9856904 | 12/1998 |
| WO | 9951773 | 10/1999 |
| WO | 0021909 | 4/2000 |
| WO | 0023458 | 4/2000 |
| WO | 0032823 | 6/2000 |
| WO | 0047775 | 8/2000 |
| WO | 0061775 | 10/2000 |
| WO | 0100876 | 1/2001 |
| WO | 02074929 | 9/2002 |
| WO | 02102820 | 12/2002 |
| WO | 02103008 | 12/2002 |
| WO | WO 02/103008 * | 12/2002 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03078627 | 9/2003 |
| WO | 03082901 | 10/2003 |
| WO | 2004001042 | 12/2003 |
| WO | 2004009814 | 1/2004 |
| WO | 2004013070 | 2/2004 |
| WO | 2004016767 | 2/2004 |
| WO | 2004024929 | 3/2004 |
| WO | 2004039825 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 | 11/2004 |
| WO | 2004110964 | 12/2004 |
| WO | 2005003778 | 1/2005 |
| WO | 2005026387 | 3/2005 |
| WO | 2006048025 | 5/2006 |
| WO | 2006053571 | 5/2006 |

OTHER PUBLICATIONS

Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.

Keller et al. "Role of a peptide tagging system in degradation of proteins synthesized from damaged messenger RNA". Science. Feb. 16, 1996;271(5251):990-3.

Benner, SA. "Expanding the genetic lexicon: incorporating non-standard amino acids into proteins by ribosome-based synthesis". Trends Biotechnol. May 1994;12(5):158-63.

Mendel, D."Site-directed mutagenesis with an expanded genetic code". Annu. Rev. Biophys. Biomol. Struc. 1995. 24:463-93.

Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.

Liu DR et al. "Progress toward the evolution of an organism with an expanded genetic code". Proc Natl Acad Sci USA. Apr. 27, 1999;96(9):4780-5.

Liu, R et al. "Optimized synthesis of RNA-protein fusions for in vitro protein selection". Methods Enzymol. 2000;318:268-93.

Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.

Ellman J.A., et al. "Biosynthetic method for introducing Unnatural Amino acids site specifically into proteins". Methods Enzymol. 202, 301-336 (1992).

José Salas et al. "Biosynthetic Polydeoxynucleotides as Direct Templates for Polypeptide Synthesis". J. of Biological Chemistry, vol. 243, No. 6, 1968, p. 1012-1015.

Walder JA, Walder RY, Heller MJ, Freier SM, Letsinger RL, Klotz IM. "Complementary carrier peptide synthesis: general strategy and implications for prebiotic origin of peptide synthesis". Proc Natl Acad Sci U S A. Jan. 1979;76(1):51-5.

Bruick et al. "Template-directed ligation of peptides to oligonucleotides" Chemistry and Biology, vol. 3, No. 1, Jan. 1996, p. 49-56.

Tamura K, Schimmel P. "Oligonucleotide-directed peptide synthesis in a ribosome- and ribozyme-free system". Proc Natl Acad Sci U S A. Feb. 13, 2001;98(4):1393-7.

Lewis RJ, Hanawalt PC. "Ligation of oligonucleotides by pyrimidine dimers—a missing 'link' in the origin of life?"22;298(5872):393-6.

Liu J, Taylor JS. "Template-directed photoligation of oligodeoxyribonucleotides via 4-thiothymidine". Nucleic Acids Res. Jul. 1, 1998;26(13):3300-4.

Fujimoto et al. "Template-directed photoreversible ligation of deoxyoligonudeotides via 5-Vinyldeoxyuridine" J. Am. Soc. 2000, 122, 5646-5647.

Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000, 41:33:6451-6454.

Kenzo Fujimoto, Naoki Ogawa, Masayuki Hayashi, Shigeo Matsuda & Isao Saito "Template directed photochemical synthesis of branched oligodeoxynucleotides via 5-carboxyvinyldeoxyuridine". Tetrahedron letters 2000, 41:49:9437-40.

Letsinger et al. "Chemical Ligation of oligonucleotides in the presence and absence of a template". J. Amer. Chem. Soc. 1993, 115, 3808-9.

Gryaznov SM, Letsinger RL. "Template controlled coupling and recombination of oligonucleotide blocks containing thiophosphoryl groups". Nucleic Acids Res. Mar. 25, 1993;21(6):1403-8.

Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.

Herrlein MK, Letsinger RL. "Selective chemical autoligation on a double-stranded DNA template". Nucleic Acids Res. Nov. 25, 1994;22(23):5076-8.

Letsinger, RL; Wu, T; Elghanian, R "Chemical and photochemical ligation of oligonucleotide blocks". Nucleosides and nucleotides, 16(5&6), 643-652 (1997).

Visscher J, Schwartz AW "Template-directed synthesis of acyclic oligonucleotide analogues". J Mol Evol. Dec. 1988-Feb. 1989;28(1-2):3-6.

Visscher J, Bakker CG, van der Woerd R, Schwartz AW "Template-directed oligomerization catalyzed by a polynucleotide analog". Science. Apr. 21, 1989;244(4902):329-31.

Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.

Zhan, ZJ and Lynn, DG "Chemical Amplification through template-directed synthesis". J. Am. Chem. Soc. 1997, 119, 12420-1.

Bruick RK, Koppitz M, Joyce GF, Orgel LE. "A simple procedure for constructing 5'-amino-terminated oligodeoxynucleotides in aqueous solution Nucleic Acids Res". Mar. 15, 1997;25(6):1309-10.

Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.

Xu, Y and Kool, E "Rapid and Selective selenium-mediated autoligation of DNA strands" J. Am. Chem. Soc. 2000, 122, 9040-1 Pub. on web Aug. 31, 2000.

Xu Y, Karalkar NB, Kool ET. "Nonenzymatic autoligation in direct three-color detection of RNA and DNA point mutations". Nat Biotechnol. Feb. 2001;19(2):148-52.

Li X, Zhan ZY, Knipe R, Lynn DG. "DNA-catalyzed polymerization". J Am Chem Soc. Feb. 6, 2002;124(5):746-7.

Czlapinski, JL and Sheppard, TL. "Nucleic acid template-directed assembly of metallosalen-DNA conjugates". J Am Chem Soc. Sep. 5, 2001;123(35):8618-9 published on the web Aug. 10, 2001.

Leitzel JC, Lynn DG "Template-directed ligation: from DNA towards different versatile templates". Chem Rec. 2001;1(1):53-62. Published online Jan. 30, 2001.

Schmidt JG, Nielsen PE, Orgel LE. "Information transfer from DNA to peptide nucleic acids by template-directed syntheses". Nucleic Acids Res. Dec. 1, 1997;25(23):4792-4796.

Dower, WJ et al. "In vitro selection as a powerful tool for the applied evolution of proteins and peptides".Current Opinion in Chemical Biology, 2002, 6:390-398.

Brenner, S and Lerner, RA . "Encoded combinatorial chemistry" Proc. Natl. Acad. Sci. USA. vol. 89, p. 5381-5383, Jun. 1992.

Gartner, Z; Liu, DR "The generality of DNA-templated synthesis as a basis for evolving non-natural small molecules". J Am Chem Soc. Jul. 18, 2001;123(28):6961-3.

David Liu. "Expanding the reaction scope of DNA-templated synthesis Angew". Chem. Int. Ed. 2002, 41, No. 10 pp. 1796-1800. Published May 15, 2002.

Gartner, ZJ et al. "Multistep small-molecule synthesis programmed by DNA templates". J. Am. Chem. Soc. vol. 124, No. 35, 2002, 10304-10306.

Calderone, CT et al. "Directing otherwise incompatible reactions in a single solution by using DNA-templated organic synthesis". Angew Chem Int Ed, 2002, 41, No. 21. 4104-4108.

Bittker, JA; Phillips, KJ and Liu, DR "Recent advances in the in vitro evolution of nucleic acids". Curr Opin Chem Biol. Jun. 2002;6(3):367-74. Review. Pub. on the web 20$^{th}$ Mar. 2002.

Summerer,D and Marx, A "DNA-templated synthesis: more versatile than expected". Angew Chem Int Ed Engl. Jan. 4, 2002;41(1):89-90. Review.

Gartner, ZJ et al. "Two enabling architectures for DNA-templated organic synthesis ". Angew. Chem Int. Ed. 2003, 42, No. 12, 1370-1375.

Rosenbaum, DM et al. "Efficient and sequence-specific DNA-templated polymerization of peptide nucleic acid aldehydes". J. Am. Chem. Soc. vol. 125, No. 46, 2003, 13924-13925.

Li, X et al. "Stereoselectivity in DNA-templated organic synthesis and its origins". J. Am. Chem. Soc. vol. 125, No. 34, 2003, 10188-10189.

Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.

Otto, S et al. S"Recent developments in dynamic combinatorial chemistry". Current opinion in Chemical Biology 2002, 6: 321-327.

Pavia, MR. "The Chemical generation of molecular diversity". http://www.netsci.org/Science/Combichem/feature01.html.

Braun, E, et al. "DNA-templated assembly and electrode attachment of a conducting silver wire". Nature, vol. 391, Feb. 19, 1998, 775-778.

Tanaka, K et al. "Synthesis of a novel nucleoside for alternative DNA base pairing through metal complexation" J. Org. Chem. 1999, 64, 5002-5003.

Beger, M et al. "Universal bases for hybridization, replication and chain termination", Nucleic acids research, Oxford University Press, vol. 28, No. 15, pub. Aug. 1, 2000, p. 2911-2914.

Weizman, H et al. "2,2'-Bipyridine ligandoside: a novel building block for modifying DNA with intra-duplex metal complexes". J. Am. Chem. Soc. 2001, 123, 3375-3376.

Frutos, AG et al. "Demonstration of a word design strategy for DNA computing on surfaces". Nucleic Acids Research, 1997, vol. 25, No. 23, 4748-4757.

Loweth, CJ et al. "DNA-based assembly of gold nanocrystals". Angew. Chem. Int. Ed. 1999, 38, No. 12. 1808-1812.

Elghanian, R et al. "Selective colorimetric detection of polynucleotides based on the distance-dependent optical properties of gold nanoparticles". Science, vol. 277, Aug. 22, 1997,.

Storhoff, JJ and Mirkin, CA. "Programmed Materials Synthesis with DNA". Chem Rev. Jul. 14, 1999;99(7):1849-1862.

Mirkin CA. "Programming the assembly of two- and three-dimensional architectures with DNA and nanoscale inorganic building blocks". Inorg Chem. May 29, 2000;39(11):2258-72.

Waybright SM, Singleton CP, Wachter K, Murphy CJ, Bunz UH. "Oligonucleotide-directed assembly of materials: defined oligomers". J Am Chem Soc. Mar. 7, 2001;123(9):1828-33. Pub. on web Feb. 7, 2001.

Bruce Smith and Markus Krummenacker "DNA-guided assembly of proteins as a pathway to an assembler", (http://www.wadsworth.org/albcon97/abstract/krummena.htm); 1997 Albany Conference: Biomolecular Motors and Nanomachines.

DeWitt, SH et al. "Diversomers": an approach to nonpeptide, nonoligomeric chemical diversity. Proc. Natl. Acad. Sci, USA, vol. 90, pp. 6909-6913, Aug. 1993.

Nielsen, J et al. "Synthetic methods for the implementation of encoded combinatorial chemistry". J. Am. Chem. Soc. 1993, 115, 9812-9813.

Ohlmeyer, MHJ et al. "Complex synthetic chemical libraries indexed with molecular tags". Proc. Natl. Aced, Sci, USA, vol. 90, pp. 10922-10926, Dec. 1993, Chemistry.

Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.

Luo, P et al. "Analysis of the structure and stability of a backbone-modified oligonucleotide: implications for avoiding product inhibition in catalytic template-directed synthesis". J. Am. Chem. Soc. 1998, 120, 3019-3031.

Luther, A et al. "Surface-promoted replication and exponential amplification of DNA analogues". Nature, vol. 396, Nov. 19, 1998, 245-248.

Klekota, B et al. "Selection of DNA-Binding Compounds via Multistage Molecular Evolution". Tetrahedron 55 (1999) 11687-11697.

Furlan, RLE et al. "Molecular amplification in a dynamic combinatorial library using non-covalent interactions". Chem. Commun., 2000, 1761-1762.

Ramström, O et al. "In situ generation and screening of a dynamic combinatorial carbohydrate library against concanavalin A". ChemBioChem, 2000, 1, 41-48.

Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.

Roberts, SI et al. "Simultaneous selection, amplification and isolation of a pseudo-peptide receptor by an immobilised N-methyl ammonium ion template". Chem. Commun., 2002, 938-939.

Doyon, J.B et al. "Highly sensitive in vitro selections for DNA-linked synthetic small molecules with protein binding affinity and specificity" J. Am. Chem. Soc, Sep. 16, 2003.

Kanan, M.W et al. "Reaction discovery enabled by DNA-templated synthesis and in vitro selection" Nature, vol. 431, Sep. 30, 2004.

"Finding reactions in a haystack: Try'em all, see what works" Meeting American Chemical Society, Sep. 10, 2004, vol. 305, Science.

"The Nucleus", Jan. 2004, vol. LXXXII, No. 5, R. Grubina; "Summer Research Report: R. Grubina on DNA Templated Synthesis for Small Molecule Library", p. 10-14.

Nazarenko et al., "A closed tube format for amplification and detection of DNA based on energy transfer", Nucleic Acids Research, 1997, vol. 25, No. 12, p. 2516-2521.

Chan et al., "Intra-tRNA distance measurements for nucleocapsid protein-dependent tRNA unwinding during priming of HIV reverse transcription", PNAS vol. 96, p. 459-464, Jan. 1999.

Liu DR et al., DNA-templated synthesis as a basis for the evolution of synthetic molecules, Abstracts of Papers of the American Chemical Society; 225: 612-ORGN, Part 2, Mar. 2003.

Rodriguez et al., "Template-directed extension of a guanosine 5'-phosphate covalently attached to an oligodeoxycytidylate template", J Mol Evol (1991) 33:477-482.

Acevedo et al., "Template-directed oligonucleotide ligation on hydroxylapatite", Nature vol. 321, Jun. 19, 1986, p. 790-792.

Piccirilli, "RNA seeks its maker", Nature vol. 376, Aug. 17, 1995, p548-.

A. W. Schwartz et al., "Template-directed synthesis of novel, nucleic acid-like structures", Science 1985, 228, 585-7.

Halpin et al.: DNA display III. Solid-phase organic synthesis on unprotected DNA. PLoS Biol. Jul. 2004;2(7):E175. Epub Jun. 22, 2004.

Halpin et al.: DNA display II. Genetic manipulation of combinatorial chemistry libraries for small-molecule evolution. PLoS Biol. Jul. 2004;2(7):E174. Epub Jun. 22, 2004.

Halpin et al.: DNA display I. Sequence-encoded routing of DNA populations. PLoS Biol. Jul. 2004;2(7):E173. Epub Jun. 22, 2004.

"Highly Sensitive In Vitro Selections for DNA-Linked Synthetic Small Molecules with Protein Binding Affinity and Specificity" Doyon, J. B.; Snyder, T. M.; Liu, D. R. J. Am. Chem. Soc. 125, 12372-12373 (2003).

"Translation of DNA into Synthetic N-Acyloxazolidines" Li, X.; Gartner, Z. J.; Tse, B. N.; Liu, D. R. J. Am. Chem. Soc. 126, 5090-5092 (2004).

"DNA-Templated Organic Synthesis: Nature's Strategy for Controlling Chemical Reactivity Applied to Synthetic Molecules" Li, X.; Liu, D. R. Anew. Chem. Int. Ed. 43, 4848-4870 (2004).

"DNA-Templated Organic Synthesis and Selection of a Library of Macrocycles" Gartner, Z. J.; Tse, B. N.; Grubina, R.; Doyon, J. B.; Snyder, T. M.; Liu, D. R. Science 305, 1601-1605 (2004).

"Nucleic Acid-Templated Synthesis as a Model System for Ancient Translation" Calderone, C. T. and Liu, D. R. Curr. Opin. Chem. Biol. 8, 645-653 (2004).

"DNA-Templated Functional Group Transformations Enable Sequence-Programmed Synthesis Using Small-Molecule Reagents" Sakurai, K.; Snyder, T. M.; Liu, D. R. J. Am. Chem. Soc. 127, 1660-1661 (2005).

"Translating DNA into synthetic Molecules", David R. Liu, PLoS Biology, Jul. 2004, vol. 2, Iss. 7, p. 905-6.

"The Development of Amplifiable and Evolvable Unnatural Molecules", David R. Liu, Harvard Univ. Cambridge MA Dept of Chemistry and Chemical Biology. Report dated Aug. 4, 2003 No. A104614, approved for public release.

Website of Prof. David R. Liu, publicly available Mar. 11, 2000.
Website of Prof. David R. Liu, publicly available Oct. 15, 2000.
Website of Prof. David R. Liu, publicly available Mar. 1, 2001.
Website of Prof. David R. Liu, publicly available Apr. 19, 2001.
Website of Prof. David R. Liu, publicly available Sep. 23, 2001.
Website of Prof. David R. Liu, publicly available Sep. 24, 2002.
Website of Prof. David R. Liu, publicly available Nov. 20, 2002.
Website of Prof. David R. Liu, publicly available Oct. 15, 2003.

Inoue et al, Oligomerization of (Guanosine 5'-phosphor)-2-methylimidazolide on Poly(C), J. Mol. Biol. (1982), 162, 201-217.

C. B. Chen et al., "Template-directed synthesis on Oligodeoxycytidylate and Polydeoxycytidylate templates" J. Mol. Biol. 1985, 181, 271.

H. Rembold et al., "Single-strand regions of Poly(G) act as templates for oligo(C) synthesis" J. Mol. Evol. 1994, 38, 205.

T. Inoue et al., "A nonenzymatic RNA polymerase model", Science 1983, 219, p. 859-862.

O. L. Acevedo et al., "Non-enzymatic transcription of an oligonucleotide 14 residues long", J. Mol. Biol. 1987, 197, p. 187-193.

C. Böhler et al., "Template switching between PNA and RNA oligonucleotides", Nature 1995, 376, 578-581.

* cited by examiner

Fig.2
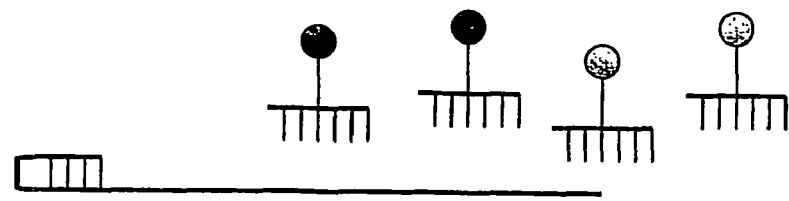
↓ -Ligate BB
-Remove excess BB
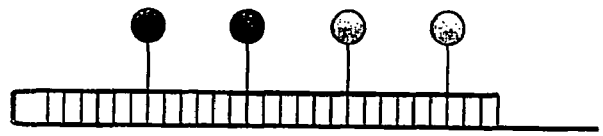
↓ -Denature
-Multiple reactions
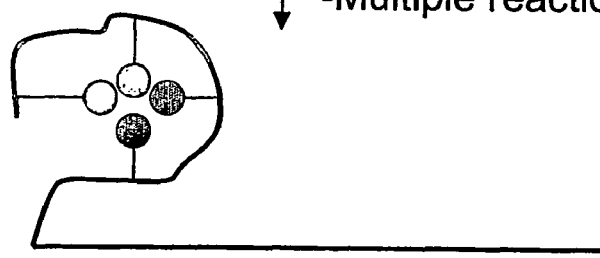
↓
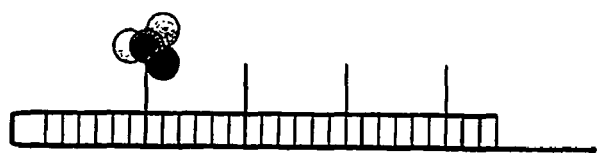

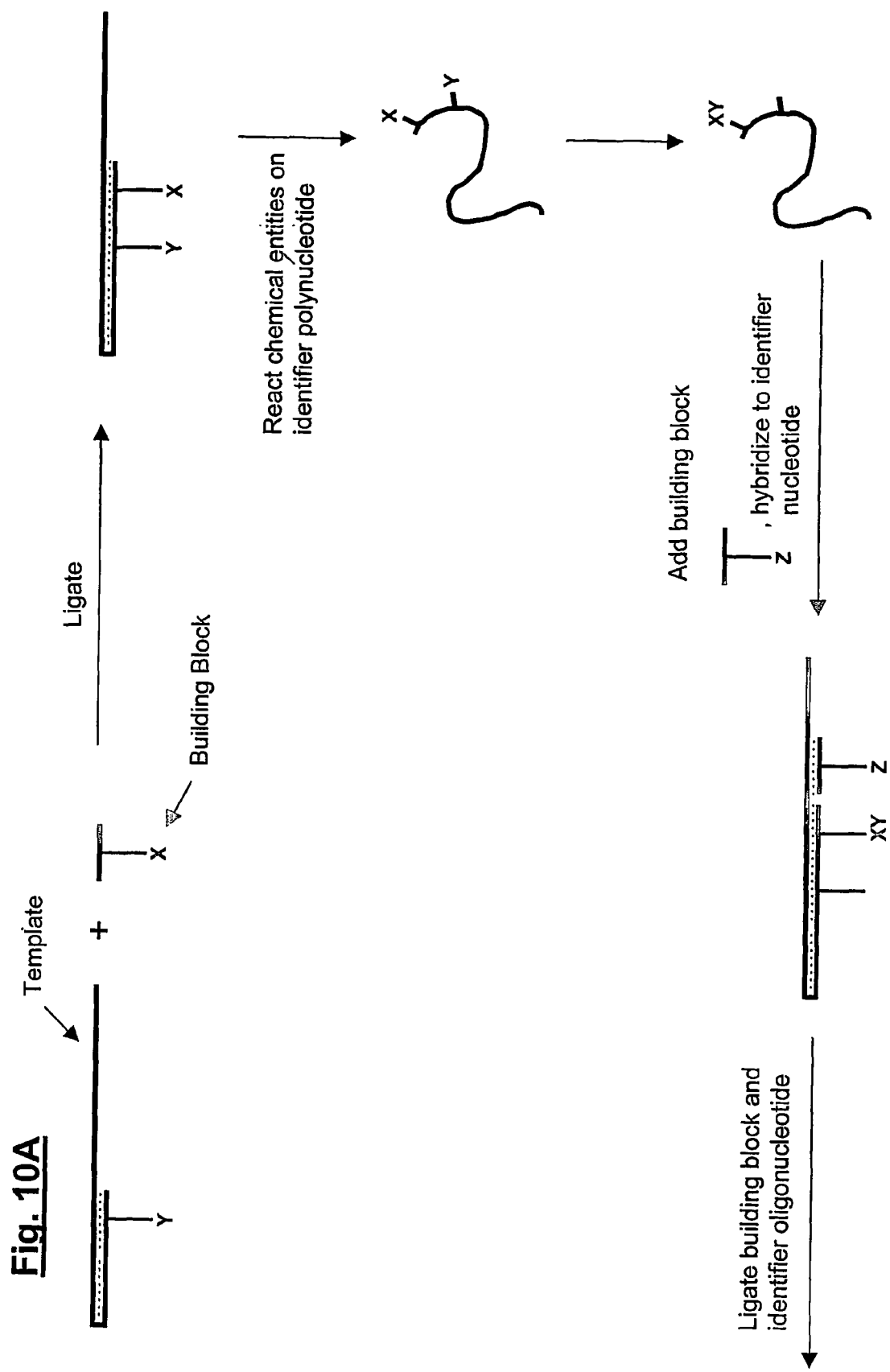

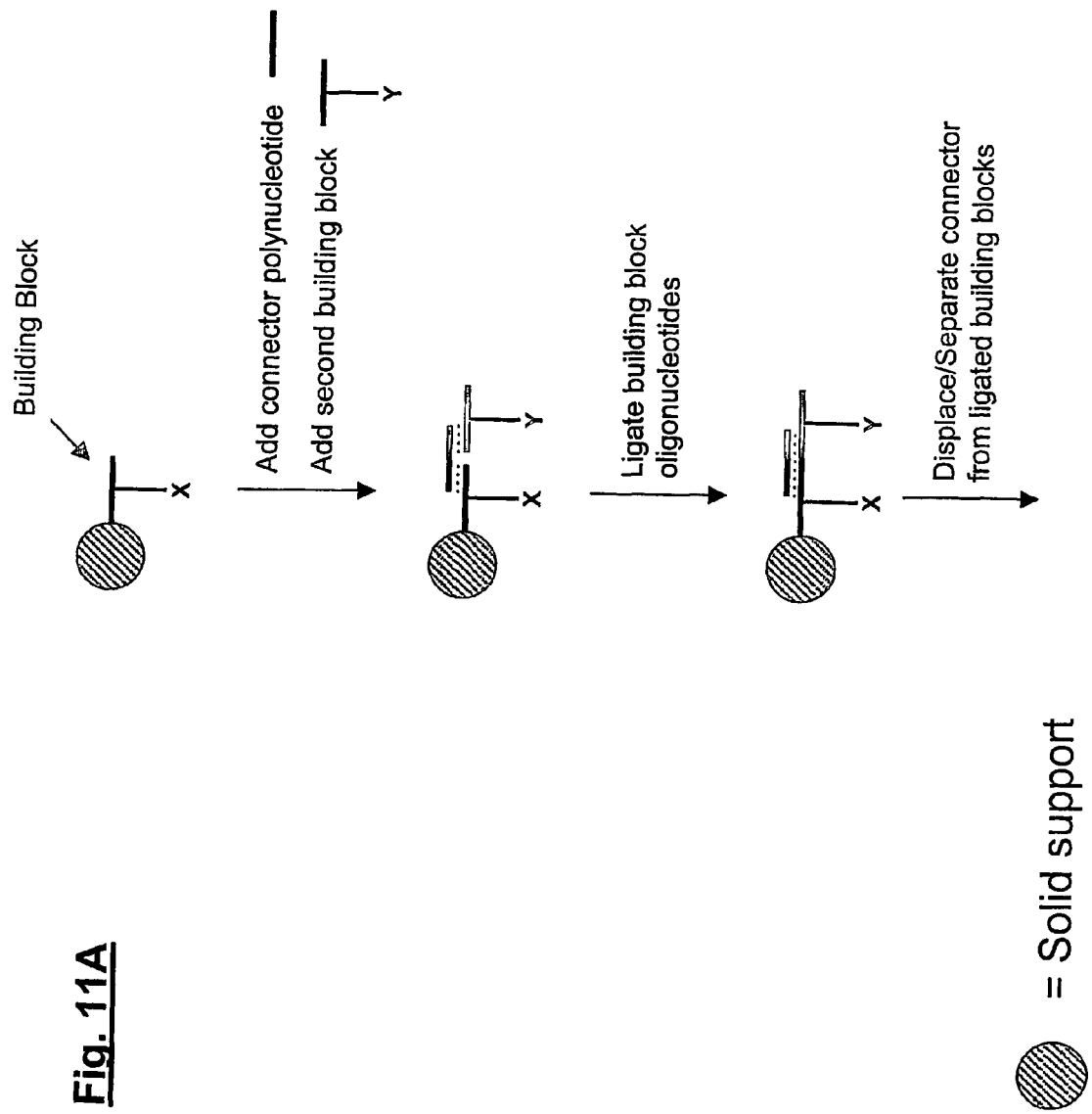

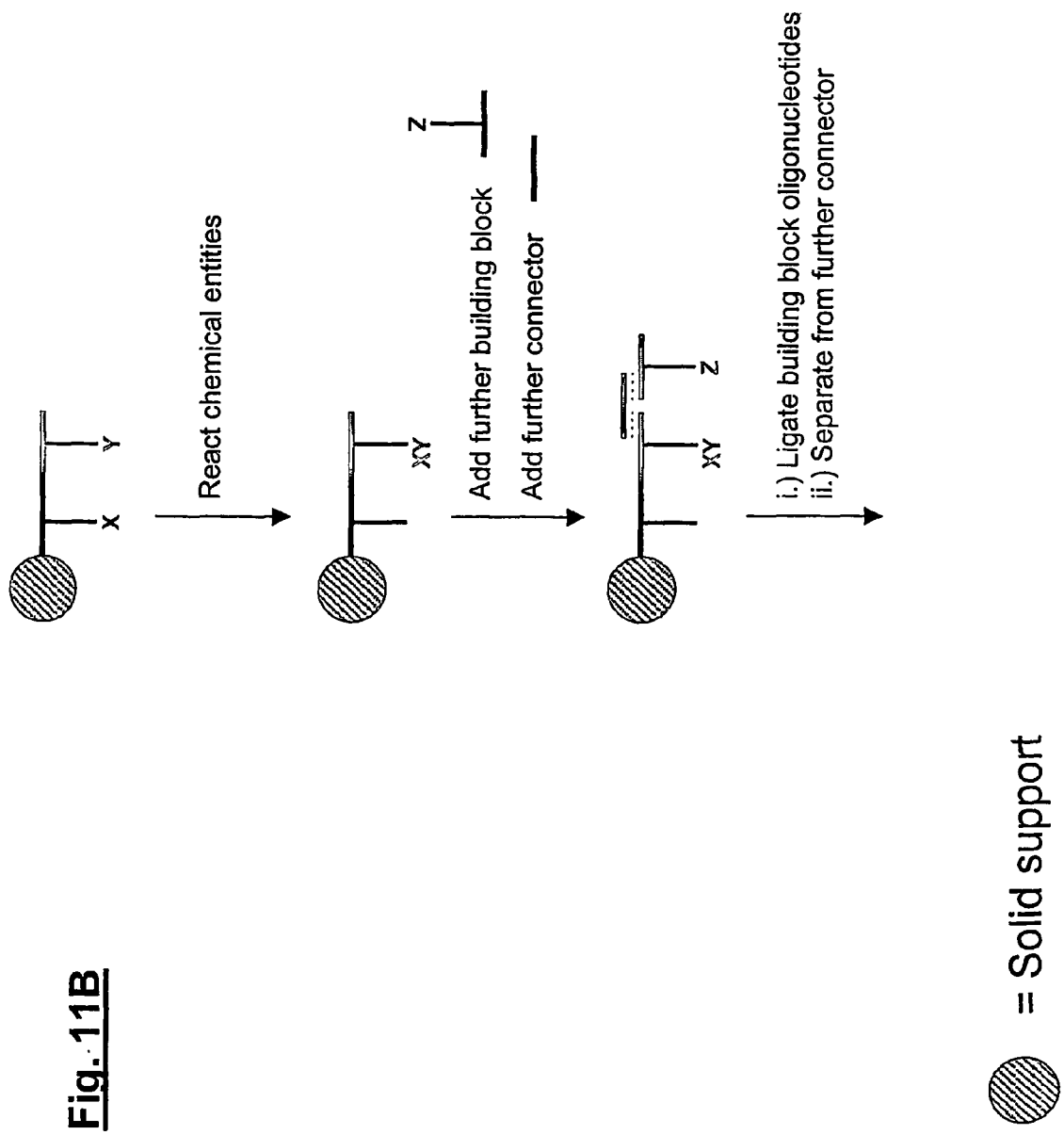

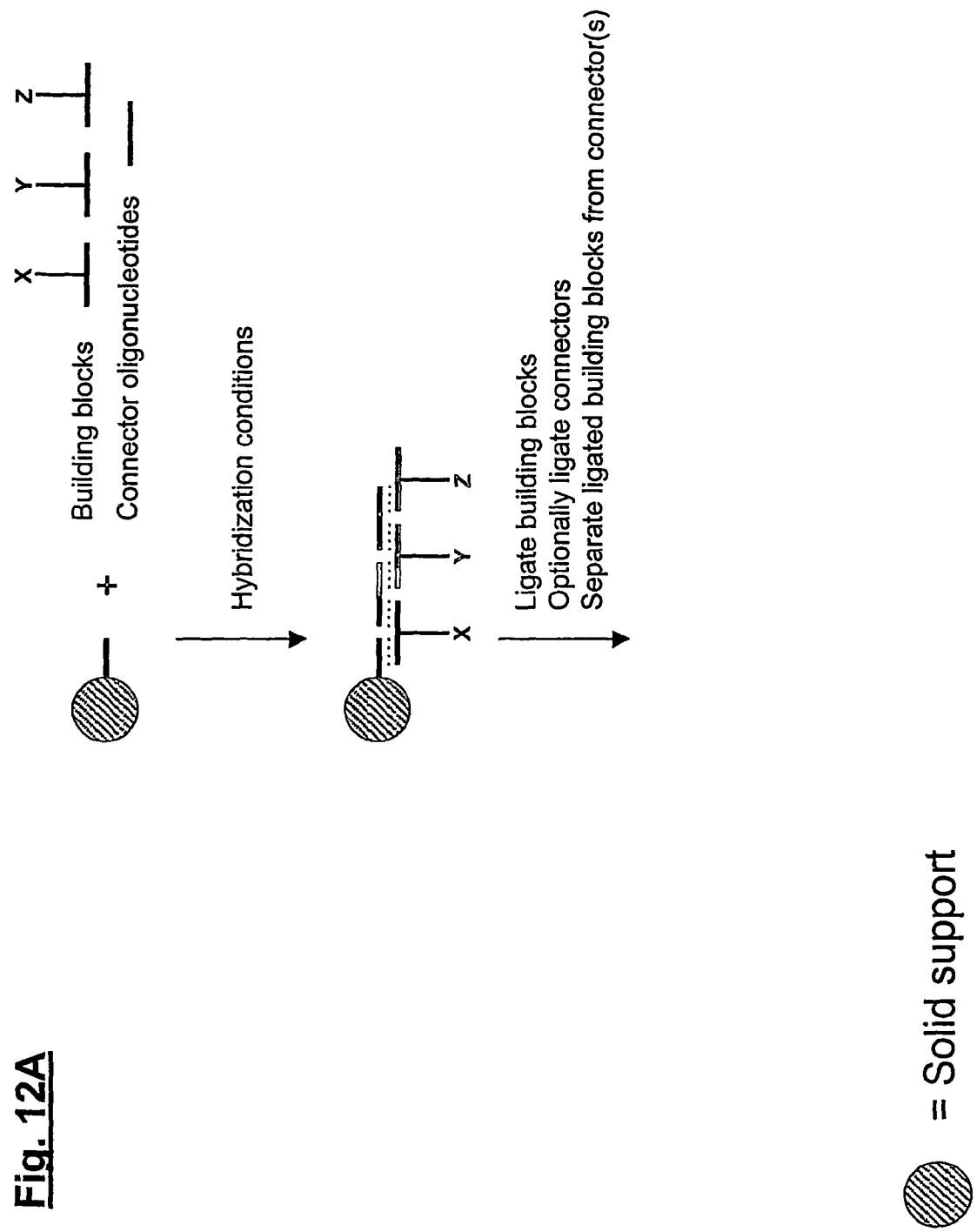

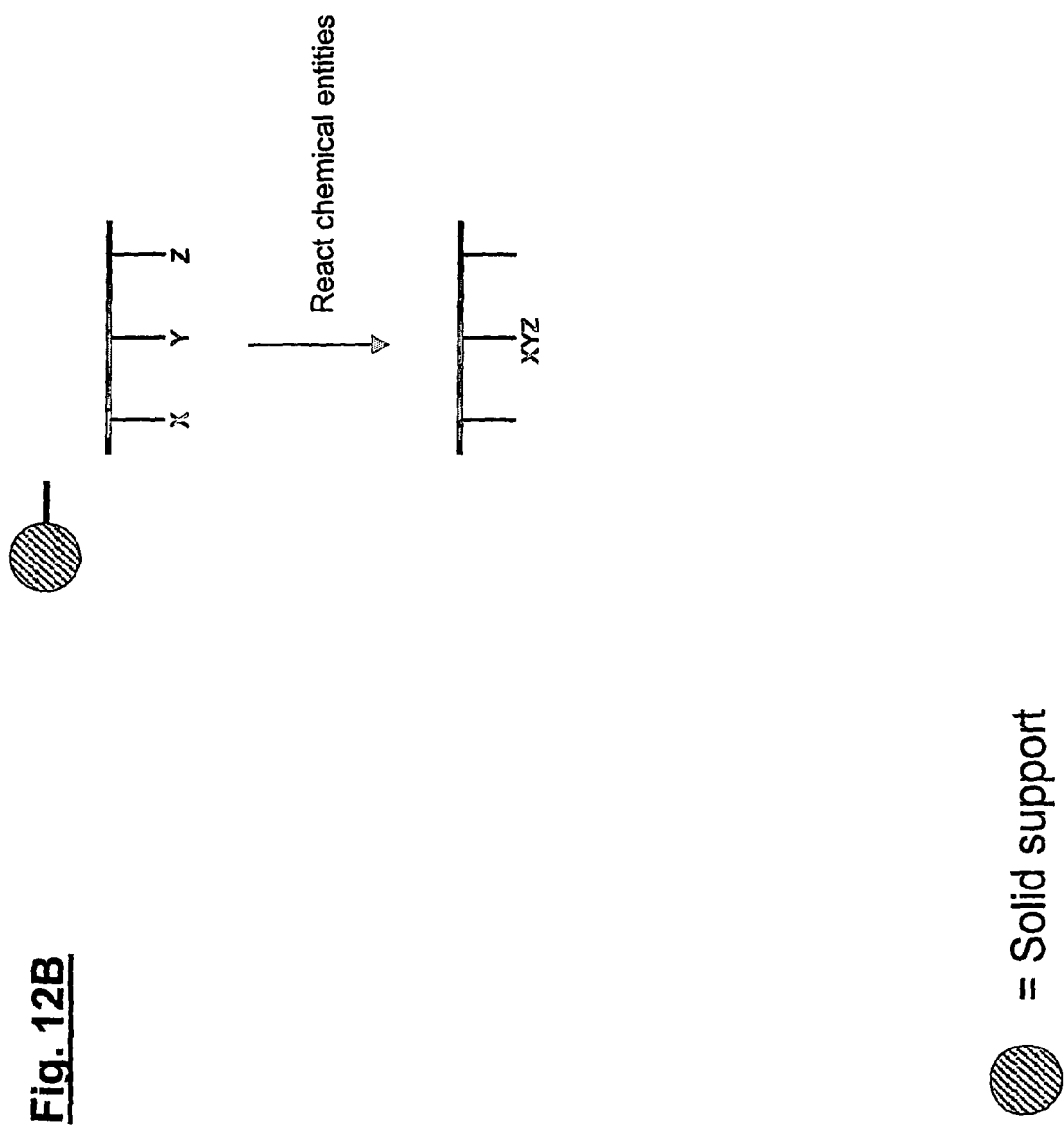

SEQUENCE LISTING

```
<160> NUMBER OF SEQ ID NOS: 19

<210> SEQ ID NO 1
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (2)..(3)
<223> OTHER INFORMATION: n is a, c, g, t or u
<220> FEATURE:
<221> NAME/KEY: misc_feature
<222> LOCATION: (5)..(6)
<223> OTHER INFORMATION: n is a, c, g, t or u

<400> SEQUENCE: 1 tnnanna                                                            7

<210> SEQ ID NO 2
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (2)..(3)
<223> OTHER INFORMATION: n is a, c, g, t or u
<220> FEATURE:
<221> NAME/KEY: misc_feature
<222> LOCATION: (5)..(6)
<223> OTHER INFORMATION: n is a, c, g, t or u
```

```
<400> SEQUENCE: 2 annannt                                                                  7

<210> SEQ ID NO 3
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (2)..(3)
<223> OTHER INFORMATION: n is a, c, g, t or u
<220> FEATURE:
<221> NAME/KEY: misc_feature
<222> LOCATION: (4)..(4)
<223> OTHER INFORMATION: carboxy d-T
<220> FEATURE:
<221> NAME/KEY: misc_feature
<222> LOCATION: (5)..(6)
<223> OTHER INFORMATION: n is a, c, g, t or u

<400> SEQUENCE: 3 tnnnnna                                                                  7

<210> SEQ ID NO 4
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (2)..(3)
<223> OTHER INFORMATION: n is a, c, g, t or u
<220> FEATURE:
<221> NAME/KEY: misc_feature
<222> LOCATION: (4)..(4)
<223> OTHER INFORMATION: Carboxy-dT
<220> FEATURE:
<221> NAME/KEY: misc_feature
<222> LOCATION: (5)..(6)
<223> OTHER INFORMATION: n is a, c, g, t or u

<400> SEQUENCE: 4 annnnnt                                                                  7

<210> SEQ ID NO 5
<211> LENGTH: 60
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (57)..(57)
<223> OTHER INFORMATION: Carboxy-dT

<400> SEQUENCE: 5
agcagttagt agtttgtact atgtagtacc tcgaccactt tttgtggtcg aggtacnaca       60

<210> SEQ ID NO 6
<211> LENGTH: 67
```

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (57)..(57)
<223> OTHER INFORMATION: Carboxy-dT
<220> FEATURE:
<221> NAME/KEY: misc_feature
<222> LOCATION: (64)..(64)
<223> OTHER INFORMATION: Carboxy-dT

<400> SEQUENCE: 6
agcagttagt agtttgtact atgtagtacc tcgaccactt tttgtggtcg aggtacnaca    60 tagnaca                                                              67

<210> SEQ ID NO 7
<211> LENGTH: 74
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (57)..(57)
<223> OTHER INFORMATION: Carboxy-dT
<220> FEATURE:
<221> NAME/KEY: misc_feature
<222> LOCATION: (64)..(64)
<223> OTHER INFORMATION: Carboxy-dT
<220> FEATURE:
<221> NAME/KEY: misc_feature
<222> LOCATION: (71)..(71)
<223> OTHER INFORMATION: Carboxy-dT

<400> SEQUENCE: 7
agcagttagt agtttgtact atgtagtacc tcgaccactt tttgtggtcg aggtacnaca    60
tagnacaaac nact                                                      74

<210> SEQ ID NO 8
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (4)..(4)
<223> OTHER INFORMATION: C6 amino-dT

<400> SEQUENCE: 8 atgncat                                                              7

<210> SEQ ID NO 9
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(4)
<223> OTHER INFORMATION: carboxy-dT

<400> SEQUENCE: 9 atcngta                                                              7
```

-continued

```
<210> SEQ ID NO 10
<211> LENGTH: 45
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate

<400> SEQUENCE: 10
ctaggtagta gacgatatct ctactaccta gatgacatat caagt            45

<210> SEQ ID NO 11
<211> LENGTH: 53
<212> TYPE: DNA
<213> ORGANISM: Artificial
<220> FEATURE:
<223> OTHER INFORMATION: synthetic

<400> SEQUENCE: 11
agcagtttgt agtaagtact ttgtagtacc tcgaccactt tttgtggtcg agg    53

<210> SEQ ID NO 12
<211> LENGTH: 62
<212> TYPE: DNA
<213> ORGANISM: Artificial
<220> FEATURE:
<223> OTHER INFORMATION: synthetic

<400> SEQUENCE: 12
attgagcagt tagtagtttg tactatgtag tacctcgacc acctatatgt ctgtggtcga    60
gg                                                                  62

<210> SEQ ID NO 13
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (4)..(4)
<223> OTHER INFORMATION: carboxy dT

<400> SEQUENCE: 13 tacnaca                                                             7

<210> SEQ ID NO 14
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (4)..(4)
<223> OTHER INFORMATION: carboxy dT

<400> SEQUENCE: 14
``` tacnaca                                                          7

<210> SEQ ID NO 15
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (4)..(4)
<223> OTHER INFORMATION: carboxy dT

<400> SEQUENCE: 15 aacnact                                                          7

<210> SEQ ID NO 16
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate

<400> SEQUENCE: 16 acttgat                                                          7

<210> SEQ ID NO 17
<211> LENGTH: 7
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate

<400> SEQUENCE: 17 atgtcat                                                          7

<210> SEQ ID NO 18
<211> LENGTH: 59
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: phosphate

<400> SEQUENCE: 18
acttgatatg tcatctaggt agtagacgat atctctacta cctagatgac atatcaagt      59

<210> SEQ ID NO 19
<211> LENGTH: 7
<212> TYPE: DNA
<213> ORGANISM: Artificial
<220> FEATURE:
<223> OTHER INFORMATION: synthetic

```
<400> SEQUENCE: 19 atgcctg                                                                                    7
```

LIGATIONAL ENCODING OF SMALL MOLECULES

This application claims the benefit of U.S. provisional application Ser. No. 60/455,858 filed Mar. 20, 2003, which is hereby incorporated by reference in its entirety. All patent and non-patent references cited in that application, or in the present application, are also hereby incorporated by reference in their entirety.

TECHNICAL FIELD OF THE INVENTION

The present invention in one aspect relates to a method for synthesizing a bifunctional complex comprising an encoded molecule and a template coding for chemical entities which have participated in the synthesis of the encoded molecule. The invention also relates to a library of different complexes, said library being obtainable by processing a plurality of different templates. The library of the invention may be suitable for identifying drugs.

BACKGROUND OF THE INVENTION

Libraries of complexes comprising an encoded molecule as well as the template which has coded for the synthesis thereof are useful in finding new chemical compounds which may be used for therapeutic purposes, because the potential drug is connected to an identifier molecule or template, which may be decoded for identification of each chemical entity that has participated in the synthetic history.

Some attempts to form the complex comprising an encoded molecule as well as the template that codes for the chemical entity that has participated in the formation of the encoded molecule, were based on the split-and-mix principle known from combinatorial chemistry, see e.g. WO 93/06121 A1, EP 643 778 B1, and WO 00/23458. If several selection rounds are desirable or necessary the split-and-mix principle has the inherent disadvantage of requiring decoding between each selection round. The decoding step may be laborious and cumbersome because the templates usually are incorporated into a vector and then subsequently into a suitable host micro organism.

Other attempts have focussed on the formation of encoded proteins using the natural machinery of a cell and connecting the formed protein with the template nucleic acid that has coded for the amino acid components of the protein. Examples of suitable systems are phage display, E. coli display, ribosome display (WO 93/03172), and protein-mRNA-fusions (WO 98/31700). The genetic information of the nucleic acid, usually mRNA or DNA, may not necessarily be decoded between each round of selection to establish the identity of the chemical entities that has formed the protein because the nucleic acid can be amplified by known means, such as PCR, and processed for the formation of a new library enriched in respect of suitable binding proteins.

Recently, new a method for encoding molecules has been suggested, which can be performed in several selection rounds without intermediate decoding, wherein the en-coded molecule is not restricted to peptides and proteins. WO 02/00419 and WO 02/103008 disclose methods for preparing virtually any molecule connected to a template coding for chemical entities which have reacted to form the molecule. In short, a template segregated into a plurality of codons and a plurality of building blocks comprising a transferable chemical entity and an anticodon are initially provided. Under hybridisation conditions, the template and building blocks are annealed together and the chemical entities are subsequently reacted to form the molecule. The methods of the prior art are, however, restricted to reactions of the chemical entities which can be performed under hybridisation conditions. Hybridisation conditions generally imply aqueous solvents, moderate pH, and ambient temperature.

WO 02/074929 and WO 04/016767 disclose template directed synthesis methods in which the reactive units of functional groups are reacted while hybridised to a template. This severely restricts the applicability of these prior art methods.

DESCRIPTION OF THE INVENTION

The present invention in one aspect provides methods for the synthesis of molecules such as encoded molecules resulting from template directed synthesis involving a plurality of building blocks.

In another aspect the methods do not employ a template, but exploits building block oligonucleotides capable of hybridising to each other, thereby generating a hybridisation complex in which no single building block oligonucleotide hybridises to all of the remaining building block oligonucleotides of the complex.

In both of the above cases it is possible to generate an essentially single stranded identifier polynucleotide to which a plurality of chemical entities are attached, and react said chemical entities while the identifier polynucleotide is on a single stranded form, thereby enhancing the reactive proximity of several chemical entities and thereby in turn enhance the formation of a molecule resulting from the reaction of said chemical entities.

As the conditions for reacting the chemical entities is not limited to reaction conditions also facilitating hybridisation of nucleic acids, the types of reaction chemistries which can be pursued is increased significantly.

In some embodiments of the invention, the identifier polynucleotide is single stranded when chemical entities are reacted. This means that no single part of the identifier polynucleotide is hybridised to itself.

The term "separated" is used to denote that e.g. template codons and building block anti-codons do not hybridise to each other. Codons and anti-codons of an identifier polynucleotide can be "separated" while still being linked, such as covalently linked through at least one covalent chemical bond.

In some embodiments the identifier oligonucleotide consists only of the covalently linked oligonucleotide parts, such as e.g. anti-codons, of building blocks. Accordingly, it is possible to obtain a bifunctional complex in which no part of a template is present, wherein said template served the purpose of bringing building block chemical entities into reactive contact with one another.

In other embodiments, the identifier oligonucleotide comprises covalently linked building block oligonucleotides and at least a part of the template having templated the synthesis of an encoded molecule. In such cases, chemical entities are preferably also reacted under conditions in which the identifier polynucleotide is at least essentially single stranded.

"At least essentially single stranded" as used herein denotes in one embodiment that any formation non-single stranded structures of the identifier polynucleotide is transient, unintentional and not important for the reaction of chemical entities associated therewith. In other words, the reaction of the chemical entities does not benefit from the formation of the non-single stranded structures.

In one embodiment template codons and building block oligonucleotides or anti-codons are physically separated.

This can take place when one or the other of said oligonucleotides are bound to a solid support. In that case one may cleave at least one chemical bond linking the template to a plurality of covalently linked building block oligonucleotides such as anti-codons.

The displacement of template from covalently linked anti-codons can take place according to any of a variety of well known state of the art methods for displacing oligonucleotides, including incubation at increased temperatures, washing with buffer solutions containing high salt, incubating in certain organic solvents, and the like.

The methods of the present invention can be controlled so that the identifier oligonucleotide in one extreme contains both the entire template and the plurality of covalently linked building block oligonucleotides, such as anti-codons, to be used for encoded molecule synthesis, and in another extreme the identifier oligonucleotide contains only covalently linked anti-codons and no part of the template.

In one embodiment, when only a plurality of building blocks and no template is used for the synthesis of molecules according to the invention, the identifier polynucleotide to which a plurality of chemical entities are associated comprises only the oligonucleotides identifying individual building block chemical entities.

Oligonucleotides can preferably comprise a "zipper box". Two oligonucleotides may be provided with a zipper box, i.e. a first oligonucleotide comprises a first part of a molecule pair being capable of reversible interaction with a second oligonucleotide comprising the second part of the molecule pair. Typically, the molecule pair comprises nucleic acids, such as two complementary sequences of nucleic acids or nucleic acid analogs. In a certain aspect, the zipper domain polarity of the first oligonucleotide attached to a first chemical entity is reverse compared to the zipper domain polarity of the second oligonucleotide. Usually, the zipping domain is proximal to the chemical entity to allow for a close proximity of the chemical entities. In preferred embodiments, the zipping domain is spaced form the chemical entity with no more than 2 nucleic acid monomers.

Typically, the zipping domain sequence comprises 3 to 20 nucleic acid monomers, such as 4 to 16, and preferably 5 to 10, depending on the conditions used.

In one aspect of the present invention, it is the object to provide a method, including an encoding method, which expands the possible chemical reactions available for producing encoded molecules.

In one aspect there is provided a method for synthesising a bifunctional complex comprising an encoded molecule and an identifier polynucleotide identifying the chemical entities having participated in the synthesis of the encoded molecule, said method comprising the steps of providing
  at least one template comprising one or more codons capable of hybridising to an anti-codon, wherein said template is optionally associated with one or more chemical entities, and
  a plurality of building blocks each comprising an anti-codon associated with one or more chemical entities, and
hybridising the anti-codon of one or more of the provided building blocks to the template,
covalently linking said anti-codons and/or linking the at least one template with the anti-codon of at least one building block, thereby generating an identifier polynucleotide capable of identifying chemical entities having participated in the synthesis of the encoded molecule,
separating the template from one or more of the anti-codons hybridised thereto, thereby generating an at least partly single stranded identifier polynucleotide associated with a plurality of chemical entities,
generating a bifunctional complex comprising an encoded molecule and an identifier polynucleotide identifying the chemical entities having participated in the synthesis of the encoded molecule,
  wherein said encoded molecule is generated by reacting at least two of said plurality of chemical entities associated with the identifier polynucleotide,
  wherein said at least two chemical entities are provided by separate building blocks.

The hybridisation of a first anti-codon to the template can occur sequentially or simultaneously with the hybridisation of a second anti-codon to the template.

The hybridisation of a first anti-codon to the template can also occur sequentially or simultaneously with the linkage of the first anti-codon to a second anti-codon or to the template.

The hybridisation of a first anti-codon to the template can occur sequentially or simultaneously with the linkage of a second anti-codon to a further anti-codon or to the template.

The linkage of a first anti-codon to the template can occur sequentially or simultaneously with the linkage of the first anti-codon to a second anti-codon, and/or the linkage of a first anti-codon to a second anti-codon can occur sequentially or simultaneously with the linkage of the template to the second anti-codon.

In one embodiment, the template is separated from said covalently linked anti-codons by chemically or enzymatically cleaving one or more nucleotide linking bonds of the template. In other embodiments, the template is non-covalently associated with the covalently linked anti-codons.

When the template is separated from said covalently linked anti-codons a separation step is employed, such as e.g. i) a step involving heating the template and the covalently linked anti-codons, thereby displacing the template from the covalently linked anti-codons, and ii) a step involving washing the template and the covalently linked anti-codons in a solvent resulting in displacing the template from the covalently linked anti-codons, wherein said steps are optionally followed by one or more washing steps.

It can be preferred to link at least one of said covalently linked anti-codons to a solid support in a method, wherein the template is hybridised to the covalently linked anti-codons without being covalently linked to said covalently linked anti-codons, and wherein the template is separated from the covalently linked anti-codons by a step involving heating the template and the covalently linked anti-codons and/or a washing step resulting in physically separating the template from the covalently linked anti-codons.

In another embodiment, the template is linked to a member of an affinity pair so that the manipulation of the template can be aided by the binding of the members of the affinity pair.

It is also possible to link the template to a solid support when carrying out a method, wherein said covalently linked anti-codons are hybridised to the template without being covalently linked to said template, and wherein the covalently linked anti-codons are separated from the template by a step involving heating the template and the covalently linked anti-codons and/or a washing step resulting in physically separating the covalently linked anti-codons from the at least one template.

At least one of said covalently linked anti-codons can be further linked to one member of an affinity pair, wherein the other member of said affinity pair is linked to a further solid support, wherein the linkage of said affinity pair members results in attaching said covalently linked anti-codons to said further support, thereby facilitating the separation of template and covalently linked anti-codons.

The identifier polynucleotide can consist exclusively of covalently linked anti-codons and the identifier polynucleotide does not have to comprise the template, or any part thereof.

There is also provided a method wherein the template is at least partly separated from said covalently linked anti-codons by chemically or enzymatically cleaving one or more nucleotide linking bonds of the template. Accordingly, the template or a part thereof can in one embodiment be covalently associated with the covalently linked anti-codons.

In one embodiment, the template is at least partly separated from said covalently linked anti-codons in a separation step selected from i) a step involving heating the template and the covalently linked anti-codons, thereby displacing at least part of the template from the covalently linked anti-codons, and ii) a step involving washing the template and the covalently linked anti-codons in a solvent resulting in displacing at least part of the template from the covalently linked anti-codons, wherein said steps are optionally followed by chemically cleaving or enzymatically cleaving one or more nucleotide linking bonds of the template. The separation of at least part of said at least one template from covalently linked anti-codons hybridised to the template is carried out prior to the reaction of the at least two of said plurality of chemical entities.

A plurality of building blocks can be hybridised to at least one template, such as from 2 to preferably less than 100 building blocks are hybridised to at least one template, such as from 3 to preferably less than 50 building blocks are hybridised to at least one template, for example from 3 to preferably less than 20 building blocks are hybridised to at least one template, such as from 3 to preferably less than 10 building blocks are hybridised to at least one template, for example from 3 to preferably less than 8 building blocks are hybridised to at least one template, such as from 3 to preferably less than 7 building blocks are hybridised to at least one template.

One or more chemical entities of each building block can be reacted. In some embodiments, the reaction of chemical entities involve at least two reactive groups of at least some chemical entities.

In some embodiments there is provided a method as disclosed herein above,
wherein the anti-codon of one of the provided building blocks is hybridised to the template,
wherein the anti-codon is covalently linked to the template,
wherein the anti-codon is displaced from the template, thereby generating an at least essentially single stranded identifier polynucleotide associated with a plurality of chemical entities,
wherein at least two of said plurality of chemical entities associated with the at least essentially single stranded identifier polynucleotide are reacted, thereby generating a bifunctional complex comprising a first encoded molecule and an identifier polynucleotide coding for chemical entities having participated in the synthesis of the first encoded molecule.
The method can comprise the further steps of
hybridising the anti-codon of at least one further building block to the identifier polynucleotide of the first bifunctional complex generated in claim 7, wherein said anti-codon is associated with one or more chemical entities,
covalently linking the anti-codon and the identifier polynucleotide of the first bifunctional complex,
displacing the anti-codon from the identifier polynucleotide of the first bifunctional complex, thereby generating an at least essentially single stranded second identifier polynucleotide associated with the first encoded molecule and one or more chemical entities,
reacting the first encoded molecule and the one or more chemical entities, and
generating a second bifunctional complex comprising a second encoded molecule and the second identifier oligonucleotide identifying the plurality of chemical entities having participated in the synthesis of the second encoded molecule.

The above further steps can be repeated for building blocks comprising different anti-codons and/or different chemical entities, thereby generating a plurality of bifunctional complexes comprising different encoded molecules.

The template can comprise from 2 to preferably less than 100 codons, such as from 2 to preferably less than 10 codons, from 3 to preferably less than 20 codons, such as from 3 to preferably less than 10 codons, for example from 3 to preferably less than 6 codons.

Each codon or anti-codon or building block oligonucleotide preferably comprises or consists of a sequence of nucleotides. The nucleotides can be natural nucleotides or non-natural nucleotides.

Codon or anti-codon or oligonucleotide or polynucleotide as used herein generally refers to linear or branched oligomers of natural or modified monomers or linkages, including deoxyribonucleosides, ribonucleosides, alpha-anomeric forms thereof, polyamide nucleic acids, and the like, capable of hybridising by way of a regular pattern of monomer-to-monomer interactions, such as Watson-Crick type of base pairing, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several hundreds of monomeric units. Whenever an oligonucleotide is represented by a sequence of letters, such "ATGCCTG (SEQ ID NO:19)," it will be understood that the nucleotides are in 5'=>3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilinothioate, phosphoranilidate, phosphoramidate, and the like.

The oligonucleotide moieties of the invention are synthesized by conventional means on a commercially available automated DNA synthesizer, e.g. an Applied Biosystems (Foster City, Calif.) model 380B, 392 or 394 DNA/RNA synthesizer. Phosphoramidite chemistry can be employed, e.g. as disclosed in the following references: Beaucage and Iyer, Tetrahedron, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

Nuclease resistant backbones can be provided. Many types of modified oligonucleotides are available that confer nuclease resistance, e.g. phosphorothioate, phosphorodithioate, phosphoramidate, or the like, described in many references, e.g. phosphorothioates: Stec et al, U.S. Pat. No. 5,151,510; Hirschbein, U.S. Pat. No. 5,166,387; Bergot, U.S. Pat. No. 5,183,885; phosphoramidates: Froehler et al, International application PCT/US90/03138; and for a review of additional applicable chemistries: Uhlmann and Peyman (cited above). In some embodiments it may be desirable to employ P-chiral linkages, in which case the chemistry disclosed by Stec et al European patent application 92301950.9, may be appropriate.

Although each codon or anti-codon or building block oligonucleotide can comprise any suitable number of nucleotides, preferred numbers are from 3 to about 30 nucleotides.

Neighbouring codons can be separated by a framing region, wherein said framing region identifies the position of a codon. The framing regions can have alternating sequences. At least one anti-codon preferably comprises a sequence at least partly complementary to a framing sequence of the template.

The template and/or at least one anti-codon can further comprise one or more priming regions or regions capable of self-hybridisation. The template and/or at least one anti-codon can also comprise one or more flanking regions, wherein said flanking regions optionally comprise a palindromic sequence of nucleotides capable of self-hybridisation, thereby forming a hair-pin loop structure. The template flanking region can be at least partly complementary to the template priming region and allows the formation of a hair-pin loop structure comprising flanking region sequence hybridised to priming region sequence. The template can further comprise two or more PCR priming regions for amplification of the template.

The plurality of building blocks can each comprise an anti-codon covalently linked to one or more chemical entities. At least one of said building blocks can comprise a chemical entity comprising a scaffold moiety comprising a plurality of reactive groups, and/or the template can be linked to a chemical entity comprising a scaffold moiety comprising a plurality of reactive groups. The scaffold moiety reactive groups can react with one or more chemical entities of a single building block, or one or more chemical entities of different building blocks. The chemical entity of at least one building block is thereby transferred to a recipient reactive group of a chemical entity of another building block, or a chemical entity linked to the template, such as a chemical entity comprising a scaffold moiety comprising a plurality of reactive groups.

It may be preferred that one or more of said chemical entities can be selectively cleaved from the anti-codon of the building block, or that at least one chemical entity is simultaneously reacted with a reactive group of a recipient chemical entity and cleaved from the anti-codon to which the chemical entity is associated.

For separation and/or purification purposes, at least one of said chemical entity can advantageously form one member of an affinity pair with another chemical entity. Examples of affinity pairs include biotin and dinitrophenol, and any derivative thereof capable of forming an affinity pair with a binding partner capable of forming said affinity pair with biotin and/or dinitrophenol.

The anti-codon can be protected at the 3' end and/or the 5' end by a protection group, and at least one anti-codon can be attached to a solid support, optionally via such a 3' end protection group or a 5' end protection group. The template and/or the plurality of building blocks can thus remain attached to a solid support during the synthesis of the bifunctional complex, and the bifunctional complex can subsequently remain associated with a solid support or be cleaved therefrom.

The above-mentioned protection group can be photocleavable, such as a group being cleaved by exposure to UV light. Preferably, a phosphate group is formed at the 5' end of an anti-codon following deprotection thereof, thereby converting the anti-codon to a substrate for an enzyme comprising a ligase activity.

Apart from being associated with the oligonucleotide of a building block, one or more chemical entities can also be associated with the template, including covalently linked to the template. Such chemical entities linked to the template preferably comprises a scaffold moiety.

The one anti-codon of at least one building block can be further ligated to an oligonucleotide primer capable of complementing a priming region of the template, and the oligonucleotide primer can in turn be further ligated to, or already covalently attached to, the template, thereby forming a covalent connection between the at least one anti-codon and the template.

In one embodiment, at least one building block, or a subset of said plurality of building blocks, can be provided sequentially and/or sequentially hybridised to the template, wherein said sequentially provided and/or hybridised building block anti-codons are subsequently ligated, wherein chemical entities of said subset of sequentially provided building blocks react before a further subset of building blocks are provided and/or hybridised to the template.

It is also possible for all building block anti-codons to be hybridised to the template simultaneously or in a single batch reaction.

At least some building block anti-codons can be ligated prior to or simultaneously with the reaction of chemical entities. However, building block anti-codons will often be ligated before any of the chemical entities are reacted. In one embodiment, all building block anti-codons are ligated before any of the chemical entities are reacted.

A plurality of building block oligonucleotides can be provided, wherein two or more building block anti-codons, such as 3 building block anti-codons, for example 4 building block anti-codons, such as 5 building block anti-codons, for example 6 building block anti-codons are hybridised to the template and subsequently ligated together to form an anti-codon ligation product. Any subsequently hybridised building block anti-codon is preferably hybridised in a neighbouring position to an already hybridised and optionally ligated anti-codon of a building block, or hybridised in a neighbouring position to an already hybridised and optionally ligated oligonucleotide primer, wherein said already hybridised building block anti-codon or oligonucleotide primer can be ligated to another building block anti-codon or to another oligonucleotide primer or to the template. At least one of said plurality of building block anti-codons is preferably immobilised on a solid support in the form of a beaded polymer.

Some building block anti-codons can be hybridised in a position spaced by one or more nucleotides from another building block anti-codon or oligonucleotide primer, in which case a spacer oligonucleotide is provided and hybridised to the template for joining a building block anti-codon with a neighbouring building block anti-codon, or for joining a building block anti-codon with a neighbouring oligonucleotide primer.

Neighbouring building block anti-codons can be ligated by chemical ligation or by enzymatic ligation, thereby covalently linking said neighbouring building block anti-codons.

When the building block anti-codons are linked by chemical ligation, the anti-codons are preferably selected from the group consisting of first anticodons comprising a 3'-OH group and second anticodons comprising a 5'phosphor-2-methylimidazole group, which groups are reacted to form a phosphodiester internucleoside linkage, first anticodons comprising a phosphoimidazolide group at the 3'-end and a phosphoimidazolide group at the 5'-end, which groups are reacted to form a phosphodiester internucleoside linkage, first anticodons comprising a 3'-phosphorothioate group and second anticodons comprising a 5'-iodine group, which groups are reacted to form the internucleoside linkage 3'-O—P(=O)(OH)—S-5', and first anticodons comprising a 3'-phosphorothioate group and second anticodons comprising a 5'-tosylate, which groups are reacted to form the internucleoside linkage 3'-O—P(=O)(OH)—S-5'.

At least some building block anti-codons can be ligated to the anti-codon of a neighbouring building block and/or to a template by a ligase, thereby covalently linking said building block anti-codons. The ligase can be selected from the group consisting of DNA ligase and RNA ligase, and the DNA ligase can be selected from the group consisting of Taq DNA ligase, T4 DNA ligase, T7 DNA ligase, and *E. coli* DNA ligase.

As stated herein above, an at least essentially single stranded identifier polynucleotide is obtained by displacing or separating codons and anti-codons under denaturing conditions resulting in said displacement. The denaturing conditions can be obtained by performing the displacement in a media selected from organic solvents, aprotic solvents, acidic solvents, media comprising denaturants, and alkaline solvents. The denaturing conditions can be e.g. heating the hybridised and covalently linked codons and anti-codons to a temperature above the melting temperature of the duplex portion of the molecule, wherein said heating results in said displacement or separation.

It is also possible to degrade the template part of the identifier polynucleotide before any of the chemical entities are reacted. When the template is an RNA template, the template can be degraded by using an enzyme selected from RNAseH, RNAseA and RNAse 1, by choosing weak alkaline conditions (pH 9-10), or by using aqueous $Pb(Ac)_2$. When the template is a DNA template comprising an internucleoside linker comprising a thiophospate, the template can be treated with aqueous iodine. When the template is a DNA template comprising an uracil nucleobase, the template can be treated with uracilglycosylase and subsequently with weak acid.

Accordingly, it is possible in a number of ways to separate and/or degrade the template from a plurality of covalently linked anti-codons before reacting any chemical entities, subsequently reacting the chemical entities, and generating a bifunctional complex comprising an encoded molecule and an identifier oligonucleotide consisting solely of ligated anti-codons, wherein said identifier oligonucleotide identifies the chemical entities having participated in the synthesis of the encoded molecule.

The template can e.g. be removed by cleaving at least one covalent link linking template codons and building block anti-codons, and subjecting to cleavage product to conditions eliminating hybridisation between template codons and building block anti-codons, and separating, including physically separating the template from the covalently linked anti-codons. The physical separation can be achieved e.g. by removing the template from the compartment comprising the covalently linked anti-codons. The covalent link can e.g. be cleaved by a restriction endonuclease. The separation of a template from building block anti-codons can be further aided by using templates comprising a first binding partner of an affinity pair, and wherein a second binding partner is optionally associated with a solid support, wherein said first and second binding partners constituted an affinity pair, reacting said first and second binding partners, and separating the template from said anti-codons.

It is also possible that at least one of said building blocks can comprise a first binding partner of an affinity pair, and wherein the second binding partner is optionally associated with a solid support, wherein said first and second binding partners constituted an affinity pair. When templates and anticodons are separated, different affinity pairs are used for the templates and for the anti-codons.

In one embodiment, codons and anti-codons are separated by hybridising a nucleic acid to e.g. the template part of an identifier polynucleotide, thereby generating a duplex comprising the template. The duplex can be provided by competition hybridisation by initially annealing a primer oligonucleotide to the template and extending said primer over the extent of the template using a polymerase.

Many different reactions can be performed when reacting chemical entities on different building blocks. Examples include reactions resulting in the formation of the following chemical bonds: peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

Examples of bonds include e.g. —NHN(R)CO—; —NHB(R)CO—; —NHC(RR')CO—; —NHC(=CHR)CO—; —NHC$_6$H$_4$CO—; —NHCH$_2$CHRCO—; —NHCHRCH$_2$CO—; —COCH$_2$—; —COS—; —CONR—; —COO—; —CSNH—; —CH$_2$NH—; —CH$_2$CH$_2$—; —CH$_2$S—; —CH$_2$SO—; —CH$_2$SO$_2$—; —CH(CH$_3$)S—; —CH=CH—; —NHCO—; —NH-CONH—; —CONHO—; —C(=CH$_2$)CH$_2$—; —PO$_2^-$NH—; —PO$_2^-$CH$_2$—; —PO$_2^-$CH$_2$N$^+$—; —SO$_2$NH$^-$—; and lactams, including any combination thereof.

At least one chemical entity reaction is preferably an acylation reaction. Also, at least one chemical entity preferably comprises an amine, wherein an amide bond is formed when said at least one chemical entitiy is reacted.

Both polymers and scaffolded molecules can be synthesised. Examples of scaffolds for small molecule synthesis are disclosed e.g. in U.S. Pat. No. 5,646,285, U.S. Pat. No. 5,756,291, U.S. Pat. No. 5,840,485, U.S. Pat. No. 6,037,340, U.S. Pat. No. 6,191,273, U.S. Pat. No. 6,194,612, U.S. Pat. No. 6,207,861, Accordingly, different libraries of e.g. synthetic test compounds can be provided, such as e.g.:

libraries in which the synthetic test compound are polyamides, i.e., the synthetic test compound are chains of 2-100 amino acids linked through amide bonds;

libraries in which the synthetic test compound are polyesters, i.e., chains of 2-100 hydroxy acids linked by ester bonds;

libraries in which the synthetic test compound are polyethers, i.e., chains of 2-100 hydroxy alcohols linked by ether bonds;

libraries in which the synthetic test compound are polyureas;

libraries in which the synthetic test compound are polyurethanes;

libraries in which the synthetic test compound are polycarbonates;

libraries in which the synthetic test compound are polyamines;

libraries in which the synthetic test compound are polyalkanes, polyalkenes, or polyalcohols, including halo derivatives thereof;

libraries in which the synthetic test compound are polysulfides;

libraries in which the synthetic test compound are polydisulfides;

libraries in which the synthetic test compound are polymers whose structures contain randomly arranged segments from two or more of the polymeric structures described in the embodiments above;

libraries in which the synthetic test compound are derivatives of a steroid structure;

libraries in which the synthetic test compound are derivatives of a sugar such as .beta.-D-glucose;

libraries in which the synthetic test compound are derivatives of a heterocyclic structure, such as benzodiazepine;

libraries in which the synthetic test compound are derivatives of a structure capable of serving a scaffolding onto which multiplicity of structures such as but not limited to carboxylic acids, amines, and halogen derivatives can be attached in a defined way;

libraries in which the molecules are chimeric structures containing one or more sequences of variable length linked by chemistry selected from one or more of the following: amides, esters, ethers, carbonates, sulfides, disulfides, alkenes, and amines, and one or more structures capable of acting as a scaffolding, such as a steroid, a sugar, an aromatic or polyaromatic structure.

Table 15 U.S. Pat. No. 5,840,485 discloses sutable scaffolds, reactive groups and reaction chemistry:

| Scaffold No. | Subunits | Chemistry of Coupling |
|---|---|---|
| 1. Amino Acid Aldehyde/ Organo-metal | amino acid homoserine aldehyde alkyl- or arylmetal | CO—NH coupling C—C bond formation |
| 2. Diketo- piperazine | amino acids N-alkyl amino acids | CO—NH coupling reductive amination |
| 3. Substituted Thioproline | amino acids cysteine amino acid aldehyde alkyl or aryl acids | CO—NH coupling reductive amination |
| 4. Substituted Triazine | amino acids trichlorotriazine alkyl or aryl amines | CO—NH coupling reductive amination |
| 5. Substituted Thioproline Dioxide | amino acids N-alkyl amino acids cysteine aldehyde, ketone | CO—NH coupling thioaminal formation oxidation C-alkylation |
| 6. Acylated Polyethylene- Diamine | amino acids glycinal alkyl or aryl acids | CO—NH coupling reductive amination |
| 7. Benzene- tricarboxylic Acid | amino acids N-alkyl amino acids 1,2,4-benzenetri- carboxylic acid | CO—NH coupling |
| 8. 2-S-alkyl (aryl) isoindol | subst. phthalic anhydride alkyl or aryl amines alkyl or aryl mercaptanes | isoindol synthesis |
| 9. Cyclopentane | N-alkyl amino acids prim. or sec. amines cyclopentantri- carboxylic acid | CO—NH coupling |
| 10. Diacyldialkyl Diamino Acid | amino acids aldehydes alkyl or aryl acids | CO—NH coupling reductive amination |
| 11. Extended Kemps Triacid | amino acids Kemp's triacid protected diamines | CO—NH coupling |
| 12. Kemps Triacid | amino acids Kemp's triacid alkyl or aryl acids | CO—NH coupling |
| 13. Akyl Acyl Amino Acid | amino acids aldehydes alkyl or aryl acids | CO—NH coupling |
| 14. Diaminobenzoic Acid | amino acids 3,5-diaminobenzoic acid alkyl or aryl acids | CO—NH coupling |
| 15. Steroid | steroid skeleton aldehydes | reductive amination CO—NH coupling |
| 16. Bis- Iminodiacetic Acid | glycine t-butylbromoacetate alkyl or aryl amines | |
| 17. N-alkylated Iminodtacetic Acid | diaminobutanoic acid t-butylbromoacetate alkyl or aryl amines | CO—NH coupling N-alkylation |
| 18. $\alpha, \beta, \gamma$ Peptidomimetic | diaminoacids alkyl or aryl acids | CO—NH coupling |
| 19. N-Substituted Glycine Peptidomimetic | amino acids aldehydes | CO—NH coupling reductive amination |

Further examples of reaction chemisty are disclosed in the examples of WO 02/103008.

The encoded molecule can be associated with the identifier oligonucleotide through a single bond. The method can also comprise the further step of cleaving the encoded molecule from the identifier polunucleotide of a bifunctional complex.

It is possible to repeat method steps one or more times for building blocks comprising different anti-codons and/or different chemical entities, wherein said building block anti-codons hybridise to codons not already hybridised to an anti-codon in a previous synthesis round. In this way, there is provided a method for generating a library of different bifunctional complexes, said method comprising the steps of repeating individual method steps and using a different combination of building blocks and templates for each repetition.

Accordingly, it is possible to generate a plurality of bifunctional complexes from the hybridisation of a plurality of templates to a plurality of building block anti-codons, covalently linking anti-codons hybridised to the same template, separating the template from at least some of the covalently linked anti-codons, preferably by degrading the template or by cleaving at least one chemical bond linking the template to the covalently ligated anti-codons followed by physical separation of the template and the covalently linked anti-codons, reacting the chemical entities and generating a library of bifunctional complexes each comprising a different encoded molecule and an identifier polynucleotide identifying the chemical entities having participated in the synthesis of the encoded molecule, wherein each of the plurality of encoded molecules are generated by reacting chemical entities associated with different anti-codons.

Pools each comprising a plurality of building blocks directed to each codon of the plurality of templates can be added sequentially, and different anti-codons in each pool can have an identical flanking sequence.

There is also provided the further steps of subjecting a library of bifunctional complexes to a partitioning procedure, such as an enrichment procedure and/or a selection procedure resulting in the enrichment and/or selection of bifunctional complexes displaying at least one desirable property. The enrichment procedure and/or selection procedure can comprise the step of subjecting the library of bifunctional complexes to a molecular target, and selecting bifunctional complexes binding to said molecular target. However, the enrichment procedure and/or selection procedure can also employ an assay generating for each bifunctional complex a result allowing a partitioning of the plurality of bifunctional complexes.

The molecular target can be immobilized on a solid support and form a stable or quasi-stable dispersion. The molecular target can comprise a polypeptide, such as a polypeptide is selected from the group consisting of kinases, proteases, phosphatases. The molecular target can also comprise an anti-body or a nucleic acid such as a DNA aptamer or an RNA aptamer. The target polypeptide can be attached to a nucleic acid having templated the synthesis of the polypeptide.

It is possible in accordance with the methods of the invention to obtain an identifier polynucleotide part of a bifunctional complex from a plurality of said partitioned bifunctional complexes, optionally by separating the identifier polynucleotide from the encoded molecule of the bifunctional complex, and optionally in a the further step amplifying, in one or more rounds, said plurality of identifier polynucleotides by a linear amplification method or by an exponential amplification method, thereby generating a heterogeneous population of duplex molecules each comprising complementary identifier oligonucleotides identifying the chemical entities having participated in the synthesis of the encoded molecule of a bifunctional complex, wherein the identifier oligonucleotide is selected from the group consisting of identifier oligonucleotides comprising the template, or a part thereof, covalently linked to the covalently linked anti-codons, and identifier oligonucleotides comprising only covalently linked anti-codons and no template, or part thereof.

There is also provided the further step of converting said identifier polynucleotides into duplex molecules each comprising complementary identifier oligonucleotides identifying the chemical entities having participated in the synthesis of the encoded molecule of a bifunctional complex. The template part of the identifier oligonucleotide can be separated from the encoded molecule prior to amplification.

In a still further step, partitioned complementary identifier oligonucleotides are separated, thereby generating a population of heterogeneous identifier oligonucleotides, and reannealing said separated identifier oligonucleotides under conditions where homo-duplexes and hetero-duplexes are formed, wherein homo-duplexes comprises identifier oligonucleotides originating from identical bifunctional complexes, and wherein hetero-duplexes comprises identifier oligonucleotides originating from different bifunctional complexes, such as bifunctional complexes comprising different encoded molecules. The steps of identifier oligonucleotide displacement and reannealing can be repeated at least once.

Homo-duplexes and hetero-duplexes can be separated by a chemical or enzymatical separation methods, or by physical separation methods. Homo-duplexes can e.g. be isolated by removal of hetero-duplexes, and hetero-duplexes can be removed by enzymatic degradation by using an enzyme comprising a nuclease activity, such as e.g. T4 endonuclease VII, T4 endonuclease I, CEL I, nuclease S1, or variants thereof. The enzyme can be thermostable.

Remaining homo-duplexes can be amplified prior to decoding the identity of the encoded molecule of a bifunctional complex. Identifier oligonucleotides can be recovered from the selection procedure and reused for a second or further round synthesis of encoded molecules.

The generated library can comprise 1,000 or more different members, such as $10^5$ different members, for example $10^6$ different members, such as $10^7$ different members, for example $10^8$ different members, such as $10^9$ different members, for example $10^{10}$ different members, such as $10^{12}$ different members.

According to one embodiment there is provided a method,
wherein the anti-codons of from 3 to 8 building blocks are hybridised to a template sequentially or simultaneously in the same first compartment,
wherein at least one of the building blocks comprise a scaffold moiety comprising a plurality of reactive groups associated to an anti-codon,
wherein the template is covalently bound to a solid support, such as a beaded polymer,
wherein the covalently linked anti-codons are separated from the template covalently bound to the solid support, wherein said separation results in anti-codons and codons not being hybridised to each other,
optionally transferring the covalently ligated anti-codons to a second compartment, or transferring the template covalently bound to a solid support to a second compartment, and
reacting the chemical entities associated with the identifier polynucleotide, optionally in a compartment different from the compartment harbouring the template.

In another preferred embodiment there is provided a method
wherein the anti-codons of from 3 to 8 building blocks are hybridised to a template sequentially or simultaneously in the same first compartment,
wherein at least one of the building blocks comprise a scaffold moiety comprising a plurality of reactive groups associated with an anti-codon,
wherein the covalently linked anti-codons are initially covalently linked to the template,
wherein the template part of the identifier oligonucleotide is degraded, thereby generating an identifier oligonucleotide comprising an essentially single stranded molecule comprising no template sequence,
optionally transferring the covalently ligated anti-codons to a second compartment, and
reacting the chemical entities associated with the identifier polynucleotide.

In the above preferred embodiment, the building blocks can be provided sequentially, and the method can comprise the further steps of
i. covalently linking the anti-codon of a sequentially added building block to the template, or covalently linking the anti-codon of a sequentially added building block to an anti-codon covalently linked to the template,
ii. selecting a set of reaction conditions wherein codons and anti-codons do not hybridise to each other, thereby generating an essentially single stranded molecule,
iii. reacting a chemical entity of a sequentially added building block with a chemical entity associated with the template, or with a chemical entity associated with an anti-codon covalently linked to the template, and
repeating steps i) to iii) for different building blocks.

In another aspect of the present invention no templates are used. In accordance with this aspect, there is provided a method for synthesising one or more bifunctional complexes each comprising a molecule resulting from the reaction of a plurality of chemical entities and an identifier polynucleotide identifying one or more of the chemical entities having participated in the synthesis of the molecule, said method comprising the steps of providing a plurality of building blocks each comprising an oligonucleotide associated with one or more chemical entities, providing at least one connector oligonucleotide capable of hybridising with one or more building block oligonucleotides, immobilising at least one building block to a solid support, hybridising said immobilized building block oligonucleotide to a first connector oligonucleotide, hybridising at least one additional building block oligonucleotide to said first connector oligonucleotide, ligating building block oligonucleotides hybridised to the connector oligonucleotide, separating the connector polynucleotide from the ligated building block oligonucleotides, reacting one or more chemical entities associated with different building block oligonucleotides, thereby obtaining a first bifunctional complex comprising a first molecule or first molecule precursor linked to a first identifier oligonucleotide identifying the chemical entities having participated in the synthesis of the molecule or molecule precursor, wherein said first bifunctional complex is immobilised to a solid support.

The above chemical entities can be reacted in a reaction compartment from which the connector oligonucleotide has been removed in a washing and/or separation step prior to the reaction of said chemical entities.

The method can comprise the further steps of
i. providing a second connector polynucleotide,
ii. hybridising said second connector polynucleotide to the identifier polynucleotide of said first bifunctional complex,
iii. hybridising at least one further oligonucleotide of a building block to said second connector oligonucleotide,
iv. ligating building block oligonucleotides hybridised to the second connector oligonucleotide, wherein at least one of said building block oligonucleotides are hybridised to the first identifier polynucleotide,
v. separating the second connector polynucleotide from the ligated building block oligonucleotides, for example by diverting the second connector polynucleotide to another compartment,
vi. reacting the first molecule precursor with the one or more chemical entities associated with the ligated building block oligonucleotide(s), thereby obtaining a second bifunctional complex comprising a molecule or molecule precursor linked to a second identifier polynucleotide identifying the chemical entities having participated in the synthesis of the molecule or molecule precursor, wherein said second bifunctional complex is immobilised to a solid support.

Steps i) to vi) can be repeated for different connector oligonucleotides and different further building blocks, thereby generating different molecules or molecule precursors.

The bifunctional complex or a plurality of such complexes can subsequently be released from the solid support.

In accordance with the above aspect of the invention there is provided a method, wherein different bifunctional complexes are generated in different reaction compartment, and wherein at least some of said different bifunctional complexes are combined in a reaction compartment comprising a plurality of further connector oligonucleotides, wherein at least two of said different bifunctional complexes hybridise to a further connector polynucleotide, wherein the molecule precursor part of said complexes react, thereby generating a further molecule in the form of a reaction product, wherein the identifier polynucleotides of said bifunctional complexes are optionally covalently linked prior to or after the reaction of the molecule precursors, wherein the covalently linked identifier polynucleotides are optionally separated from the further connector oligonucleotide prior to or after reaction of said molecule precursors.

In yet another aspect of the invention there is provided a method for synthesising a bifunctional complex comprising a molecule resulting from the reaction of a plurality of chemical entities, wherein said molecule is linked to an identifier polynucleotide identifying one or more of the chemical entities having participated in the synthesis of the molecule, said method comprising the steps of providing a plurality of building blocks selected from the group consisting of
  building blocks comprising an identifier oligonucleotide linked to one or more chemical entities,
  building blocks comprising an identifier oligonucleotide linked to one or more reactive groups, and
  building blocks comprising an identifier oligonucleotide comprising a spacer region, wherein said building blocks comprising a spacer region are preferably connector polynucleotides to which complementary connector polynucleotides of building blocks of groups a) and b) can hybridise, generating a hybridisation complex comprising at least n building blocks by hybridising the identifier oligonucleotide of one building block to the identifier oligonucleotide of at least one other building block,
  wherein n is an integer of 4 or more
  wherein at least 3 of said at least n building blocks comprise a chemical entity,
  wherein no single identifier oligonucleotide is hybridised to all of the remaining identifier oligonucleotides,
  wherein optionally at least one of said building blocks of group c) is immobilised to a solid support, thereby providing a handle to which an oligonucleotide of at least one building block of groups a) or b) can hybridise,
  covalently linking identifier oligonucleotides of building blocks comprising one or more chemical entities, thereby obtaining an identifier polynucleotide comprising covalently linked identifier oligonucleotides each associated with one or more chemical entities,
  optionally separating said identifier polynucleotide obtained in step iv) from any immobilised connector oligonucleotides hybridied thereto, wherein said separation optionally comprises the step of diverting said identifier polynucleotide comprising covalently linked identifier oligonucleotides each associated with one or more chemical entities to a different reaction compartment, thereby separating said identifier polynucleotide from said immobilised connector oligonucleotides
  reacting said at least 3 chemical entities linked to the identifier polynucleotide, and
  obtaining a bifunctional complex comprising a molecule resulting from the reaction of a plurality of chemical entities, wherein said molecule is linked to an identifier polynucleotide identifying one or more of the chemical entities having participated in the synthesis of the molecule.

In the above method a plurality of different bifunctional complexes can be obtained by repeating the method steps for different building blocks.

The method can involve reacting at least 3 chemical entities, such as at least 4 chemical entities, for example at least 5 chemical entities, such as at least 6 chemical entities, for example at least 8 chemical entities, such s reacting at least 10 chemical entities.

Accordingly, there is provided a method
wherein a plurality of molecules are synthesised,
wherein the plurality of synthesised molecules are selected from the group consisting of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopolypeptides, polyamides, vinylogous sulfonamide peptides, polysulfonamides, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, polythioethers, polyethylene glycols (PEG), polyethylenes, polydisulfides, polyarylene sulfides, polynucleotides, PNAs, LNAs, morpholinos, oligo pyrrolinones, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, including any combination thereof,
wherein each molecule is synthesised by reacting a plurality of chemical entities preferably in the range of from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

The molecule can be a small molecule generated by reaction of a plurality of chemical entities, wherein said chemical entities can be linked by one or more chemical bonds selected from the group consisting of chemical bonds such as peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

The chemical bonds linking reacted chemical entities can also be illustrated as: —NHN(R)CO—; —NHB(R)CO—; —NHC(RR')CO—; —NHC(=CHR)CO—; —NHC$_6$H$_4$CO—; —NHCH$_2$CHRCO—; —NHCHRCH$_2$CO—; —COCH$_2$—; —COS—; —CONR—; —COO—; —CSNH—; —CH$_2$NH—; —CH$_2$CH$_2$—; —CH$_2$S—; —CH$_2$SO—; —CH$_2$SO$_2$—; —CH(CH$_3$)S—; —CH=CH—; —NHCO—; —NHCONH—; —CONHO—; —C(=CH$_2$)CH$_2$—; —PO$_2^-$NH—; —PO$_2^-$CH$_2$—; —PO$_2^-$CH$_2$N$^+$—; —SO$_2$NH$^-$—; and lactams, including any combination thereof.

The method results in the synthesis of more than or about $10^3$ different molecules, such as more than or about $10^4$ different molecules, for example more than or about $10^5$ different molecules, such as more than or about $10^6$ different molecules, for example more than or about $10^7$ different molecules, such as more than or about $10^8$ different molecules, for example more than or about $10^9$ different molecules, such as more than or about $10^{10}$ different molecules, for example more than or about $10^{11}$ different molecules, such as more than or about $10^{12}$ different molecules, for example more than or about $10^{13}$ different molecules, such as more than or about $10^{14}$ different molecules, for example more than or about $10^{15}$ different molecules, such as more than or about $10^{16}$ different molecules, for example more than or about $10^{17}$ different molecules, such as more than or about $10^{18}$ different molecules.

The above-mentioned embodiment wherein there is provided a plurality of building blocks selected from the group consisting of building blocks comprising an identifier oligonucleotide linked to one or more chemical entities, building blocks comprising an identifier oligonucleotide linked to one or more reactive groups, and building blocks comprising an identifier oligonucleotide comprising a spacer region, wherein said building blocks comprising a spacer region are preferably connector polynucleotides (CPNs) to which complementary connector polynucleotides (CCPNs) of building blocks of groups a) and b) can hybridise, is further illustrated in the following section.

The methods of this embodiment of the present invention allows molecules to be formed through the reaction of a plurality of reactants, such as e.g. chemical entities. The present embodiment describes the use of connector polynucleotides (CPN's) to bring chemical entities in proximity, whereby such reeactions are made possible, leading to the synthesis of molecules such as e.g. small molecules and polymers.

In the present invention, the individual chemical moieties/chemical entities may be carried by oligonucleotides (CCPN's) capable of annealing to said CPN's. The combination and reaction of chemical entity reactive groups carried by such complementary connectors polynucleotides, will lead to formation of molecules via complexation to CPN's.

Each CPN may bring two or more CCPN's in proximity, whereby reactions between functional groups on these CCPN's are made more likely to occur. Chemical entity reactive groups/reactive moieties/functional groups may be activated scaffolds or activated substituent like moieties etc. Some CCPN's only anneal to one CPN other CCPN's may anneal to two CPN's. In one embodiment of the present invention, a CCPN anneals to a CPN, which CPN allows the annealing of one further CCPN. This second CCPN may then allow the annealing of a second CPN, which may allow annealing of further CCPN's and so forth. Hybridization of multiple CCPN's and CPN's may be either sequentially or simultaneously in either one or multiple tubes. As such all CCPN's and CPN's may be added at once. Alternatively, they may be added sequentially, i.e. e.g. first a set of CPN's, then a set of CCPN's followed by a new set of CPN's or visa versa. In this sequential setting a handling control of CCPN/CPN-complex selfassembly is achieved. In another embodiment, a set of CCPN's forms complexes $A^1$-$A''$ with a set of CPN's in one separate compartment e.g. a tube. In other compartments, other sets of CCPN's forms complexes $B^1$-$B''$ with a set of CPN's etc. These separately formed complexes may be combined and form further new complexes, either directly or through further addition of CCPN's or CPN's. This illustrates still another way of a handling control of CCPN/CPN-complex selfassembly.

The present invention may be used in the formation of a library of compounds. Each member of the library is assembled by the use of a number of CCPN's, which number may be the same or different for different molecules. This will allow the formation of a mixed library of molecules assembled from 2 to n chemical moieties/fragments/chemical entitiesor parts thereof.

If such a library, e.g. contains molecules assembled from e.g. 1-7 functional entities/chemical moieties and 100 different chemical entity/moiety types exists, the library would theoretically be a mixture of more than $100^7$ molecules. See FIG. 3.

In one setting, a CCPN may specify for the annealing of a specific type of CPN, a CPN which will specify the annealing of a further specific second CCPN, which chemical entity reactive groups are capable of reacting with the chemical entity reactive groups of CCPN one. In this setting each CCPN will therefore specify, which CCPN it interacts with via the CPN sequence, i.e. which reaction partner(s) they accept/prefer.

Some CCPN's carrying scaffolds may contain a certain set of functional groups. Other CCPN's carry scaffolds with another set of functional groups and still, each scaffold carrying CCPN may be combined with other CCPN's, which chemical entity reactive groups can react with exactly that scaffold in the presence of a number of other types of CCPN's, including e.g. CCPN's which could have reacted but were not allowed to react. Further details are described below. This control of correct/accepted combinations of chemical entity reactive groups will allow the formation of a mixed library of highly branched, semi-branched and linear molecules.

The CCPN cross talk may also be used to control the properties of library members. E.g. CCPN's carrying large chemical entities may only call for CCPN's carrying small chemical entities or CCPN's carrying hydrophilic entities may call for CCPN's carrying hydrophilic chemical entities or lipophilic chemical entities depending on design.

As the chemistries applicable, will be increased by the fact, that CCPN's themselves ensure correct/accepted chemical entity reaction partners, a much higher number of scaffolds will become easily available and may co-exist. E.g., it may be that derivatization of one scaffold can only be performed through the use of one specific set of transformation, whereas another scaffold may need another set of transformations. Different reactions and different CCPN's will therefore be needed for derivatization of each of these scaffolds. This is made possible by the present invention. See further details below.

As the total number of theoretically synthesizable molecules may exceed the number of actually synthesized molecules, which can be present in a given tube, shuffling becomes important to ensure a maximum of tested CCPN combinations. If e.g. $10^{17}$ is considered as a potential maximum number of different molecules present in a given reaction tube, then by using 1.000 different CCPN's and allowing formation of molecules assembled from the chemical entities of 6 CCPN's, this number will be exceeded. Selection ensures that appropriate CPN's will survive, and shuffling will ensure that the number of combinations tested will be maximized.

In one embodiment of the present invention, a CPN-sequence is designed so as to anneal to one specific CCPN-sequence. This gives a one-to-one relationship between the chemical entity descriptor (e.g. a polynucleotide based codon) and encoded chemical entity. However, the same effect, a specific chemical entity is encoded by specific CPNs and CCPNs, can be obtained by having a set of CPN-sequences that anneal to a set of CCPN-sequences. This would then require that identical chemical entities are carried by all the CPNs or CCPNs of a set.

This kind of "codon-randomization" is sometimes advantageous, for example when CPN-sequences and CCPN-sequences are designed so as to allow an expansion of the library size at a later stage. If the coding region of e.g. a CPN is 3 nucleotides (providing 64 different codons), but only 16 different chemical entities have been prepared, then the CCPNs may be grouped into 16 groups, for example where the first of the three nucleotide positions is randomized (i.e. 4 different CCPN-sequences carry the same functional entity). A pseudo-one-to-one relationship is thus preserved, since the identity of the encoded chemical entity can be unambiguously identified by identification of the CPN (or CCPN) involved.

Sometimes scrambling, i.e. one CPN or CCPN sequence specifying more than one chemical entity, is advantageous. Likewise, under certain conditions it is advantageous to have one CPN or CCPN specify more than one chemical entity. This will, however, not lead to a one-to-one or a pseudo-one-to-one relationship. But may be advantageous, for example in cases where the recovered (isolated) entity from a selection can be identified through characterization of for example its mass (rather than its attached polynucleotide complex), as this will sample a larger chemistry space.

The present invention in a still further aspect discloses a method for synthesising a bifunctional complex comprising an encoded molecule and a template coding for one or more chemical entities which have participated in the synthesis of the encoded molecule, the method comprising the steps of
i) providing a) a template comprising one or more codons, b) one or more building blocks having an anticodon associated with a chemical entity, and c) a nucleic acid sequence associated with a reactive site,
ii) contacting the tempate with the one or more building blocks under conditions allowing for hybridisation between codons and anticodons,
iii) ligating at least one anticodon of a building block to the nucleic acid sequence associated with the reactive site, and
iv) reacting the chemical entity of the ligated building block with the reactive site under conditions where the ligation product is single stranded, to obtain a template-encoded reaction product.

The media for performing a reaction product is of crucial importance for the progress of the chemical reaction. As an example, many chemical reactions cannot be effectively conducted in aqueous solvents because the reactants are not sufficient soluble. Moreover, when nucleic acids are present, a lipophilic reactant may prefer, in an aqueous solvent, to be located in or in the vicinity of the double helix and therefore not accessible for another reactant dissolvable in the solvent. The present invention provide a solution to this problem by allowing a covalent link between the chemical entity and the reactive site to be reacted with the chemical entity, thereby allowing non-hybridising conditions to be present during the reaction. The upper limit for the conditions applied during the reaction may be the degradation of the nucleic acids. However, nucleic acids are stable molecules withstanding high temperatures, extreme pH, most organic solvents etc.

Numerous chemical reactions are compatible with DNA chemistry. However, only a limited number of such reactions are compatible with the presence of a DNA duplex formed between the anticodon of a building block and the template. In an aspect of this invention, the separation of conditions for performing the genetic information exchange step and the chemical reaction step ensure that many additional chemical reactions which are not compatible with a DNA duplex is accessible to the experimenter. In addition, this technology has the potential of increasing the speed, specificity and cost-efficiency of template programmed chemical reactions.

As acknowledged by those skilled in the art a plethora of means exist for the denaturation of DNA duplexes or the removal of a single strand of a duplex such as heat, alkali or acid, denaturant such as urea, formamide, GdHCl, ethanol, isopropanol, methanol, hygroscopic and/or organic solvents or any combinations of the above as well as nucleases or molecular handles enabling the specific removal or partial removal of a template strand(s).

Generally, the template comprises one or more codons. A single codon may be sufficient when the template or a nucleic acid hybridised to the template comprises a reactive site. Usually, the template comprises more than one codon to allow for a sufficient diverse encoded molecule. In a preferred aspect of the invention the template comprises 2-100 codons. Templates comprising more than 100 codons may be used but is generally not necessary to afford the desired diversity of a library of complexes. In a preferred aspect of the invention the template comprises 3-20 codons.

The codon is a recognition unit that can be recognized by an anticodon. A variety of different kinds of recognition units exist in nature. Examples are antibodies which are recognized by an epitope, proteins which are recognized by another protein, mRNA which recognizes a protein, and oligonucleotides which recognize complementing oligonucleotide sequences. In certain aspects of the present invention a codon is a sequence of nucleotides. Generally the codon has the ability to interact with an anticodon in a specific manner, which allow for a specific recognition between a particular codon and anticodon pair. The specific pairing makes it possible to decode the template in order to establish the synthetic history of an encoded molecule. When the template comprises more than one codon, each member of a pool of building blocks can be identified uniquely and the order of the codons is informative of the synthesis step each member has been incorporated in.

The sequence of the nucleotides in each codon may have any suitable length. Generally it is preferred that each codon comprises two or more nucleotides. In certain aspects of invention each coding comprises 3 to 30 nucleotides, preferably 5 to 10 nucleotides.

The template will in general have at least two codons which are arranged in sequence, i.e. next to each other. Two neighbouring codons may be separated by a framing sequence. Depending on the encoded molecule formed, the template may comprise further codons, such as 3, 4, 5, or more codons, as indicated above. Each of the further codons may be separated by a suitable framing sequence. Preferably, all or at least a majority of the codons of the template are arranged in sequence and each of the codons is separated from a neighbouring codon by a framing sequence. The framing sequence may have any appropriate number of nucleotides, e.g. 1 to 20. Alternatively, codons on the template may be designed with overlapping sequences.

The framing sequence may serve various purposes. In one setup of the invention, the framing sequence identifies the position of a codon. Usually, the framing sequence either upstream or downstream of a codon comprises information which allows determination of the position of the codon. In another setup of the invention, the frames have alternating sequences, allowing for additions of building blocks from two pools in the formation of a library.

The framing sequence may also or in addition provide for a region of high affinity. The high affinity region may ensure that the hybridisation of the template with the anti-codon will occur in frame. Moreover, the framing sequence may adjust the annealing temperature to a desired level.

A framing sequence with high affinity can be provided by incorporation of one or more nucleobases forming three hydrogen bonds to a cognate nucleobase. An example of a nucleobase having this property is guanine and cytosine. Alternatively, or in addition, the spacer sequence may be subjected to back bone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The template may further comprise a priming region for initiating the ligation process. The priming region allows for a ligation primer to hybridize to the template using appropriate conditions. Suitably, the ligation primer is a nucleic acid sequence which may or may not be associated with a reactive site. In addition to one or more codons the template may comprise a flanking region. The flanking region can encompasses a signal group, such a flourophor or a radio active group, to allow a direct detection of the presence of the complex or a label that may be detected, such as biotin. When the template comprises a biotin moiety, a hybridisation event can be observed by adding stained streptavidine, such as streptavidine-phycoerythrin conjugate. In a particular embodiment, the flanking regions are present on each side of the coding sequences providing for an amplification reaction, such as PCR.

In a certain aspect of the invention the flanking region is complementary to the priming region allowing for a hairpin loop to be formed when suitable hybridisation conditions is present. Suitably, no coding regions are present between the flanking region and the priming region. The use of a hairpin loop allows for covalent attachment of the nascent encoded molecule to the template that has encoded the synthesis of said molecule. In a certain aspect of the present invention, the duplex formed by the flanking region and the priming region is recognized by a restriction enzyme as substrate. The cleavage of the double helix allows for the separation of the ligation product and the template.

The one or more building blocks used in accordance with the present invention comprise an anticodon and a chemical entity. The anticodon and the chemical entity can be associated by a direct or indirect covalent or non-covalent interaction. Suitably, the anticodon is covalently connected to the chemical entity, optionally through a suitable linker.

The chemical entities can generally be divided into three groups. A first group of chemical entities comprises scaffold molecules. A scaffold molecule may be a single reactive group or a chemical core structure, like a steroid, to be modified. Generally the scaffold remains attached to the anticodon throughout the formation of the encoded molecule, thereby forming an anchorage point for the encoded molecule. The scaffold molecule may comprise more than a single reactive group. Usually, the one or more reactive groups of the scaffold are recipient reactive groups, i.e. reactive groups capable of forming a chemical connection to another chemical entity.

A second group of chemical entities comprises chemical entities which are capable of being transferred to a recipient reactive group, e.g. a recipient reactive group of a scaffold. The chemical entity can be selectively cleaved from the remainder of the building block by a suitable process following the formation of a connection between the chemical entity and the recipient reactive group. The selective cleavage may be suitable because the formation of the chemical bond between the chemical entity and the recipient reactive group and the cleavage of the chemical entity from the remainder of the building block can proceed in two separate steps using optimal conditions for each step. Alternatively, the reaction proceeds in a single step, i.e. the chemical entity is simultaneously reacted with the reactive site and cleaved from the remainder of the building block. The latter method involving simultaneous reaction and cleavage may be preferred when a fast method for formation of a single encoded molecule or a library of molecules are envisaged.

According to the third group of chemical entities, one part of an affinity pair is applied. Suitable examples of the one part of the affinity pair is biotin and dinitrophenol. Biotin can be selectively recognized by avidine or streptavidine and dinitrophenol can be selectively recognized by an antibody raised against that epitope. The incorporation of one part of an affinity pair into the ligation product may be useful in an immobilisation process. As an example, the bifunctional complex comprising the encoded molecule, may be recovered following the partition step simply by adding the immobilized second part of the affinity pair.

The reactive groups appearing on the anticodons may in some embodiments be protected at the 3' or 5' end, because it may be desirable to be able to direct the incorporation of the individual building blocks. It may also be desirable to have the building block immobilized before the incorporation in the ligation product. The immobilisation may be achieved attaching the protection group of the anticodon to a solid support, such that the protection group appears between the anticodon and the solid support. The advantages of immobilising the nascent building block to a solid support is that it is possible to produce the final building block while remaining connected to the solid support. As is well known to the skilled organic chemist, solid support synthesis affords many advantageous over liquid reactions. The protection group is in an aspect of the invention photocleavable and preferably cleavable by exposure to UV light. In a preferred embodiment, a phosphate group is formed at the 5' end of the anticodon by deprotection, converting the anticodon to a substrate of a ligase. When a ligation primer or a nascent ligation product exposes a 5'-phosphate and the anticodon of a building block to be incorporated is able to hybridise next to the nucleotide comprising the 5'-phosphate, the 3'-end of the anticodon can be ligated to the 5'-end of the primer or nascent ligation product by a suitable ligase. Subsequently, the ligation product is exposed to a condition which deprotects the 5'-end of the anticodon, thereby providing a 5'-phosphate group of the nascent ligation product, which may be used in a subsequent incorporation of building blocks.

The nucleic acid sequence associated with the reactive site may involve a covalent or non-covalent, such as hybridisation, attachment between the sequence and the reactive site. Suitably the reactive site is covalently attached to the template. The reactive site may be part of a scaffold molecule or may be chemical entity according to the second group described above. In one aspect of the invention the nucleic acid sequence associated with a reactive site is a building block. The formation of an encoded molecule according to the present invention generally implies that a first anticodon of a building block is ligated to a primer complementing a priming sequence of the template. In some embodiments of the invention the primer may be absent and the ligation product is formed by ligating building blocks together. However, when enzymatic ligation is encountered a ligation primer is generally used, even though it is possible simply to ligate building blocks together with the application of a ligation primer. In one aspect of the invention, the primer is covalently connected to the template, thereby forming a covalent connection between the anticodon and the template. The covalent connection may be formed by chemically cross-linking the strands or by connecting the primer trough a hairpin loop to the template.

The anticodon of a building block may be part of an oligonucleotide further comprising a sequence complementing a framing sequence of a template or a part thereof. The complementing framing sequences makes it possible for anticodons to recognise specific positions of codons on the template. As explained above the framing sequences and thus the complementing sequences may be alternating to allow for two different pools of building blocks to be added. The incorporation of building blocks can occur stepwise or two or more building block may be incorporated in a ligation product in the same ligation step. Stepwise ligation of building blocks may be desirable when the encoded molecule is formed by stepwise reacting the chemical entities arriving with newly incorporated building blocks. Incorporation of two or more building blocks may be useful when orthogonal chemical strategies are used, i.e. a reactive group of a chemical entity can react with one reactive group of a scaffold only, whereas other chemical entities comprises reactive groups which may react with distinct reactive groups of a scaffold.

The nucleic acid sequence associated with a reactive site used in the present invention may be comprised of a nascent encoded molecule associated with a ligation product. Subsequently, in one setup of the invention, an anticodon of a building block is ligated to a preceding incorporated anticodon and the chemical entity is reacted. According to another embodiment two or more building blocks are hybridised to the template and subsequently ligated together to form a ligation product.

Generally, a building block is hybridised next to another building block or a primer in order for a ligation to proceed. However, in some aspects of the invention, it may be suitable to have a building block hybridised in a position spaced one or more nucleotides from another building block, nascent ligation product or primer. A spacer nucleotide can be used for joining the building block with the preceding building block, ligation product, or the primer.

In an aspect of the invention, a building block being immobilized on a solid support is hybridised to a codon and subjected to a ligation reaction, followed by a detachment of the building block from the solid support, as explained elsewhere herein.

Different approaches for ligating anticodons, primers and/or nascent ligation products can be applied. According to a first approach the anticodon is ligated to a nucleic acid by chemical means. The chemical means may be selected from various chemistries known to the skilled man. Examples of chemical ligation methods include:

a) a nucleic acid, such as a first anticodon, comprising a 3'-OH group and a second nucleic acid, such as a second anticodon comprising a 5'phosphor-2-methylimidazole group. The 3'- and 5' reactive group are reacted to form a phosphodiester internucleoside linkage, b) a nucleic acid, such as a first anticodon, comprising a phosphoimidazolide group at the 3'-end and a second nucleic acid comprising a phosphoimidazolide at the 5'-end, which are reacted to form a phosphodisester internucleoside linkage, c) a nucleic acid, such as a first anticodon comprising a 3'-phosphorothioate group and a second nucleic acid sequence comprising a 5'-iodine, which are reacted to form the internucleoside linkage 3'-O—P(=O)(OH)—S-5', and d) a nucleic acid, such as a first anticodon comprising a 3'-phosphorothioate group and a second nucleic acid, such as a second anticodon comprising a 5'-tosylate, which are reacted to form the internucleoside linkage 3'-O—P(=O)(OH)—S-5'.

In a preferred aspect of the invention, an enzyme is used for ligating an anticodon to a nucleic acid. The enzymes capable of ligating two nucleic acids together are generally referred to as ligases. Preferred ligases are selected from the group consisting of DNA ligase, and RNA ligase. The DNA ligase may be selected among the group consisting of Taq DNA ligase, T4 DNA ligase, T7 DNA ligase, and *E. coli* DNA ligase. In some aspects of the invention enzymatic ligation is preferred because a higher specificity generally is obtained and shorter anticodons may be used.

Following the ligation step the reaction of chemical entities is conducted at conditions where the ligation product is single stranded. A single stranded ligation product may be obtained in various ways. In one aspect of the invention, the single stranded ligation product is obtained using denaturing conditions. The denaturing conditions may i.a. be obtained by using a media selected from organic solvents, aprotic solvents, acidic solvents, denaturants, and alkaline solvents. In another aspect of the invention the denaturing conditions are obtained by heating to a temperature above the melting temperature of the duplex. The single stranded ligation product may also be obtained by degrading the template.

The template can be degraded by various means, e.g. by providing an DNA template and an RNA ligation product and treating the DNA:RNA duplex with RNAseH, RNAseA, RNAse 1, weak alkaline conditions (pH 9-10), or aqueous Pb(Ac)2; by providing a DNA template comprising a thiophosphate in the internucleoside linker and an DNA or RNA anti-codon ligation product, and subsequent treating with aqueous iodine; or providing a DNA or RNA ligation product and a DNA template comprising an uracil nucleobase, treating with uracil-glycosylase and subsequent weak acid.

In another aspect the single stranded ligation product is obtained by removing the template. The template may be removed by a process comprising cleaving a bond between the ligation product and the template, subjecting to denaturing conditions and separating of the template. The bond between the ligation product and the template may be cleaved by a restriction endonuclease.

In certain aspects of the invention, the template is separated from the ligation product by a process which involves providing the template or the ligation product with a first part of an affinity pair. The first part of the affinity pair may be biotin or a similar moiety. The template or the ligation product having appended a biotin moiety can be bound to avidine or streptavidin immobilized on a solid support, thereby rendering the separation possible.

According to another approach, the single stranded ligation product is obtained by making the template strand double stranded. The double stranded template can be produced by competition hybridisation of a nucleotide similar to the ligation product, or by annealing a primer to the template and extending said primer over the extent of the template using a polymerase.

Various types of reactions are possible between reactant according to the invention. In one aspect, the reaction of the chemical entity of an incorporated building block with a reactive site is an acylation reaction. Suitably the reactive site is an amine and the bond form is an amide bond. Other types of reactions include alkylating reactions, in which a carbon-carbon single bond is formed, and Wittig type reactions, in which a carbon-carbon double bond is formed.

Linkers between chemical entities and the anticodon may be maintained or cleaved following the reaction of the chemical entities. When more than a single chemical entity is reacted usually one or more bond between the encoded molecule or nascent encoded molecule are cleaved to present the display molecule more efficient to e.g. a target.

In the method depicted above, steps ii) through iv) may be repeated as appropriate using a nascent complex as the template and anticodon(s) directed to a non-used codon in the building blocks to be incorporated. The repetition of the process steps allows for a multi-step incorporation and reaction of building block. Multi-step incorporation may be of advantage because separate reaction conditions may be used for each chemical entity to be reacted with the nascent encoded molecule, thereby allowing for a wider range of possible reactions.

Following the formation of the encoded molecule, a post treatment may be provided for. The post treatment may involve cleavage of bonds such that the encoded molecule is maintained connected to the template through a single bond only. Post treatment may also involve deprotection, i.e. removal of protective groups used during the reactions of the chemical entities.

According to a preferred aspect of the invention, a plurality of templates and building blocks are processed simultaneously or sequentially forming a library of complexes. Suitably, a large pool of templates, such as 108 are provided. This pool of templates is contacted with a pool of building blocks directed to the each codon of the plurality of templates. Preferably two or more pools of building blocks are added sequentially to obtain a multi-step incorporation and reaction. In one aspect of the invention the nucleotide sequences harbouring the different anticodons in each pool have an identical flanking sequence to ensure that the incorporation will occur in frame.

The invention also relates to a library of different complexes, each complex comprising an encoded molecule and a template, which has encoded the chemical entities which has participated in the synthesis thereof, said library being obtainable by processing a plurality of different templates and a plurality of building blocks as depicted above.

The invention also pertains to a method comprising subjecting the library of complexes to a condition partitioning complexes displaying a predetermined property from the remainder of the library. The condition for partitioning of the desired complexes can include subjecting the library of complexes to a molecular target and partitioning complexes binding to said target. Subsequently, nucleic acid sequences comprising the codons and/or the anticodons and/or sequences complementary thereto may be recovered from the partitioned complexes. The nucleic acid sequences of the partitioned complexes are preferably amplified to produce more copies of the templates from successful complexes. In a preferred aspect the nucleic acid sequences of the partitioned complexes are amplified using the polymerase chain reaction (PCR). In one aspect, the amplification product is used to prepare one or more templates which may be utilized in the method of the invention.

Several rounds of synthesis of bifunctional molecules, partitioning of complexes having a desired property, and amplification of templates from complexes having the desired properties can be conducted. As an example, 2 to 15 rounds may applied, suitable 3 to 7 rounds.

Template

It is preferred that the template is divided into coding regions or codons, which codes for specific chemical entities. A codon is a sequence of nucleotides or a single nucleotide. The templates are usually amplifiable and the nucleobases are in a certain aspect selected from the natural nucleobases (adenine, guanine, uracil, thymine, and cytosine) and the backbone is selected from DNA or RNA, preferably DNA.

In the generation of a library, a codon of a single nucleotide will allow for the incorporation of four different chemical entities into the encoded molecule, using the four natural DNA nucleobases (A, C, T, and G). However, to obtain a higher diversity, a codon in certain embodiments preferably comprises at least two and more preferred at least three nucleotides. Theoretically, this will provide for $4^2$ and $4^3$, respectively, different chemical entities. The codons will usually not comprise more than 200 nucleotides. It is preferred to have codons with a sequence of 3 to 300 nucleotides, more preferred 4 to 15 nucleotides.

The template sequence will in general have at least two codons which are arranged in sequence, i.e. next to each other. Each of the codons may be separated by a framing sequence. Depending on the encoded molecule formed, the template sequence may comprise further codons, such as 3, 4, 5, or more codons. Each of the further codons may be separated by a suitable framing sequence. Preferably, all or at least a majority of the codons of the nucleic acid sequence are arranged in sequence and each of the codons is separated from a neighbouring codon by a framing sequence. The framing sequence may have any appropriate number of nucleotides, e.g. 1 to 20. Alternatively, codons on the template may be designed with overlapping sequences.

Generally, it is preferred to have more than two codons on the template to allow for the synthesis of more diverse encoded molecules. In a preferred aspect of the invention the number of codons of the template sequence is 2 to 100, more preferred the template sequences comprises 3 to 20 codons.

The framing sequence may serve various purposes. In one setup of the invention, the framing sequence identifies the position of a codon. Usually, the framing sequence either upstream or downstream of a codon comprises information which allows determination of the position of the codon.

The framing sequence may also or in addition provide for a region of high affinity. The high affinity region may ensure that the hybridisation of the template sequence with the anti-codon will occur in frame. Moreover, the framing sequence may adjust the annealing temperature to a desired level.

A framing sequence with high affinity can be provided by incorporation of one or more nucleobases forming three hydrogen bonds to a cognate nucleobase. An example of nucleobases displaying this property is guanine and cytosine. Alternatively, or in addition, the framing sequence may be subjected to back bone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The template sequence may comprise flanking regions around the coding segments. The flanking regions can serve as priming sites for an amplification reaction, such as PCR. The template may in certain embodiments comprise a region complementary to the flaking region to allow for a hairpin loop to be formed.

It is to be understood that when the term template is used in the present description and claims, the sequence may be in the sense or the anti-sense format, i.e. the template sequence can be a sequence of codons which actually codes for the molecule or can be a sequence complementary thereto.

It is within the capability of the skilled person in the art to construct the desired design of an oligonucleotide. When a certain annealing temperature is desired it is a standard procedure to suggest appropriate compositions of nucleic acid monomers and the length thereof. The construction of an appropriate design may be assisted by software, such as Vector NTI Suite or the public database at the internet address http://www.nwfsc.noaa.gov/protocols/oligoTMcalc.html.

The conditions which allow hybridisation of the template with a nucleic acid, such as an anti-codon, are influenced by a number of factors including temperature, salt concentration, type of buffer, and acidity. It is within the capabilities of the person skilled in the art to select appropriate conditions to ensure that the contacting between the template sequences and the building blocks are performed at hybridisation conditions. The temperature at which two single stranded oligonucleotides forms a duplex is referred to as the annealing temperature or the melting temperature.

Encoded Molecule

The encoded molecule may be formed by a variety of reactants which are reacted with each other and/or a scaffold molecule. Optionally, this reaction product may be post-modified to obtain the final display molecule. The post-modification may involve the cleavage of one or more chemical bonds attaching the encoded molecule to the template in order more efficiently to display the encoded molecule.

The formation of an encoded molecule generally starts by a scaffold, i.e. a chemical unit having one or more reactive groups capable of forming a connection to another reactive group positioned on a chemical entity, thereby generating an addition to the original scaffold. A second chemical entity may react with a reactive group also appearing on the original scaffold or a reactive group incorporated by the first chemical entity. Further chemical entities may be involved in the formation of the final reaction product. The formation of a connection between the chemical entity and the nascent encoded molecule may be mediated by a bridging molecule. As an example, if the nascent encoded molecule and the chemical entity both comprise an amine group a connection between these can be mediated by a dicarboxylic acid.

The encoded molecule may be attached directly to the template sequence or through a suitable linking moiety. Furthermore, the encoded molecule may be linked to the template sequence through a cleavable linker to release the encoded molecule at a point in time selected by the experimenter.

The chemical entities are suitably mediated to the nascent encoded molecule by a building block, which further comprises an anticodon. The anti-codon serves the function of transferring the genetic information of the building block in conjunction with the transfer of a chemical entity to the nascent complex. The chemical entities are preferably reacted without enzymatic interaction. Notably, the reaction of the chemical entities is preferably not mediated by ribosomes or enzymes having similar activity.

The chemical entity of the building block may in most cases be regarded as a precursor for the structural entity eventually incorporated into the encoded molecule. In other cases the chemical entity provides for the eliminations of chemical units of the nascent scaffold. Therefore, when it in the present application with claims is stated that a chemical entity is transferred to a nascent encoded molecule or a reactive site, it is to be understood that not necessarily all the atoms of the original chemical entity is to be found in the eventually formed encoded molecule. Also, as a consequence of the reactions involved in the connection, the structure of the chemical entity can be changed when it appears on the nascent encoded molecule. Especially, the cleavage resulting in the release of the entity may generate a reactive group which in a subsequent step can participate in the formation of a connection between a nascent complex and a chemical entity.

Building Block

The chemical entities that are precursors for structural additions or eliminations of the encoded molecule may be attached to a building block prior to the participation in the formation of the reaction product leading the final encoded molecule. Besides the chemical entity, the building block generally comprises an anti-codon.

The chemical entity of the building block comprises at least one reactive group capable of participating in a reaction which results in a connection between the chemical entity of the building block and another chemical entity or a scaffold associated with the nascent complex. The connection is facilitated by one or more reactive groups of the chemical entity. The number of reactive groups which appear on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds.

The reactive group of the building block may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a reagent or an enzyme. The cleavage results in a transfer of the chemical entity to the nascent encoded molecule or in a transfer of the nascent en-coded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent encoded molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational space sampled by the reactive group is optimized for a reaction with the reactive group of the nascent encoded molecule or reactive site.

The anticodon complements the codon of the template sequence and generally comprises the same number of nucleotides as the codon. The anticodon may be adjoined with a fixed sequence, such as a sequence complementing a framing sequence.

Various specific building blocks are envisaged. Building blocks of particular interest are shown below.

Building Blocks Transferring a Chemical Entity to a Recipient Nucleophilic Group The building block indicated below is capable of transferring a chemical entity (CE) to a recipient nucleophilic group, typically an amine group. The bold lower horizontal line illustrates the building block and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

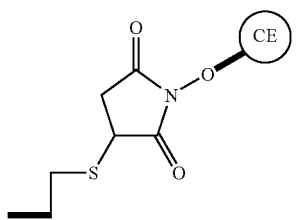

The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold, to transfer the chemical entity to the scaffold, thus converting the remainder of the fragment into a leaving group of the reaction. When the chemical entity is connected to the activator through an carbonyl group and the recipient group is an amine, the bond formed on the scaffold will an amide bond. The above building block is the subject of the Danish patent application No. PA 2002 01946 and the U.S. provisional patent application No. 60/434,439, the content of which are incorporated herein in their entirety by reference.

Another building block which may form an amide bond is

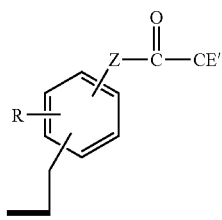

R may be absent or $NO_2$, $CF_3$, halogen, preferably Cl, Br, or I, and Z may be S or O. This type of building block is disclosed in Danish patent application No. PA 2002 0951 and US provisional patent application filed 20 Dec. 2002 with the title "A building block capable of transferring a chemical entity to a recipient reactive group". The content of both patent application are incorporated herein in their entirety by reference.

A nucleophilic group can cleave the linkage between Z and the carbonyl group thereby transferring the chemical entity —(C=O)—CE' to said nucleophilic group.

Building Blocks Transferring a Chemical Entity to a Recipient Reactive Group Forming a C=C Bond A building block as shown below are able to transfer the chemical entity to a recipient aldehylde group thereby forming a double bond between the carbon of the aldehyde and the chemical entity

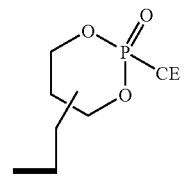

The above building block is comprised by the Danish patent application No. DK PA 2002 01952 and the US provisional patent application filed 20 Dec. 2002 with the title "A building block capable of transferring a chemical entity to a recipient reactive group forming a C=C double bond". The content of both patent applications are incorporated herein in their entirety by reference.

Building Blocks Transferring a Chemical Entity to a Recipient Reactive Group Forming a C—C Bond The below building block is able to transfer the chemical entity to a recipient group thereby forming a single bond between the receiving moiety, e.g. a scaffold, and the chemical entity.

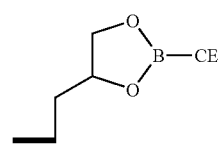

The above building block is comprised by the Danish patent application No. DK PA 2002 01947 and the U.S. provisional patent application No. 60/434,428. The content of both patent applications are incorporated herein in their entirety by reference.

Another building block capable of transferring a chemical entity to a receiving reactive group forming a single bond is

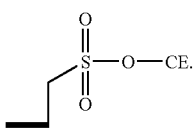

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold.

The chemical entity attached to any of the above building blocks may be a selected from a large arsenal of chemical structures. Examples of chemical entities are H or entities selected among the group consisting of a $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$.

where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —NHN$HR^6$, —C(O)$R^6$, —Sn$R^6_3$, —B(O$R^6)_2$, —P(O)(O$R^6)_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —CO$R^6$, —CN, —OSi$R^6_3$, —O$R^6$ and —N$R^6_2$.

$R^6$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, $NO_2$, —$R^3$, —O$R^3$, —Si$R^3_3$ $R^9$ is =O, —F, —Cl, —Br, —I, —CN, —$NO_2$, —O$R^6$, —N$R^6_2$, —$NR^6$—C(O)$R^8$, —$NR^6$—C(O)O$R^8$, —S$R^6$, —S(O)$R^6$, —S(O)$_2R^6$—COO$R^6$, —C(O)N$R^6_2$ and —(O)$_2$N$R^6_2$.

Partitioning

The partition step may be referred to as a selection or a screen, as appropriate, and includes the screening of the library for encoded molecules having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. E.g. the target can be a protein, peptide, carbohydrate, polysaccharide, glycoprotein, hormone, receptor, antigen, antibody, virus, substrate, metabolite, transition state analogue, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-10 converting enzyme, cytokine receptors, PDGF receptor, type II inosine monophosphate dehydrogenase, β-lactamases, integrin, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc.

Encoded molecules having predetermined desirable characteristics can be partitioned away from the rest of the library while still attached to the template sequence by various methods known to one of ordinary skill in the art. In one embodiment of the invention the desirable products are partitioned away from the entire library without chemical degradation of the attached nucleic acid template such that the templates are amplifiable. The templates may then be amplified, either still attached to the desirable encoded molecule or after separation from the desirable encoded molecule.

In a preferred embodiment, the desirable encoded molecule acts on the target without any interaction between the nucleic acid attached to the desirable encoded molecule and the target. In one embodiment, the bound complex-target aggregate can be partitioned from unbound complexes by a number of methods. The methods include nitrocellulose filter binding, column chromatography, filtration, affinity chromatography, centrifugation, and other well known methods.

Briefly, the library of complexes is subjected to the partitioning step, which may include contact between the library and a column onto which the target is immobilised. Templates associated with undesirable encoded molecules, i.e. encoded molecules not bound to the target under the stringency conditions used, will pass through the column. Additional undesirable encoded molecules (e.g. encoded molecules which cross-react with other targets) may be removed by counter-selection methods. Desirable complexes are bound to the column and can be eluted by changing the conditions of the column (e.g., salt, pH, surfactant, etc.) or the template.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of encoded molecules on the basis of a desired function; this can be extended to the selection of molecules with a desired function and specificity. Specificity can be required during the selection process by first extracting template sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Determining the Template Sequence

The nucleotide sequence of the template sequence present in the isolated bifunctional molecules is determined to identify the chemical entities that participated in the preselected binding interaction.

Although conventional DNA sequencing methods are readily available and useful for this determination, the amount and quality of isolated bifunctional molecule may require additional manipulations prior to a sequencing reaction.

Where the amount is low, it is preferred to increase the amount of the template sequence by polymerase chain reaction (PCR) using PCR primers directed primer binding sites present in the template sequence.

In addition, the quality of the isolated bifunctional molecule may be such that multiple species of bifunctional molecule are co-isolated by virtue of similar capacities for binding to the target. In cases where more than one species of bifunctional molecule are isolated, the different isolated species must be separated prior to sequencing of the identifier oligonucleotide.

Thus in one embodiment, the different template sequences of the isolated bifunctional complexes are cloned into separate sequencing vectors prior to determining their sequence by DNA sequencing methods. This is typically accomplished by amplifying all of the different template sequences by PCR as described herein, and then using a unique restriction endonuclease sites on the amplified product to directionally clone the amplified fragments into sequencing vectors. The cloning and sequencing of the amplified fragments then is a routine procedure that can be carried out by any of a number of molecular biological methods known in the art.

Alternatively, the bifunctional complex or the PCR amplified template sequence can be analysed in a microarray. The array may be designed to analyse the presence of a single codon or multiple codons in a template sequence.

Nucleotides

The nucleic acids used in the present invention may be a single nucleotide or several nucleotides linked together in an oligonucleotide. Each nucleotide monomer is normally composed of two parts, namely a nucleobase moiety, and a backbone. The back bone may in some cases be subdivided into a sugar moiety and an internucleoside linker.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases.

Examples of suitable specific pairs of nucleobases are shown below:

Natural Base Pairs

Adenine

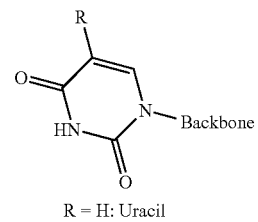
R = H: Uracil
R = CH₃: Thymine

-continued

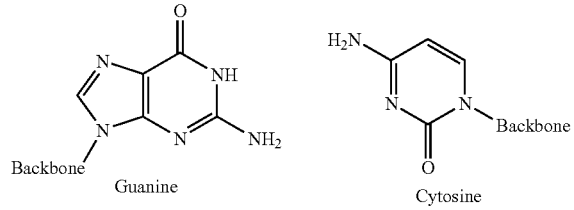
Guanine

Cytosine

Synthetic Base Pairs

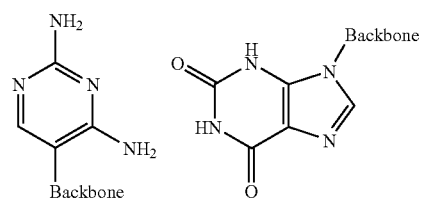

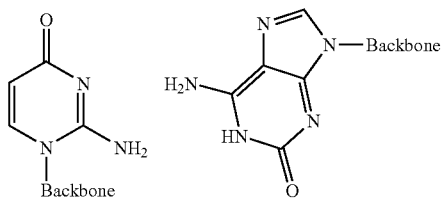

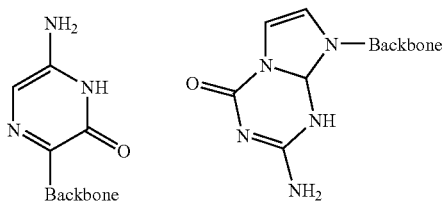

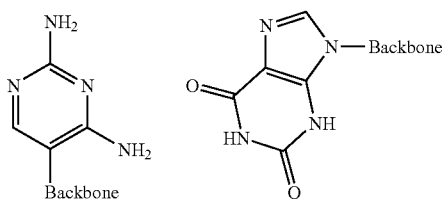

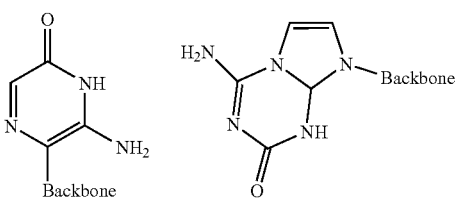

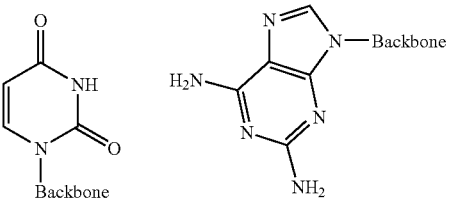

Synthetic Purine Bases Pairring with Natural Pyrimidines

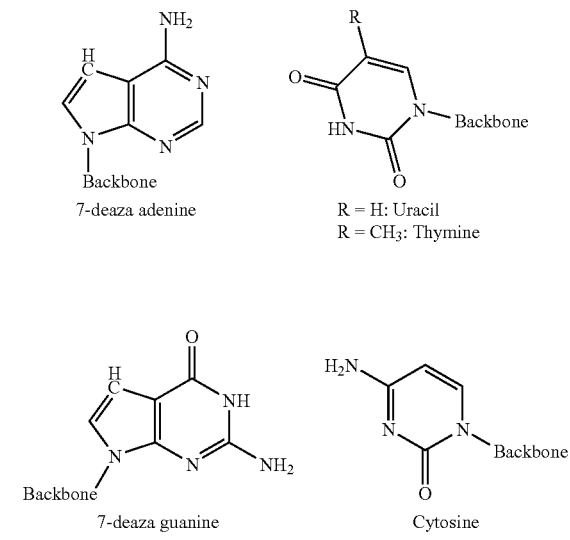

7-deaza adenine

R = H: Uracil
R = CH₃: Thymine 7-deaza guanine

Cytosine

Suitable examples of backbone units are shown below (B denotes a nucleobase):

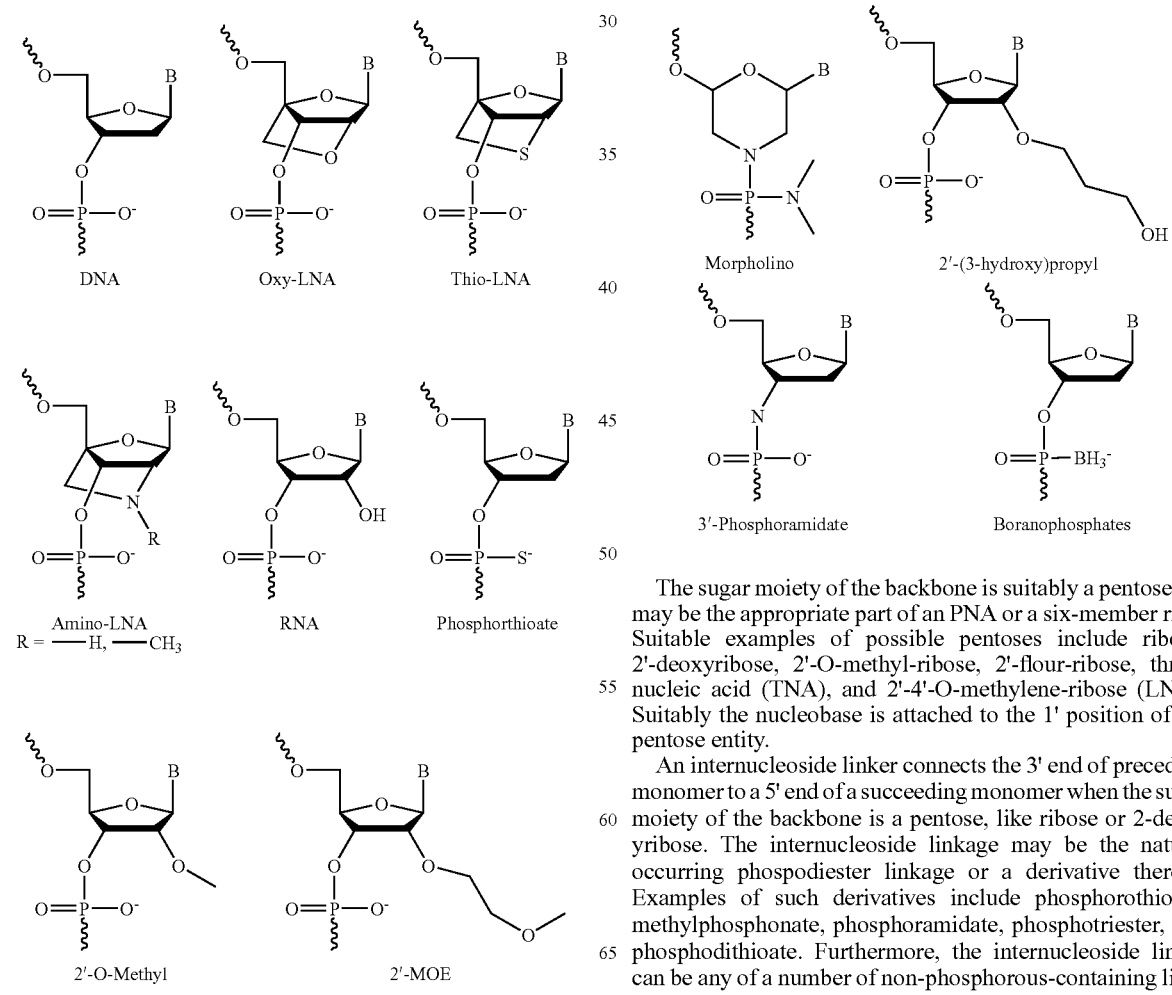

The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, threo-nucleic acid (TNA), and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage may be the natural occurring phospodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base because inosine can pair nearly isoenergetically with A, T, and C.

Synthesis of Nucleic Acids

Oligonucleotides can be synthesized by a variety of chemistries as is well known. For synthesis of an oligonucleotide on a substrate in the direction of 3' to 5', a free hydroxy terminus is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether. The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide in the direction of 5' to 3', a free hydroxy terminus on the linker is required as before. However, the blocked nucleotide to be added has the blocking chemistries reversed on its 5' and 3' termini to facilitate addition in the opposite orientation. A nucleotide with a free 3' hydroxyl and 5' DMT ether is first blocked at the 3' hydroxy terminus by reaction with TBS-Cl in imidazole to form a TBS ester at the 3' terminus. Then the DMT-blocked 5' terminus is deblocked with DCA in DCM as before to form a free 5' hydroxy terminus. The reagent (N,N-diisopropylamino)(cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-Cl adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

Extension and Amplification

The use of the polymerase chain reaction (PCR) is a preferred embodiment, for the production of the templates using the nucleic acids of the selected complexes as templates.

For use in this invention, the template sequences are preferably comprised of polynucleotide coding strands, such as mRNA and/or the sense strand of genomic DNA or non-natural nucleic acids, like TNA and LNA which may be used as template for a polymerase. If the genetic material to be processed is in the form of double stranded nucleic acid, it is usually first denatured, typically by melting, into single strands. The nucleic acid is subjected to a PCR reaction by treating (contacting) the sample with a PCR primer pair, each member of the pair having a preselected nucleotide sequence. The PCR primer pair is capable of initiating primer extension reactions by hybridizing to the PCR primer binding site on template oligonucleotide, preferably at least about 10 nucleotides in length, more preferably at least about 12 nucleotides in length. The first primer of a PCR primer pair is sometimes referred to as the "anti-sense primer" because it is extended into a non-coding or anti-sense strand of a nucleic acid, i.e., a strand complementary to a coding strand. The second primer of a PCR primer pair is sometimes referred to as the "sense primer" because it is adjoined with the coding or sense strand of a nucleic acid.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR reaction product, thereby amplifiyng the templates in the isolated complex.

PCR is typically carried out by thermocycling i.e., repeatedly increasing and decreasing the temperature of a PCR reaction admixture within a temperature range whose lower limit is about 30 degrees Celsius (30° C.) to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined for assaying for mutations.

The PCR reaction is performed using any suitable method. Generally it occurs in a buffered aqueous solution, i.e., a PCR buffer, preferably at a pH of 7-9, most preferably about 8. Preferably, a molar excess of the primer is admixed to the buffer containing the template strand. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.-100° C. for about 1 to 10 minutes, preferably from 1 to 4 minutes. After this heating period the solution is allowed to cool to a primer hybridization temperature. The synthesis reaction may occur at from room temperature up to a temperature above which the polymerase (inducing agent) no longer functions efficiently. Thus, for example, if DNA polymerase is used as inducing agent, the temperature is generally no greater than about 40° C. The thermocycling is repeated until the desired amount of PCR product is produced. An exemplary PCR buffer comprises the following: 50 mM KCl; 10 mM Tris-HCl at pH 8.3; 1.5 mM MgCl2; 0.001% (wt/vol) gelatin, 200 µM dATP; 200 µM dTTP; 200 µM dCTP; 200 µM dGTP; and 2.5 units *Thermus*

*aquaticus* (Taq) DNA polymerase I (U.S. Pat. No. 4,889,818) per 100 microliters (μl) of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, Taq DNA polymerase, Pfu polymerase, Vent polymerase, HIV-1 Reverse Transcriptase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn-over rate of the RNA polymerase amplifies the starting polynucleotide as has been described by Chamberlin et al., The Enzymes, ed. P. Boyer, pp. 87-108, Academic Press, New York (1982). Amplification systems based on transcription have been described by Gingeras et al., in PCR Protocols, A Guide to Methods and Applications, pp. 245-252, Innis et al., eds, Academic Press, Inc., San Diego, Calif. (1990).

If the inducing agent is a DNA-dependent RNA polymerase and, therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the method. PCR amplification methods are described in detail in U.S. Pat. Nos. 4,683,192, 4,683,202, 4,800,159, and 4,965,188, and at least in several texts including PCR Technology: Principles and Applications for DNA Amplification, H. Erlich, ed., Stockton Press, New York (1989); and PCR Protocols: A Guide to Methods and Applications, Innis et al., eds., Academic Press, San Diego, Calif. (1990). The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 10 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleic acid can be attached to the 5' end of the primer, with the remainder of the primer sequence being substantially complementary to the strand. Such non-complementary fragments typically code for an endonuclease restriction site or used as a linker to connect to a label, such as biotin.

Primers of the present invention may also contain a DNA-dependent RNA polymerase promoter sequence or its complement. See for example, Krieg et al., Nucl. Acids Res., 12:7057-70 (1984); Studier et al., J. Mol. Biol., 189:113-130 (1986); and Molecular Cloning: A Laboratory Manual, Second Edition, Maniatis et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide. This may be used for selective degradation of the RNA strand, which is prone to disintegration upon treatment with a strong base.

Primers may also contain a template sequence or replication initiation site for a RNA-directed RNA polymerase. Typical RNA-directed RNA polymerase include the Qβ replicase described by Lizardi et al., Biotechnology, 6:1197-1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., J. Mol. Biol., 89:719-736 (1974).

In one embodiment, the present invention utilizes a set of polynucleotides that form primers having a priming region located at the 3'-terminus of the primer. The 3'-terminal priming portion of each primer is capable of acting as a primer to catalyze nucleic acid synthesis, i.e., initiate a primer extension reaction off its 3' terminus. One or both of the primers can additionally contain a 5'-terminal non-priming portion, i.e., a region that does not participate in hybridization to the preferred template. The 5'-part of the primer may be labelled as described herein above.

BRIEF DESCRIPTION OF THE FIGURES

FIG. 2 shows a general method for single-step ligation of multiple building blocks.

FIG. 12. In (A) a hybridisation complex comprising building blocks and connector oligonucleotides is generated. One of the connectors is immobilised to a solid support. The building blocks are then ligated and the ligated building blocks are separated from the connectors. The connectors may optionally be ligated. In (B) the chemical entities are reacted to form a bifunctional complex.

DETAILED DESCRIPTION OF THE INVENTION

Figure 1:
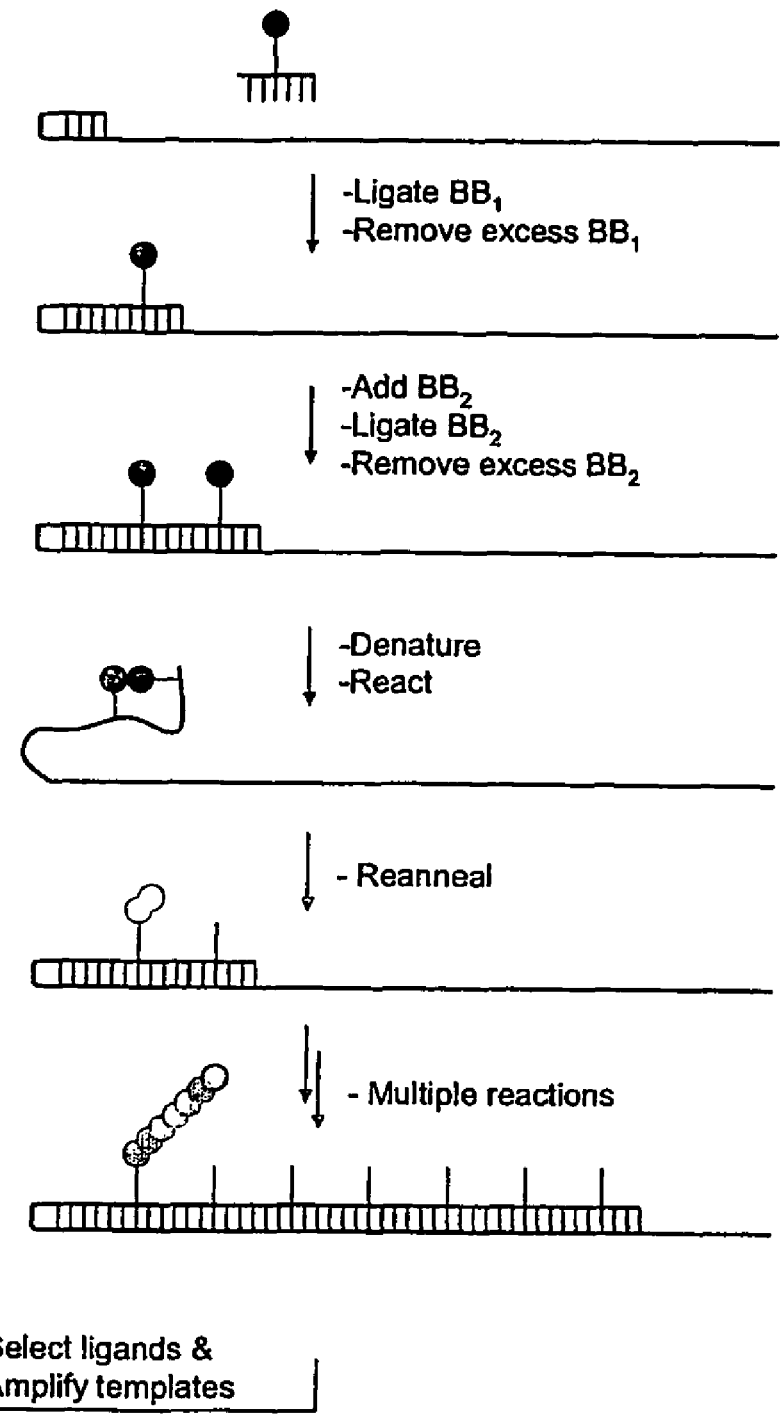
FIG. 1 discloses a general method for producing an encoded molecule using stepwise ligation and stepwise reaction of chemical entities.

FIG. 1 discloses the principles of stepwise ligation and stepwise reaction. Initially, a template comprising a hairpin loop is provided. The hairpin loop is formed due to the fact that an outer sequence, such as a flanking sequence is complementary to a sequence in the interior of the sequence harbouring the template. Under hybridisation conditions the complementary sequences will anneal to each other thus forming a starting point for a ligase at the one end of the oligonucleotide. In a subsequent step a building block is added. The building block comprises a nucleic acid sequence complementary to the sequence next to the interior sequence. Either of the ends of the abutting nucleotides generally comprises a phosphate group to make it possible for a ligase to perform the action of ligating the ends together, thereby forming a contigues nucleotide sequence.

The amount of building block added is generally in excess to ensure sufficient substrate for the ligase and a complete as possible reaction. After the ligation step the excess building block not ligated to the template-primer complex is removed and a second building block is added. The second building block has an anticodon complementary to a sequence of the template such that one end of the anticodon of the second building block abuts the anticodon of the preceding incorporated building block. Under suitable hybridisation conditions a ligase is added to ligate the second anticodon to the preceding ligation product to form a single nucleotide sequence comprising the template and the two building blocks. Subsequent to the ligation, excess amounts of the second building block is removed.

The reactions between the chemical entities can in general not take place when the strand comprising the ligation product is annealed to the template strand because the linker connecting the anticodon and the chemical entity is to short for two adjacent chemical entities to be in sufficient proximity for a reaction to occur. Therefore, the reaction is not possible before the ligated strand is single-stranded. The single stranded ligation product is obtained in the present instance by denature the double helix formed by the ligation product and the template. Under denaturing conditions, the chemical entities are reacted, such that one of the chemical entities is transferred to the other.

The process may be repeated an appropriate number of times until a predetermined number and type of chemical entities have reacted to form the final encoded reaction product. Each cycle starts with the addition of a building block, which has an anticodon with a sequence that anneals next to a preceding anticodon. Excess amounts of the building block is subsequently removed and a ligase is added in order to adjoin the building block to the previously formed ligation product. After the ligation, the chemical entity of the just incorporated building block is reacted with the nascent encoded molecule. The formed encoded molecule may be subjected to various alterations, such as linker cleavage, deprotection, intra-molecular reactions, etc to form the final display molecule. The bifunctional complex comprising the display molecule and the ligation product may be subjected to a partition step, as described herein, to select one or more display molecules displaying desired properties.

In some embodiments of the present invention it may be desirable to synthesise polymers or linear molecules using stepwise chemical reactions i.e. ligation and subsequent reaction of a chemical entity before addition of the next building block. This is particularly desirable when each building block is to be assembled into a polymer or linear molecule using identical reaction types. One example of this reaction type is the use of acylation reactions in the formation of amide bonds in the encoded polymers or linear molecules. Thus, a stepwise procedure will prevent the reaction of chemical entities in random order and instead assure that the chemical entities are added in a ordered fashion according to the template sequence. If multiple anticodons were to be ligated in one single step and the attached chemical entities could react at random a laborious deconvolution step would be required to identify the exact molecules with desired properties. In contrast, if linear or branched molecules is to be synthesised from orthogonal and compatible chemical reactions it may be desirable to ligate several or all anticodons in a single step and subsequent react one or more of the chemical entities.

FIG. 2 discloses a method in which multiple building blocks are annealed together in a single process step. In some embodiments, it may be desirable to ligate two or more anticodons of building blocks to the template-primer complex in a single step. This could be particular useful for the synthesis of molecules when using orthogonal chemistries for the assembly of the encoded molecule.

Initially, a template comprising a hairpin loop is provided. The hairpin loop is formed due to the fact that an outer sequence, such as a flanking sequence is complementary to a sequence in the interior of the sequence harbouring the template. Under hybridisation conditions the complementary sequences will anneal to each other thus forming a starting point for a ligase at the one end of the oligonucleotide. Various building blocks are added subsequently. The anticodons are designed such that they aligns on the template under hybridisation conditions. The alignment is directed by the sequence of the template. Subsequently or simultaneously with the alignment process the anticodons are ligated together by a ligase or similar ligation means. Once the anticodons have been ligated together, the ligation product is made single stranded by inducing denaturing conditions, that is, conditions ensuring that the double helix formed by the ligation product and the template is disrupted. The chemical entities attached to the ligation product, which is in a single stranded state, are reacted all together or at least the majority of the chemical entities is reacted to form a reaction product. The reaction product may be modified by cleavage of one or more linkers connecting the reaction product with the ligation product to display the encoded reaction product more efficiently. It may also be advantageously to cleave at least some of the linkers in order for the ligated strand to anneal to the template before the bifunctional molecule is subjected to a partition process because a single stranded nucleic acid may be affect a the partition process. Especially, single stranded RNA are known to be able to interact with biological molecules. Furthermore, a double stranded nucleic acid is generally more stable compared to a corresponding single stranded molecule, i.e. a double stranded nucleic acid is generally able to withstand higher temperatures and extreme pH values.

Figure 6:
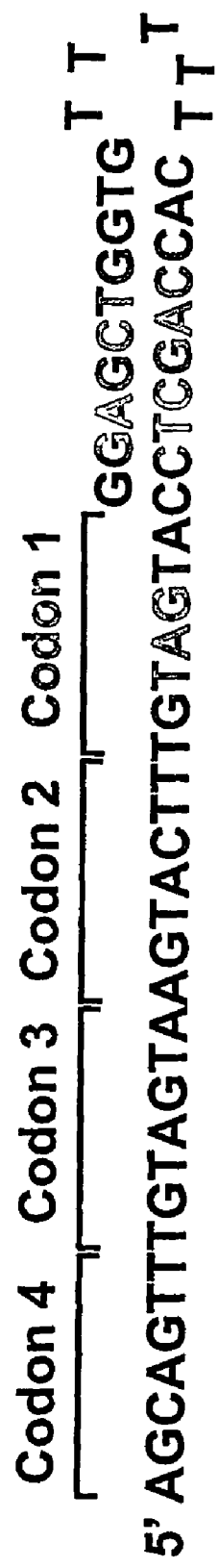
FIG. 6 shows a schematic representation of a set-up useful for the stepwise ligation of anticodon. The sequences, from top to bottom, are SEQ ID NOs:11, 3 and 4.

A simple method to assure stepwise ligation is to include reading frame determinants in the template sequence, as shown in FIG. 6. Reading frame determinants can be fixed sequences that prevent multiple ligation reactions on the same template. Thus, by alternating the reading frame determinants in the template. only a certain subtype of anticodons can be ligated. In this set-up a primer-template is designed containing 4 codons of 7 nucleotides. The $1^{st}$ 7 nucleotide codon sequence adjacent to the free 3' OH-group of the template-primer complex is composed of the general sequence: 5'-TN-NANNA-3' encoding up to 256 different chemical entities. The $2^{nd}$ codon is composed of the general sequence: 5'-AN-NANNT-3'. The $3^{rd}$ and $4^{th}$ codons are identical to the $1^{st}$ and $2^{nd}$ codon regions, respectively. Two sets of anticodon-building blocks are prepared where the $1^{st}$ anticodon set is composed of the general sequence: 5'-pTNNXNNA-3' and the $2^{nd}$ of of general sequence: 5'-pANNXNNT-3', where p=phosphate and X is Carboxy-dT useful for the attachment of chemical entities. Stepwise ligation is accomplished by ligation of the $1^{st}$ anticodon set to the template-primer complex shown schematically in FIG. 6. Since $1^{st}$ anticodon set is complementary to codon 1 and 3 only, a ligation reaction using this anticodon subset will result in the sequence-specific ligation of anticodon-building blocks complementary to codon 1. Subsequently, all unused $1^{st}$ building blocks are removed followed by addition of the second set of building blocks to the template-primer complex containing a ligated $1^{st}$ building block. This ligation step will result in the sequence-specific addition of an anti-codon complementary to codon 2. Excess anticodon-building block 2 is removed. Next, the first set of building blocks are added to ligate an anticodon-building block complementary to the $3^{rd}$ codon with the template-primer complex carrying anticodon building blocks complementary to codon 1 and 2. After removal of excess anticodon-building blocks, anticodon-building blocks from the $2^{nd}$ subset are used for ligation at codon position 4. These alternating ligation steps using two or more subsets of anticodon building blocks allows the experimenter to allocate and ligate specific subsets of anti-codon-building blocks to specific positions on the template/primer complex using reading frame determinants.

The chemical reactions required to cross-link and/or transfer a building block can be conducted at any time during this protocol. In one embodiment of this invention it may be desirable to cross-link and transfer a building block after each ligation step to assign a specific building block to a specific position in e.g a polymer or linear molecule. If such a scheme is used a deconvolution procedure will most likely not be required. In some embodiments it may be desirable to have several or all building blocks ligated to the template-primer complex before performing transfer of building blocks. Furthermore, the building blocks may be reacted with one or more other building block or with a functionality inserted in the template-primer complex.

Using the set-up shown in FIG. 6 it is possible to generate a library of molecules comprising $256^4$=more than a billion different compounds each encoded by a nucleic acid template. Consequently, it is possible to select the compounds having desired properties such as binding to a target (e.g. a receptor protein) or a catalytic function. Following selection, the template(s) that encode the compounds having desired properties is amplified (f.ex by PCR) and used for additional rounds of templated synthesis, selection and amplification. Finally, cloning and sequencing or other means of sequence detection such as sequence-specific array-detection of the selected templates will determine the composition of the selected small molecules.

EXAMPLES

Example 1

Ligation of Building Blocks to Template-Primer Complex

Figure 3:
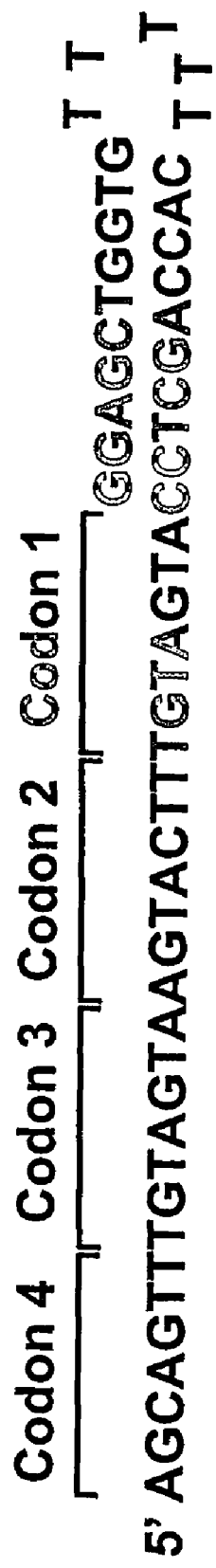
FIG. 3 shows an oligo-architecture alternating reading frame determinants are used for stepwise ligation of building blocks. The first sequence shown is SEQ ID NO:11, the anticodon-building block subtype 1 is SEQ ID NO:3, and the block subtype 2 is SEQ ID NO:4.

In this set-up a DNA template that allows for hairpin structure formation is used as both a template and primer for the ligation of building block oligonucleotides (FIG. 3). FIG. 3 shows template-primer set-up and the complementary 3 oligonucleotide building blocks. The carboxy dT functionality on each building block oligonucleotide is easily introduced at any position in an oligonucleotide using standard phosphoramidite chemistry and can be used as molecular handle for the addition of chemical entities to each specific oligonucleotide sequence.

Ligation of Building Block 1 (BB 1) to the Template-Primer Complex.

500 pmol of 7-mer building block oligonucleotide 1 comprising the carboxy-group was ligated to 500 pmol template-primer complex in a 50 μl volume at 20° C. for 1 hour using Takara ligase kit version 2.0 (TaKaRa™). The sample was extracted twice with 100 μl phenol and purified using double gel-filtration (Biorad microspin 6 columns, Biorad™) and the ligation product was examined by Electrospray MS analysis (ES-MS, Bruker).

The above sequence appears in the sequencing listing as SEQ ID NO:5.

Figure 13:
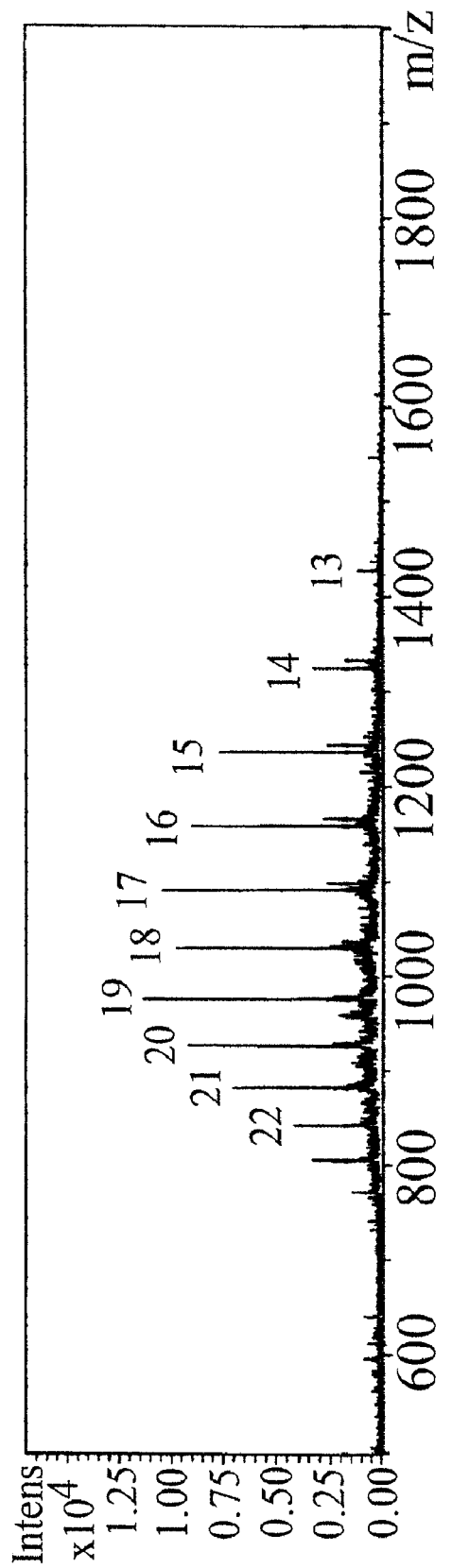
FIG. 13 is a mass spectrogram (SNJ45 +32 −270103.d:-MS, 3.8-7.1 min (#26-#50)) of ligation products, including SEQ ID NO: 5, with the following labeled peaks: 22(A): 842.5, 21(A):882.7, 20(A):927.0, 19(A):975.8, 18(A): 1030.1, 17(A):1090.7, 16(A):1159.0, 15(A):1236.3, 14(A): 1324.6, and 13(A):1426.5 m/z.

FIG. 13 is a mass spectrogram (SNJ45 +32 −270103.d:-MS, 3.8-7.1 min (#26-#50)) with the following labeled peaks: 22(A):842.5, 21(A):882.7, 20(A):927.0, 19(A):975.8, 18(A):1030.1, 17(A):1090.7, 16(A):1159.0, 15(A):1236.3, 14(A):1324.6, and 13 (A):1426.5 m/z.

The expected mass of the ligation product SEQ ID NO:5 was 18556 Da, and the observed mass was 18558 Da, consistent with component A below:

| Component | Deconvoluted Mass | Molecule | Absolute Abundance | Relative Abundance |
|---|---|---|---|---|
| A | 18858.19 | [M − H]− | 78231 | 100.00 |
| B | 18684.09 | [M − H]− | 12988 | 16.60 |
| C | 18611.54 | [M − H]− | 14139 | 18.07 |
| D | 18589.24 | [M − H]− | 7388 | 9.44 |

ES-MS of ligation products obtained from the ligation of template-primer complex and BB1 oligonucleotide shows that the ligation reaction yields a single dominant ligation product corresponding to the template-primer complex ligated to BB1.

Ligation of BB1 & BB2 to the Template-Primer Complex.

Ligation of equimolar BB1, BB2 and template-primer complex was conducted as described above and the products purified and assayed using ES-MS.

The above sequence appears in the sequence listing as SEQ ID NO:6.

Figure 14:
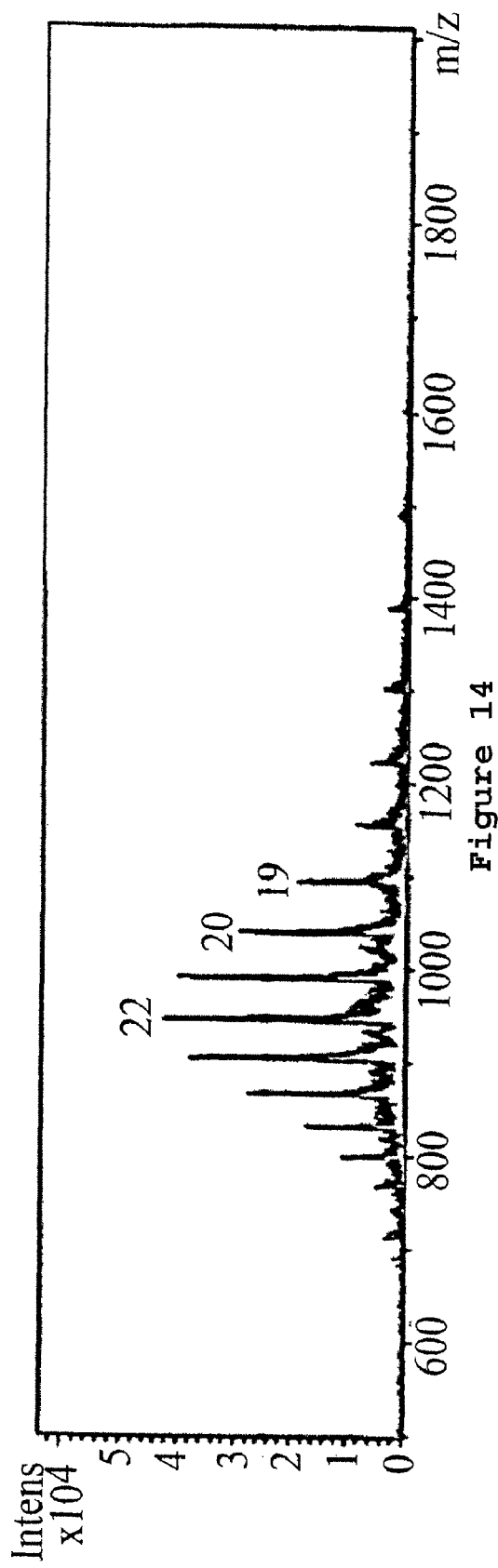
FIG. 14 is a mass spectrogram (SNJ-45+32+33−070203. d: -MS, 3.7-8.5 min (#22-#58)) relating to SEQ ID NO:6, with the following labeled peaks: 22(A):944.6, 20(B):1040.2, 19(A):1093.8, m/z.

FIG. 14 is a mass spectrogram (SNJ-45+32+33−070203.d: -MS, 3.7-8.5 min (#22-#58)) with the following labeled peaks: 22(A):944.6, 20(B):1040.2, 19(A):1093.8, m/z.

The expected mass of SEQ ID NO:6 was 20778 Da and the observed mass was 20780 Da.

| Component | Deconvoluted Mass | Molecule | Absolute Abundance | Relative Abundance |
|---|---|---|---|---|
| A | 20802.20 | [M − H]− | 212727 | 99.95 |
| B | 20823.97 | [M − H]− | 212831 | 100.00 |
| C | 20845.40 | [M − H]− | 162059 | 76.14 |
| D | 20780.56 | [M − H]− | 130576 | 61.35 |

ES-MS of the BB1, BB2 and template-primer ligation products shows a single dominant product (20802, 20823 & 20845 Da species are the mono, di, tri-sodium complexes of the 20780 Da mass, respectively).

Ligation of BB1, BB2 & BB3 to the Template-Primer Complex.

Equimolar BB1, BB2, BB3 and template-primer complex was ligated as described above and examined using ES-MS.

The above sequence appears in the sequence listing as SEQ ID NO:7.

Figure 15:
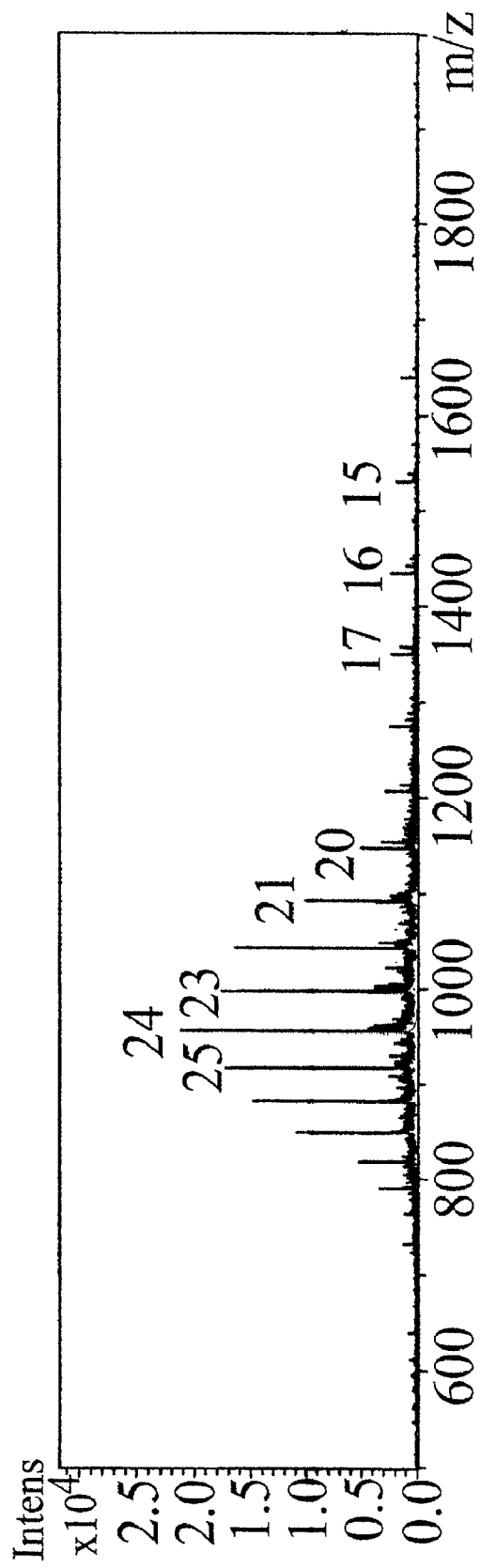
FIG. 15 is a mass spectrogram (SNJ45+32+39+33−270103.d: -MS, 3.7-6.6 min (#26-#47)) with the following labeled peaks: 25(A):917.6, 24(A):955.9, 23(A):997.5, 21(A):1092.6, 20(A):1147.3, 17(A):1349.8, 16(A):1434.2, 15(A):1529.9 m/z.

FIG. 15 is a mass spectrogram (SNJ45+32+39+33−270103.d: -MS, 3.7-6.6 min (#26-#47)) with the following labeled peaks: 25(A):917.6, 24(A):955.9, 23(A):997.5, 21(A):1092.6, 20(A):1147.3, 17(A):1349.8, 16(A):1434.2, 15(A):1529.9 m/z.

The ligation product had an expected mass of 22961 Da and an observed mass of 22963 Da (see component A).

| Component | Deconvoluted Mass | Molecule | Absolute Abundance | Relative Abundance |
|---|---|---|---|---|
| A | 22963.79 | [M − H]− | 134448 | 100.00 |
| B | 23089.12 | [M − H]− | 21052 | 15.66 |
| C | 23015.05 | [M − H]− | 17048 | 12.68 |

ES-MS of BB1, BB2 and BB3 ligated to the template-primer complex shows sequence specific ligation of BB1, BB2, and BB3 oligonucleotides each comprising a central carboxy-dT functionality.

Example 2

Ligation of Multiple Building Block 6-mer or 12-mer Oligonucleotides Comprising Chemical Entities In the following example, short 6 or 12-mer oligonucleotides are ligated to flanking oligonucleotides in a templated reaction and the products analysed by polyacrylamide gel electrophoresis (PAGE). Position 3 of each BB-oligonucleotide contains a C2 amino dT which can function as handle for the attachment of desired chemical entities (see scheme below). In this example the BB-oligonucleotides are modified with 4-PBA or SA using the following procedure.

4-PBA (4-penteneoyl-β-alanine) and SA (succinic acid) were both dissolved in 25 μl di-methyl fluoride (DMF), 200 mM final, and mixed with 25 μl 200 mM EDC dissolved in DMF. This mixture was incubated for 30 min at 25° C. Subsequently, 8 nano mole of BB-oligonucleotide dissolved in 50 μl 100 mM Hepes, pH 7.5, was included and allowed to react for 20 min at 25° C. BB-oligonucleotides were extracted twice with ethyl acetate in order to remove unreacted 4-BPA and SA.

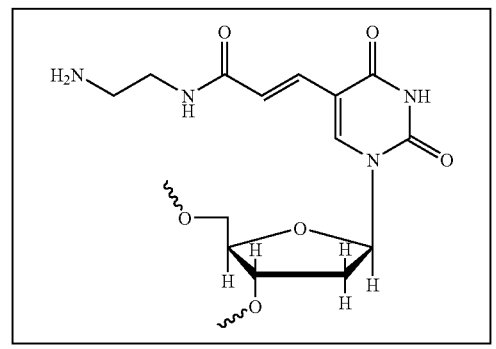

C2 Amino-modified dT

NNN(C2-amino-dT)NN
6 mer oligo

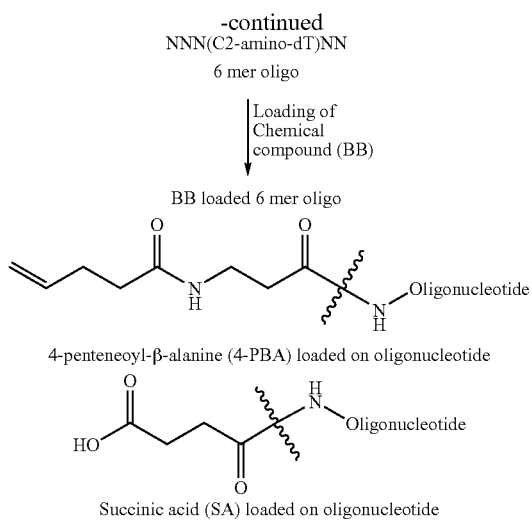

Structure of C2 amino dT and the chemical modifications 4PBA and SA loaded on either a 6-mer or 12-mer building block oligonucleotide containing C2 amino dT are shown above.

Modifications on oligonucleotides were verified by ES-MS before subjecting the oligonucleotides to template specific ligation.

The 5' flanking oligo was 5' $^{32}$P-labelled using T4 polynucleotide kinase. This was done to be able to visualise mobility shift of ligated products. Two pico mole of template and two pico mole of each of the two flanking oligos were mixed with 20 pico mole of 6-mer or 12-mer BB-oligonucleotides loaded with either 4-BPA or SA, heated 1 minute at 80° C. and allowed to anneal by cooling to 20° C. Annealed oligos were ligated at 20° C. for 1 hour using Takara ligase kit version 2.0 (TaKaRa™). The samples were denatured in SDS sample buffer and analysed by SDS-PAGE containing 8M UREA.

Schematic Representation of Experiment

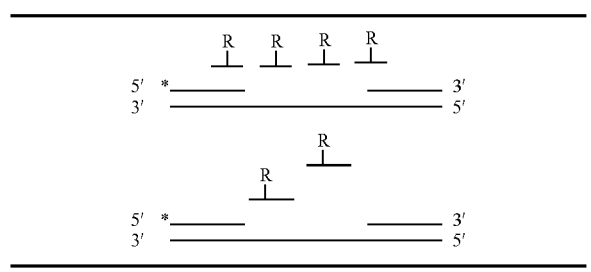

Figure 4:
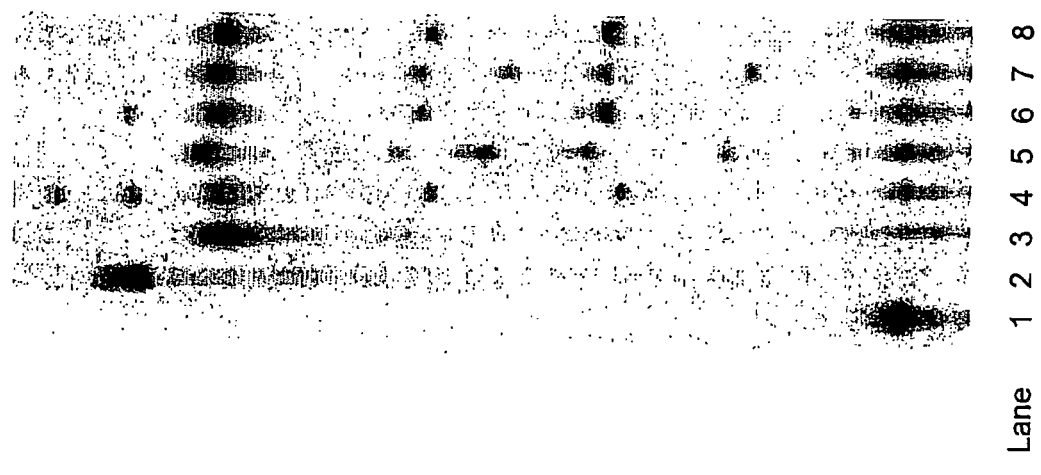
FIG. 4 discloses a photograph of a gel mentioned in example 2.
Figure 5:
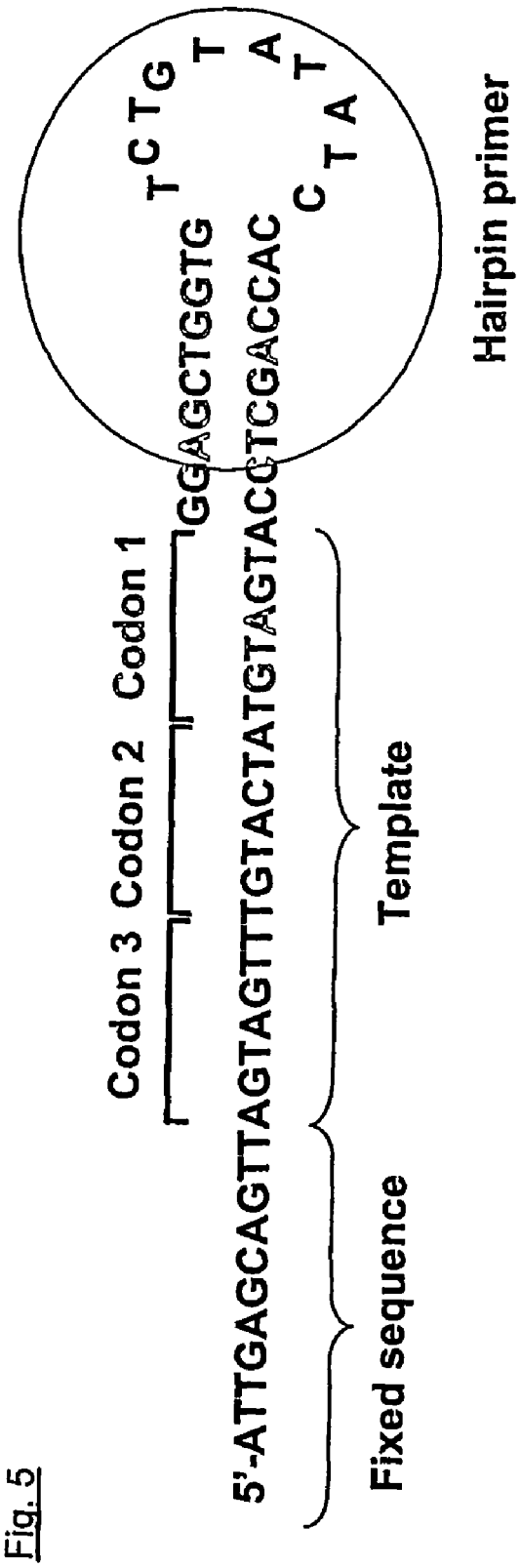
FIG. 5 discloses a reaction scheme in which a solid support is used for carrying the building block (the sequences, from top to bottom, are SEQ ID NOs:12, 13, 14 and 15)

The * marks represents a $^{32}$P-radiactively labelled primer and R marks the chemical modification on 6 or 12-mer BB-oligonucleotides. FIG. 4 shows the results of the experiment represented by a gel analysis of the ligation products. In FIG. 3 the lanes are numbered:

Lane 1: $^{32}$P primer
2: $^{32}$P template
3: 4×6 mer
4: 2×12 mer
5: 4×6 mer+4-PBA
6: 2×12 mer+4PBA
7: 4×6 mer+SA
8: 2×12 mer+SA The data shows that multiple 6 or 12-mer building block oligonucleotides can be efficiently ligated to flanking primers in a templated reaction using either 4-PBA or SA as attached chemical entity. Thus, ligation is template specific and unaffected by the attached chemical moiety.

Example 3

Transfer of a Chemical Entity to a Reactive Site

A 7-nucleotide anticodon oligonucleotide (A) with the sequence pATGXCAT, where X is C6 amino-dT (Glen Research cat# 10-1039-90) and p is photoprotected 5'-terminal phosphate (Glen Research cat# 10-4913-90) was obtained from DNA technology A/S Denmark. A second 7-nucleotide anticodon oligonucleotide (B) with the sequence 5'-pATCYGTA-3', where Y is carboxy-dT (Glen Research cat#10-1035-90) and p is a 5'-terminal phosphate group with a photoprotection group (Glen Research cat# 10-4913-90) was obtained from DNA technology A/S Denmark. All oligonucleotides were produced using standard phosphoamidite chemistry. Oligo B was loaded with a chemical entity comprising a cleavable linker as shown schematically below using the following protocols:

Synthesis of a Building Block:

N-Boc-Allyl-Glycine 0.12 mmol (26 mg) was dissolved in anhydrous acetonitrile and added 0.12 mmol (15 mg) 3-Amino-propionic acid methyl ester. The solution was cooled to 0° and added 1 mL of triethylamine and 0.12 mmol (45 mg) of HBTU. The reaction mixture was stirred over night at room temperature and evaporated to dryness. The remainder was dissolved in methanol (5 mL) and purified using reverse phase HPLC. (Yield: 53% (0.063 mmol, 19 mg)). The Boc protection group was removed by stirring the product in DCM containing 10% TFA for 1 hour at room temperature. Allyl Glycine Beta Alanine Methylester was obtained as triflouroacetate in approx. 100% yield (20 mg).

10 nmol of oligo B was dissolved in 50 µl of 200 mM Hepes-OH buffer pH 7.5 before addition of 20 µl of 100 mM of the chemical entity intermediate produced above in DMF, 20 µl 250 mM 1-ethyl-3-[3-dimethylaminopropyl]carbodiimide (EDC) and 10 µl 100 mM of N-hydroxysuccinimide (NHS) in a total volume of 100 µl. The sample is incubated at 30° C. for 4 hours. Subsequently, oligo B comprising the loaded chemical entity, i.e. the building block, is purified using HPLC.

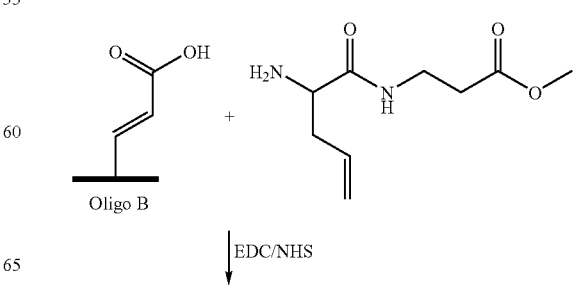

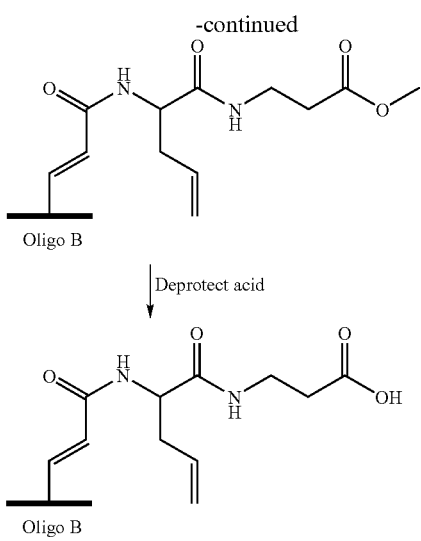

Oligo B

↓ Deprotect acid

Oligo B

The scheme above is a representation showing the synthesis of building block B comprising a DNA oligonucleotide sequence and a chemical entity.

Figure 7:
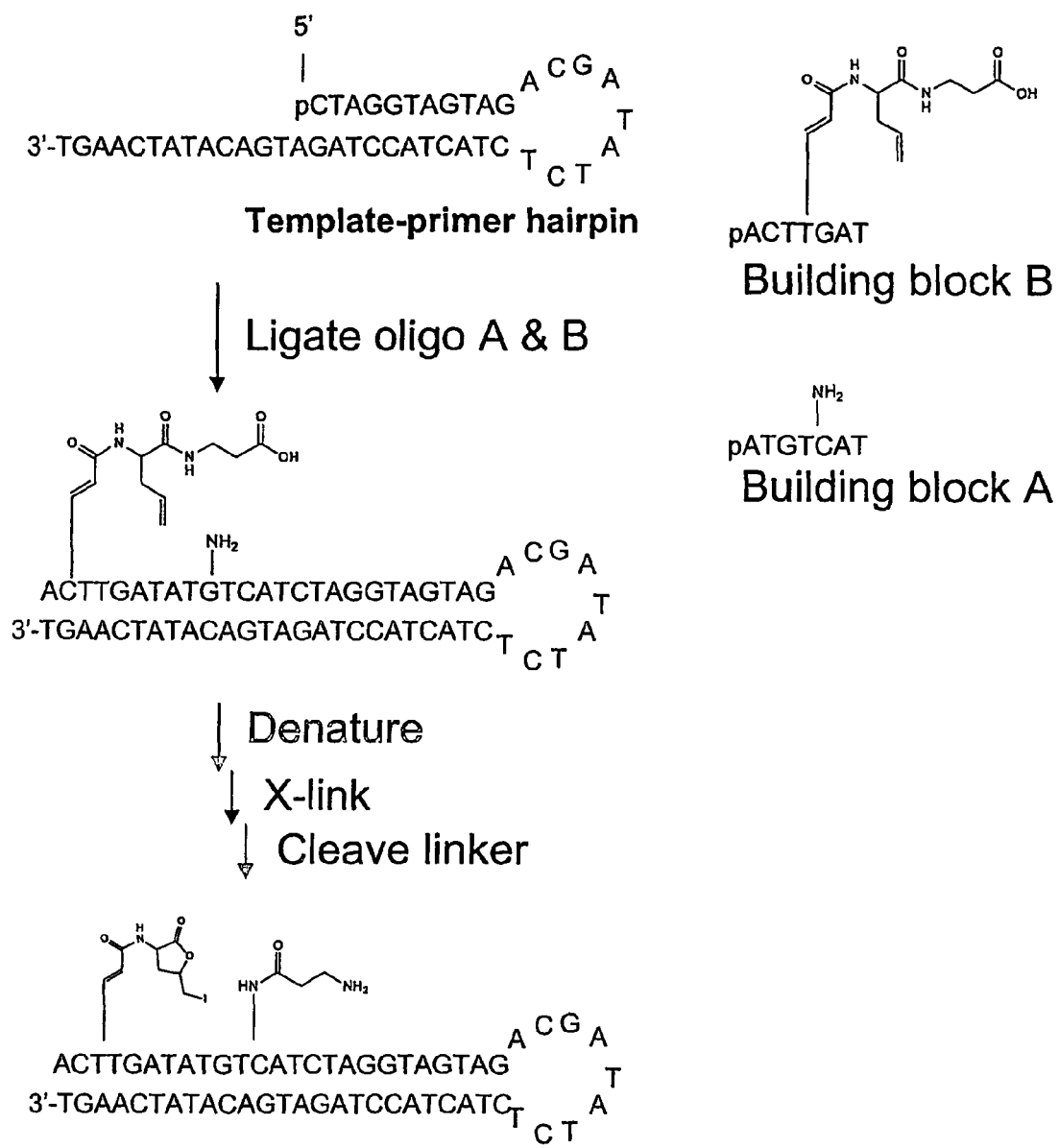
FIG. 7 shows a synthesis scheme for the reactions used in example 3. The hairpin sequences are, from top to bottom, SEQ ID NOs:10, 18, and 18, while building block B is SEQ ID NO:16 and A is SEQ ID NO:17.
Figure 8:
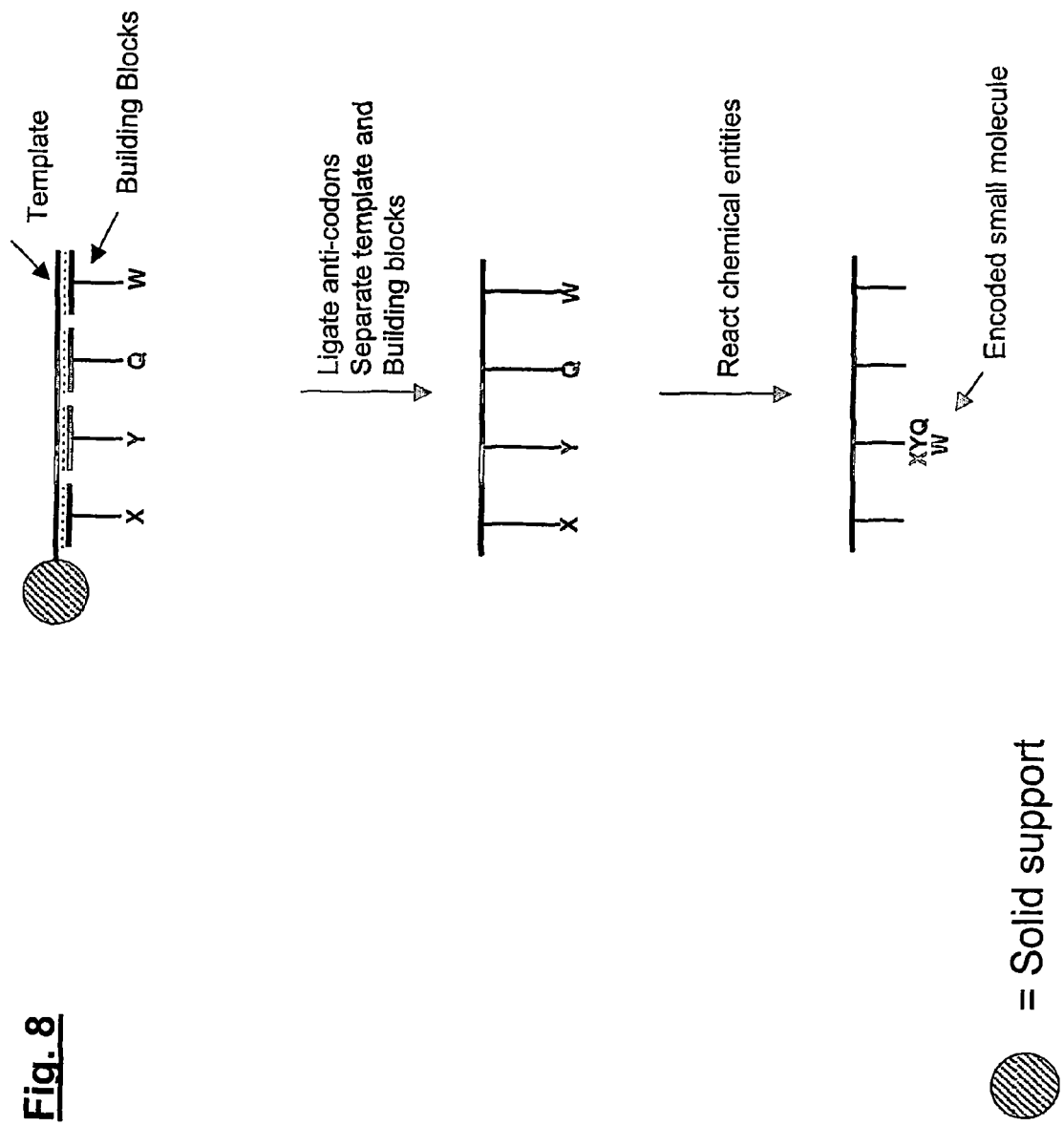
FIG. 8 shows a template linked to a solid support. The anti-codons of the building blocks are hybridised to the template without being covalently linked to said template. The anti-codons are then ligated and the template and building blocks are physically separated. Then the chemical entities are reacted to form an encoded small molecule.
Figure 9:
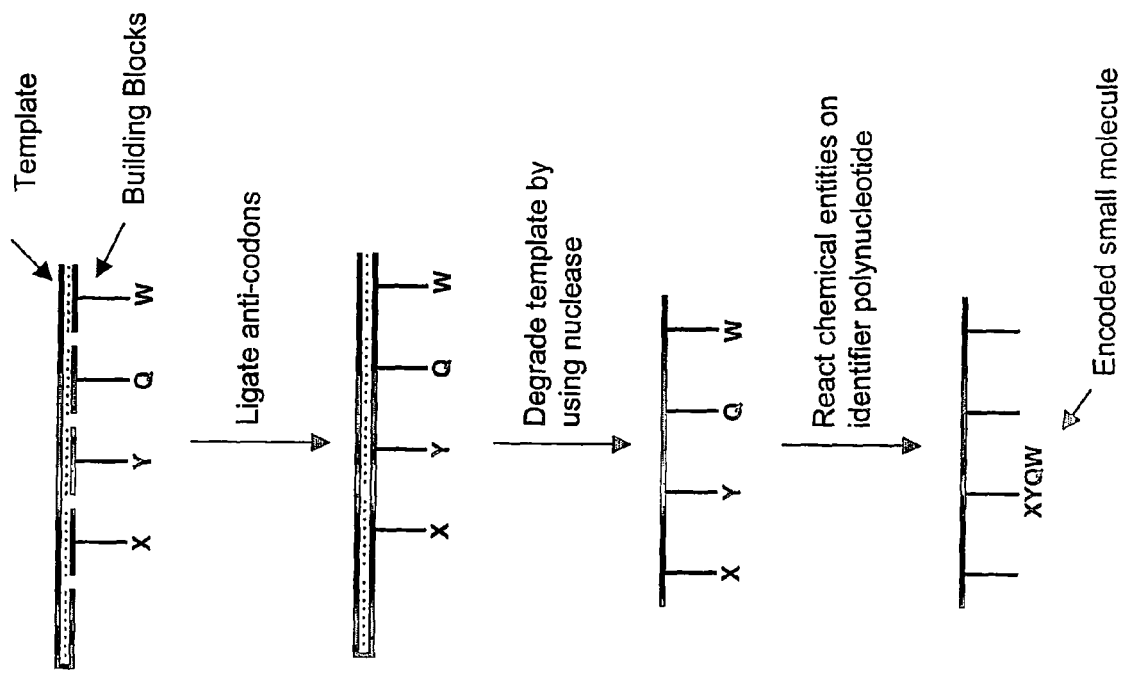
FIG. 9 shows a template comprising a hairpin loop and building blocks. The anti-codons of the building blocks are ligated and the template degraded by using nuclease. Then the chemical entities are reacted on the identifier polynucleotide to form an encoded small molecule.
Figure 10B:
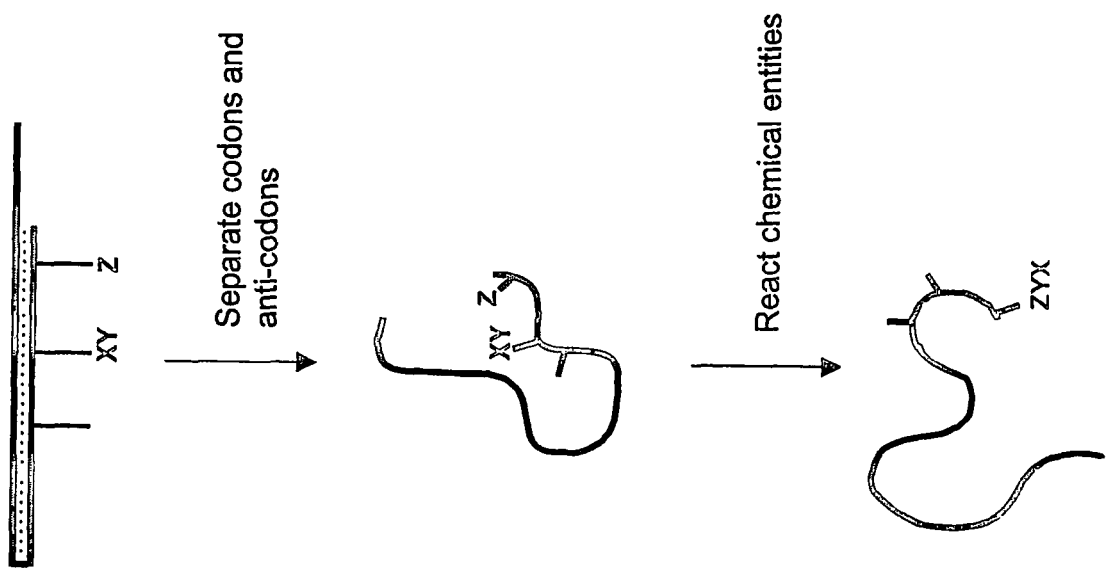
FIG. 10. (A) shows a template comprising a hairpin loop associated with a chemical entity. A building block is ligated thereto and the chemical entities of the template and building block are reacted on the identifier polynucleotide. Another building block comprising a chemical entity is then hybridized to the identifier oligonucleotide and the building block and identifier oligonucleotide are ligated. In (B), codons and anti-codons are separated and the chemical entities are reacted.
Figure 11C:
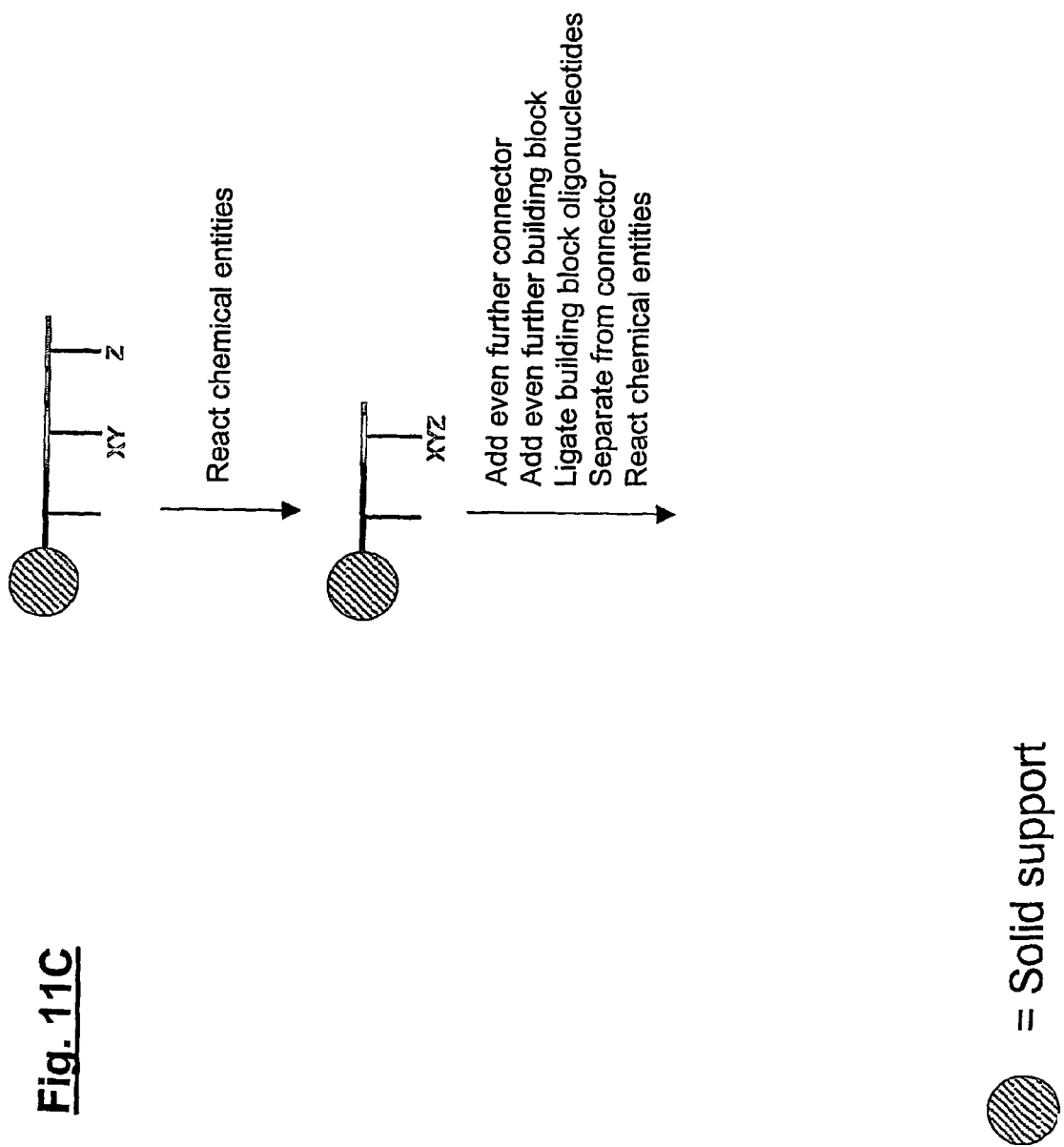
FIG. 11. (A) shows a building block immobilised to a solid support. A connector polynucleotide and a second building block are added. Then the building block oligonucleotides are ligated. The connector polynucleotide is displaced from the ligated building blocks. In (B), the chemical entities are reacted and a further building block is added with a further connector. Then the building block oligonucleotides are ligated and separated from the further connector. In (C), the chemical entities are reacted. The process may be repeated by adding an even further connector and building block.

The building blocks A and B were ligated to a template-primer complex having the sequence: 5'-pCTAGGTAGTA-GACGATATCTCTACTACCTAGATGACATATCAAGT-3'. The synthesis is schematically shown on FIG. 7. 10 pmol of building block A and 10 pmol of building block B were pre-activated by removal of the 5'-photoprotection group using a Vilber-Lourmat trans-illuminator and subjecting the sample to UV-light at 312 nm for 30 seconds. Next the anti-codon building blocks A and B were ligated to 10 pmol of template-primer complex using the TaKaRa ligation kit version 2.0. The three oligonucleotides were incubated in volume of 20 µl and were briefly denatured at 80° C. for 2 minutes before slowly cooling down to ambient temperature. An equivolume of TaKaRa ligation solution 1 was added and the sample incubated at ambient temperature for 1 hour. The ligation product was extracted twice in equivolumes of phenol before gelfiltration using Bio-rad microspin 6 columns. The ligation product was examined by electrospray-MS analysis (Bruker Inc.).

The ligation product was denatured by addition of 20 mM. NaOH for 2 minutes at 25° C. in a total volume of 10 µl before addition of 50 µl of 9.5 M urea dissolved in 100 mM Hepes-OH buffer pH 7.5 (final conc). 5 µl of 500 mM EDC and 5 µl of 200 mM NHS were added and the sample incubated overnight at ambient temperature. The sample was purified using double gel-filtration before testing the cross-linking product on Electrospray-MS (Bruker Inc.). Successful crosslinking was observed by the removal of water from the ligation product (i.e. removal of 18 Dalton from the total molecular mass). Following cross-linking, the linker was cleaved by addition of 10 µl of a solution containing 25 mM iodine in THF and incubated at 30° C. for 1 hour. The sample was purified by double gel-filtration using bio-rad 6 spin-columns before testing the cross-linking product on electrospray-MS analysis (Bruker Inc.). Successful cross-linking and cleavage of the linker was observed as the addition of iodine to the total mass without elimination of the β-alanine building block (which have been cross-linked and transferred to the amino-nucleophile of building block A).

The invention claimed is:

1. A method for synthesising a bifunctional complex comprising an encoded molecule and an identifier polynucleotide identifying the chemical entities having participated in the synthesis of the encoded molecule, said method comprising the steps of
   providing
   a) at least one template comprising one or more codons capable of hybridising to an anti-codon, and
   b) a plurality of building blocks each comprising an anti-codon associated with one or more chemical entities, and
hybridising the anti-codon of one or more of the provided building blocks to the template,
covalently linking each of said anti-codons to at least one other anti-codon and optionally covalently linking the at least one template with the anti-codon of at least one building block, thereby generating an identifier polynucleotide capable of identifying chemical entities having participated in the synthesis of the encoded molecule,
separating the template from one or more of the anti-codons hybridised thereto, thereby generating an at least partly single stranded identifier polynucleotide associated with a plurality of chemical entities,
wherein at least part of the template is covalently linked to the identifier polynucleotide in the form of covalently linked anti-codons, and/or
wherein chemical entities of different building blocks are reacted under conditions wherein the identifier polynucleotide is at least essentially single stranded,
generating a bifunctional complex comprising an encoded molecule and an identifier polynucleotide identifying the chemical entities having participated in the synthesis of the encoded molecule,
   wherein said encoded molecule is generated by reacting at least two of said plurality of chemical entities associated with the identifier polynucleotide,
   wherein said at least two chemical entities are provided by separate building blocks.

2. The method of claim 1, wherein the template is separated from said covalently linked anti-codons by chemically or enzymatically cleaving one or more nucleotide linking bonds of the template.

3. The method of claim 1, wherein the template is separated from said covalently linked anti-codons in a separation step selected from the group consisting of i) a step involving heating the template and the covalently linked anti-codons, thereby displacing the template from the covalently linked anti-codons, and ii) a step involving washing the template and the covalently linked anti-codons in a solvent resulting in displacing the template from the covalently linked anti-codons, wherein said steps are optionally followed by one or more washing steps.

4. The method of claim 1, wherein at least one of said covalently linked anti-codons is further linked to a solid support, wherein the template is hybridised to the covalently linked anti-codons without being covalently linked to said covalently linked anti-codons, and wherein the template is separated from the covalently linked anti-codons by a step involving heating the template and the covalently linked anti-codons and/or a washing step resulting in physically separating the template from the covalently linked anti-codons.

5. The method of claim 1, wherein the template is linked to a solid support, wherein said covalently linked anti-codons are hybridised to the template without being covalently linked to said template, and wherein the covalently linked anti-codons are separated from the template by a step involving heating the template and the covalently linked anti-codons and/or a washing step resulting in physically separating the covalently linked anti-codons from the at least one template.

6. The method of claim 5, wherein at least one of said covalently linked anti-codons are further linked to one member of an affinity pair, wherein the other member of said affinity pair is linked to a further solid support, wherein the linkage of said affinity pair members results in attaching said covalently linked anti-codons to said further support.

7. The method of claim 2,
wherein the identifier polynucleotide consists of covalently linked anti-codons.

8. The method of claim 2,
wherein the identifier polynucleotide does not comprise the template, or a part thereof.

9. The method of claim 1,
wherein the anti-codon of one of the provided building blocks is hybridised to the template,
wherein the anti-codon is covalently linked to the template,
wherein the anti-codon is displaced from the template, thereby generating an at least essentially single stranded identifier polynucleotide associated with a plurality of chemical entities,
wherein at least two of said plurality of chemical entities associated with the at least essentially single stranded identifier polynucleotide are reacted, thereby generating a bifunctional complex comprising a first encoded molecule and an identifier polynucleotide coding for chemical entities having participated in the synthesis of the first encoded molecule.

10. The method of claim 9 comprising the further steps of
   i) hybridising the anti-codon of at least one further building block to the identifier polynucleotide of the first bifunctional complex, wherein said anti-codon is associated with one or more chemical entities,
   ii) covalently linking the anti-codon and the identifier polynucleotide of the first bifunctional complex,
   iii) displacing the anti-codon from the identifier polynucleotide of the first bifunctional complex, thereby generating an at least essentially single stranded second identifier polynucleotide associated with the first encoded molecule and one or more chemical entities,
   iv) reacting the first encoded molecule and the one or more chemical entities, and
   v) generating a second bifunctional complex comprising a second encoded molecule and the second identifier oligonucleotide identifying the plurality of chemical entities having participated in the synthesis of the second encoded molecule.

11. The method of claim 10, wherein steps i) to iv) are repeated for building blocks comprising different anti-codons and/or different chemical entities, thereby generating a plurality of bifunctional complexes comprising different encoded molecules.

12. The method of claim 1, wherein the template comprises from 2 to preferably less than 100 codons, such as from 2 to preferably less than 10 codons.

13. The method of claim 1, wherein each codon comprises from 3 to 30 nucleotides.

14. The method of claim 1, wherein at least one of said building blocks comprise a chemical entity comprising a scaffold moiety comprising a plurality of reactive groups, and/or wherein the template is linked to a chemical entity comprising a scaffold moiety comprising a plurality of reactive groups.

15. The method of claim 14, wherein said scaffold moiety reactive groups react with one or more chemical entities of a single building block, or one or more chemical entities of different building blocks.

16. The method of claim 1, wherein at least one building block or a subset of said plurality of building blocks are provided sequentially and/or sequentially hybridised to the template, wherein said sequentially provided and/or hybridised building block anti-codons are ligated, and wherein chemical entities of said subset of sequentially provided building blocks react before a further subset of building blocks are provided and/or hybridised to the template.

17. The method of claim 1, wherein at least some building block anti-codons are ligated to the anti-codon of a neighbouring building block and/or to a template by a ligase, thereby covalently linking said building block anti-codons.

18. The method of claim 1, wherein the at least essentially single stranded identifier polynucleotide is obtained by displacing codons and anti-codons under denaturing conditions resulting in said displacement.

19. The method of claim 2 comprising the further step of degrading the template part of the identifier polynucleotide before any of the chemical entities are reacted.

20. The method of claim 1 comprising the further step of separating the template from a plurality of covalently linked anti-codons before reacting any chemical entities, reacting the chemical entities and generating a bifunctional complex comprising an encoded molecule and an identifier oligonucleotide consisting solely of ligated anti-codons, wherein said identifier oligonucleotide identifies the chemical entities having participated in the synthesis of the encoded molecule.

21. The method of claim 20, wherein the template is removed by cleaving at least one covalent link linking template codons and building block anti-codons, subjecting to cleavage product to conditions eliminating hybridisation between template codons and building block anti-codons, and separating the template from the covalently linked anti-codons.

22. The method of claim 21, wherein the covalent link is cleaved by a restriction endonuclease.

23. The method of claim 1 comprising the further step of separating codons and anti-codons by hybridising a nucleic acid to the template part of the molecule, thereby generating a duplex comprising the template.

24. The method of claim 1, wherein a plurality of bifunctional complexes are generated from the hybridisation of a plurality of templates to a plurality of building block anti-codons, covalently linking anti-codons hybridised to the same template, separating the template from at least some of the covalently linked anti-codons, preferably by degrading the template or by cleaving at least one chemical bond linking the template to the covalently ligated anti-codons followed by physical separation of the template and the covalently linked anti-codons, reacting the chemical entities and generating a library of bifunctional complexes each comprising a different encoded molecule and an identifier polynucleotide identifying the chemical entities having participated in the synthesis of the encoded molecule, wherein each of the plurality of encoded molecules are generated by reacting chemical entities associated with different anti-codons.

25. The method of claim 1,
wherein the anti-codons of from 3 to 8 building blocks are hybridised to a template sequentially or simultaneously in the same first compartment,
wherein at least one of the building blocks comprise a scaffold moiety comprising a plurality of reactive groups associated to an anti-codon,
wherein the template is covalently bound to a solid support, such as a beaded polymer,
wherein the covalently linked anti-codons are separated from the template covalently bound to the solid support,
wherein said separation results in anti-codons and codons not being hybridised to each other, optionally transferring the covalently ligated anti-codons to a second compartment, or transferring the template covalently bound to a solid support to a second compartment, and
reacting the chemical entities associated with the identifier polynucleotide, optionally in a compartment different from the compartment harbouring the template.

26. The method of claim 1,
wherein the anti-codons of from 3 to 8 building blocks are hybridised to a template sequentially or simultaneously in the same first compartment,
wherein at least one of the building blocks comprise a scaffold moiety comprising a plurality of reactive groups associated with an anti-codon,
wherein the covalently linked anti-codons are initially covalently linked to the template,
wherein the template part of the identifier oligonucleotide is degraded, thereby generating an identifier oligonucleotide comprising an essentially single stranded molecule comprising no template sequence,
optionally transferring the covalently ligated anti-codons to a second compartment, and
reacting the chemical entities associated with the identifier polynucleotide.

27. The method of claim 26, wherein the building blocks are provided sequentially, and wherein said method comprises the further steps of
  i. covalently linking the anti-codon of a sequentially added building block to the template, or covalently linking the anti-codon of a sequentially added building block to an anti-codon covalently linked to the template,
  ii. selecting a set of reaction conditions wherein codons and anti-codons do not hybridise to each other, thereby generating an essentially single stranded molecule,
  iii. reacting a chemical entity of a sequentially added building block with a chemical entity associated with the template, or with a chemical entity associated with an anti-codon covalently linked to the template, and
  iv. repeating steps i) to iii) for different building blocks.

28. A method for synthesising one or more bifunctional complexes each comprising a molecule resulting from the reaction of a plurality of chemical entities and an identifier polynucleotide identifying one or more of the chemical entities having participated in the synthesis of the molecule, said method comprising the steps of
  i. providing a plurality of building blocks each comprising an oligonucleotide associated with one or more chemical entities, ii. providing at least one connector oligonucleotide capable of hybridising with one or more building block oligonucleotides,
iii. immobilising at least one building block to a solid support,
iv. hybridising said immobilized building block oligonucleotide to a first connector oligonucleotide,
v. hybridising at least one additional building block oligonucleotide to said first connector oligonucleotide,
vi. covalently ligating each building block oligonucleotide to at least one other building block oligonucleotide, at least one of said covalently ligated building block oligonucleotides being hybridised to the connector oligonucleotide,
vii. separating the connector polynucleotide from the ligated building block oligonucleotides,
viii. reacting one or more chemical entities associated with different building block oligonucleotides, thereby obtaining a first bifunctional complex comprising a first molecule or first molecule precursor linked to a first identifier oligonucleotide identifying the chemical entities having participated in the synthesis of the molecule or molecule precursor, wherein said first bifunctional complex is immobilised to a solid support.

29. The method of claim 28 comprising the further steps of
i. providing a second connector polynucleotide,
ii. hybridising said second connector polynucleotide to the identifier polynucleotide of said first bifunctional complex,
iii. hybridising at least one further oligonucleotide of a building block to said second connector oligonucleotide,
iv. ligating building block oligonucleotides hybridised to the second connector oligonucleotide, wherein at least one of said building block oligonucleotides are hybridised to the first identifier polynucleotide,
v. separating the second connector polynucleotide from the ligated building block oligonucleotides, for example by diverting the second connector polynucleotide to another compartment,
vi. reacting the first molecule precursor with the one or more chemical entities associated with the ligated building block oligonucleotide(s), thereby obtaining a second bifunctional complex comprising a molecule or molecule precursor linked to a second identifier polynucleotide identifying the chemical entities having participated in the synthesis of the molecule or molecule precursor, wherein said second bifunctional complex is immobilised to a solid support.

30. A method for synthesising a bifunctional complex comprising a molecule resulting from the reaction of a plurality of chemical entities, wherein said molecule is linked to an identifier polynucleotide identifying one or more of the chemical entities having participated in the synthesis of the molecule, said method comprising the steps of
i) providing a plurality of building blocks selected from the group consisting of
a) building blocks comprising an identifier oligonucleotide linked to one or more chemical entities,
b) building blocks comprising an identifier oligonucleotide linked to one or more reactive groups, and
c) building blocks comprising an identifier oligonucleotide comprising a spacer region, wherein said building blocks comprising a spacer region are preferably connector polynucleotides to which building blocks of groups a) and b) can hybridise,
ii) generating a hybridisation complex comprising at least n building blocks by hybridising the identifier oligonucleotide of one building block to the identifier oligonucleotide of at least one other building block,
wherein n is an integer of 4 or more
wherein at least 3 of said at least n building blocks comprise a chemical entity,
wherein no single identifier oligonucleotide is hybridised to all of the remaining identifier oligonucleotides,
wherein optionally at least one of said building blocks of group c) is immobilised to a solid support, thereby providing a handle to which an oligonucleotide of at least one building block of groups a) or b) can hybridise,
iii) covalently linking identifier oligonucleotides of building blocks comprising one or more chemical entities, thereby obtaining an identifier polynucleotide comprising covalently linked identifier oligonucleotides each associated with one or more chemical entities,
iv) optionally separating said identifier polynucleotide obtained in step iv) from any immobilised connector oligonucleotides hybridized thereto, wherein said separation optionally comprises the step of diverting said identifier polynucleotide comprising covalently linked identifier oligonucleotides each associated with one or more chemical entities to a different reaction compartment, thereby separating said identifier polynucleotide from said immobilised connector oligonucleotides
v) reacting said at least 3 chemical entities linked to the identifier polynucleotide, and
vi) obtaining a bifunctional complex comprising a molecule resulting from the reaction of a plurality of chemical entities, wherein said molecule is linked to an identifier polynucleotide identifying one or more of the chemical entities having participated in the synthesis of the molecule.

31. The method of claim 30 wherein a plurality of different bifunctional complexes is obtained by repeating the method steps for different building blocks.

* * * * *